United States Patent
Livneh et al.

(10) Patent No.: US 6,333,178 B1
(45) Date of Patent: Dec. 25, 2001

(54) METHODS OF REPLICATING A DNA MOLECULE FOR REPAIR OF DNA LESION DAMAGE OR FOR MUTAGENESIS

(75) Inventors: Zvi Livneh, Rehovot (IL); Nina Bacher Reuven, Bloomfield, CT (US); Guy Tomer, Portland, OR (US)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 09/660,552

(22) Filed: Sep. 12, 2000

Related U.S. Application Data

(63) Continuation-in-part of application No. 09/627,399, filed on Jul. 27, 2000, now abandoned.
(60) Provisional application No. 60/146,162, filed on Jul. 30, 1999.

(51) Int. Cl.[7] .............................. C12P 19/34; C12Q 1/68
(52) U.S. Cl. .............................................. 435/91.1; 435/6
(58) Field of Search ........................................ 435/91.1, 6

(56) References Cited

PUBLICATIONS

Reuven N.B. et al., "The mutagenesis proteins UmuD' and UmuC prevent lethal frameshifts while increasing base substitutions mutations", Mol. Cell, vol. 2, pp. 191–199 (1998).*

Reuven N.B. et al., "The Mutagenesis Protein UmuC Is a DNA Polymerase Activated by UmuD', Reca and SSB and Is Specialized for Translesion Replication", J. Biol. Chem. vol. 274, pp. 31763–31766 (1999).*

Maor–Shoshani et al., "Highly mutagenic replication by DNA polymerase V (UmuC) provides a mechanistic basis for SOS untargeted mutagenesis", Biochemistry, 97(2)565–570 (2000).

Tang et al., "UmuD'$_2$C is an error–prone DNA polymerase, Escherichia coli pol V", Proc. Natl. Acad. Sci. USA, 96:8919–8924 (1999).

Tang et al., "Roles of E. coli DNA polymerases IV and V in lesion–targeted and untargeted SOS mutagenesis", Nature, 404:1014–1018 (2000).

Tang et al., "Biochemical basis of SOS–induced mutagenesis in Escherichia coli: Reconstitution of in vitro lesion bypass dependent of the UmuD'$_2$C mutagenic complex and RecA protein", Proc. Natl. Acad. Sci. USA, 95:9755–9760 (1998).

* cited by examiner

Primary Examiner—Kenneth R. Horlick
Assistant Examiner—Teresa Strzelecka
(74) Attorney, Agent, or Firm—Browdy and Neimark

(57) ABSTRACT

UmuC is found to be a translesion replication DNA polymerase which replicates in the presence of UmuD', RecA and SSB through a DNA lesion of damaged DNA molecule and which is found to be highly mutagenic during in vitro gap-filling replication. A method for replicating a DNA molecule with DNA lesion damage and a method for mutagenesis of a DNA molecule are provided.

38 Claims, 27 Drawing Sheets

FIG. 8
| UmuC, UmuD' RecA, SSB | − | + | + |
|---|---|---|---|
| Pol II | + | − | + |
| Time⁺ | ◢ | ◢ | ◢ |
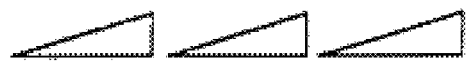
— 43
— 25
— 15
1 2 3 4 5 6 7 8 9 10 11

| M-UmuC | + | + | - | + | + |
|---|---|---|---|---|---|
| UmuD' | + | + | + | - | + |
| RecA | - | + | + | + | + |
| SSB | + | - | + | + | + |
| Time | ◿ | ◿ | ◿ | ◿ | ◿ |
| | 1 2 3 | 4 5 6 | 7 8 9 | 10 11 12 | 13 14 15 |

— F II

FIG. 12
| Pol III core, nM | - | 30 | 90 | 90 |
|---|---|---|---|---|
| M-UmuC, UmuD', RecA, SSB | + | + | + | - |
| | 1 | 2 | 3 | 4 | 5 |
47 —
29 —
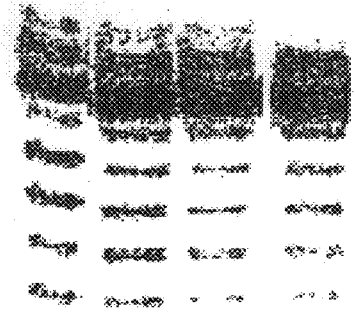
19 —
| Lesion bypass, % | 32 | 32 | 27 | <0.5 |

FIG. 14
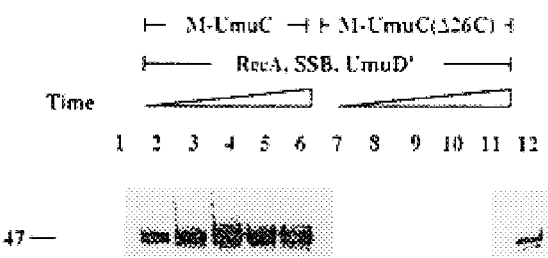
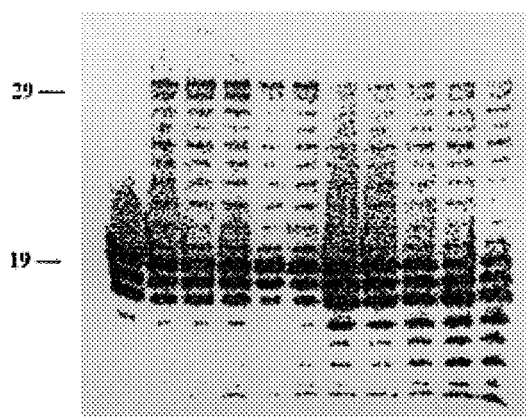
FIG. 15
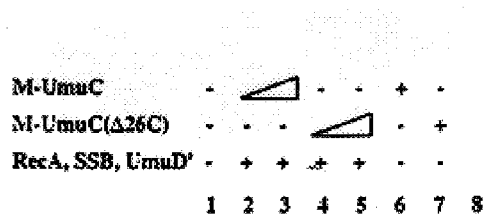
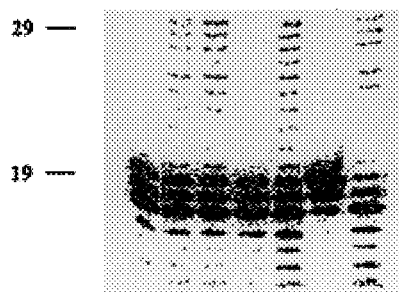

Transformation of an E.coli Tester Strain
Analysis of Cro⁻ mutants

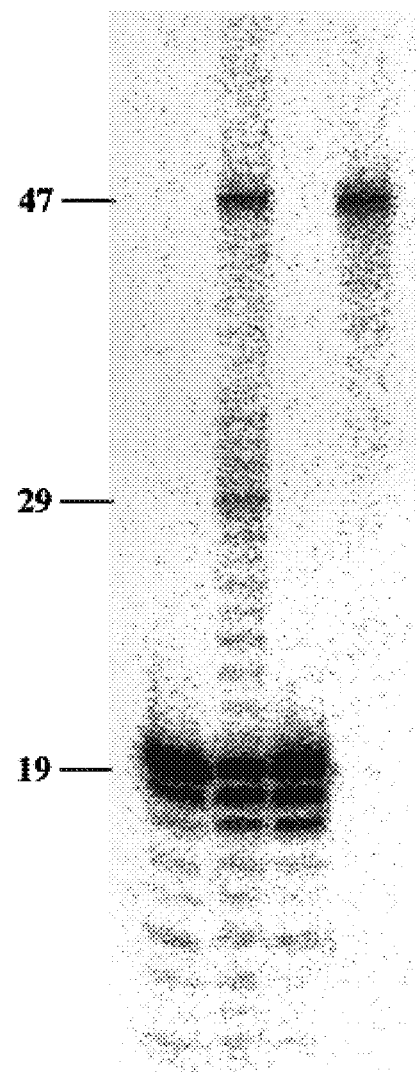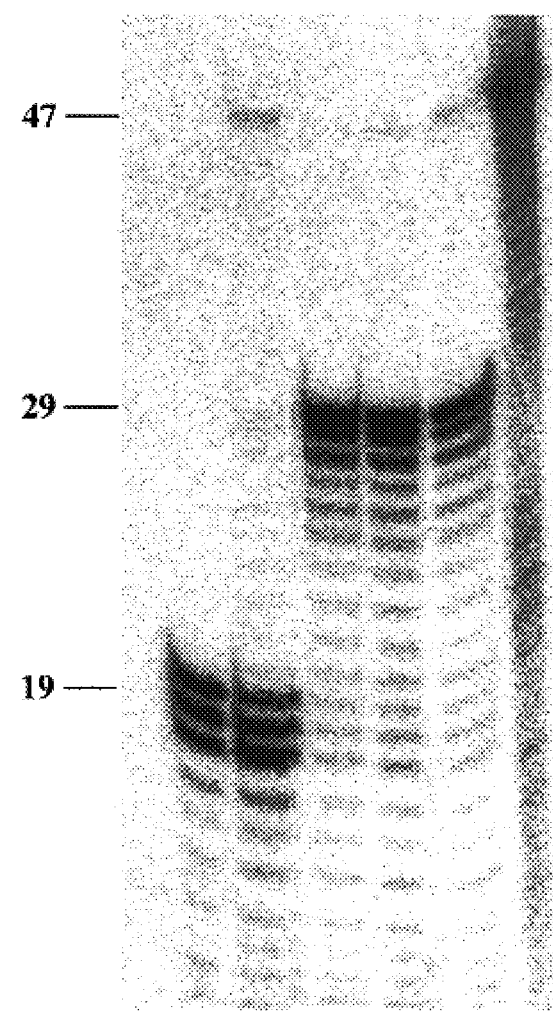

METHODS OF REPLICATING A DNA MOLECULE FOR REPAIR OF DNA LESION DAMAGE OR FOR MUTAGENESIS

CROSS-REFERENCE TO RELATED APPLICATIONS

The present application is a continuation-in-part of application Ser. No. 09/627,399, filed Jul. 27, 2000, abondoned, which claims priority under 35 U.S.C. §119(e) from U.S. provisional application No. 60/146,162 filed Jul. 30, 1999, the entire contents of Ser. Nos. 09/627,399 and 60/146,162 are hereby incorporated by reference.

BACKGROUND OF THE INVENTION

1. Field of the Invention

The present invention relates to replication of damaged DNA and to mutagenesis of DNA by highly mutagenic replication.

2. Description of the Related Art

Genomic DNA is continuously subjected to damage by internal and external agents, such as reactive oxygen species or sunlight, and by spontaneous decay (e.g., depurination). The DNA lesions produced interfere with replication and with gene expression and they must be removed by DNA repair enzymes in order to enable proper function of DNA. When unrepaired lesions are replicated, they give rise to mutations due to their miscoding potential (Friedberg et al., 1995). This is of major interest from the human disease standpoint, since the formation of mutations in critical target genes (oncogenes and tumor suppressor genes) leads to cancer. It has been estimated that most human cancers are caused by unrepaired DNA lesions (Sancar, 1994).

A broad class of DNA lesions, including UV light-induced pyrimidine cyclobutyl dimers or 6–4 adducts, abasic sites, or DNA adducts produced by certain drugs, such as cisplatin, interrupt DNA replication, leading to the formation of single-stranded regions. Such structures, ssDNA (single-stranded DNA) regions carrying damaged bases (gap lesion structures), cannot be repaired by the regular excision repair pathways, because that would lead to a double-strand break, which is highly lethal. The emergency tolerance strategy adopted for such cases is to repair (fill in) the gap without removing the damaged base. This converts the single-stranded region back into a duplex structure, thus restoring DNA continuity and reducing the risk of chromosome breakage. Excision repair mechanism might then have, at a later stage, a second chance to remove the lesion (Livneh et al., 1993; Friedberg et al., 1995).

Two general mechanisms are known for filling-in of gap lesion structures. Recombinational repair relies on the homologous fully replicated sister chromatid to provide a DNA segment that is patched across the lesion. This process is fundamentally error-free and is a major repair function in *E. coli* (Kowalczykowski et al., 1994; Eggleston et al., 1996). The second strategy consists of filling-in of the gap lesion by a DNA polymerase. This mechanism is mutagenic because polymerases tend to incorporate incorrect nucleotides opposite DNA lesions. In *E. coil*, this process, which is the paradigm for genetically regulated mutagenesis, is under tight regulation by the SOS stress response and requires specific inducible proteins. Its major outcome is a dramatic increase in mutations associated with DNA damage. It was termed error-prone DNA repair, SOS repair, or SOS mutagenesis (referring to its outcome), or translesion replication (referring to its mechanism; reviewed in Livneh et al., 1993; Walker, 1995). Two suggestions were offered to explain the function of such a system in *E. coli*. First is the repair of DNA gaps (opposite lesions) on which recombination cannot act (e.g., overlapping daughter strand gaps). The price of this repair is an increase in mutation frequency. The second is the facilitated adaptation of cell populations to environmental stress condition, via an inducible mutagenesis mechanism (Radman, 1975, Witkin, 1976; Bridges, 1978; Echols, 1981). The latter function is particularly intriguing because it implies an active mode of evolution (Echols, 1981).

In addition to this mutagenesis process, which is targeted to DNA lesions, a mutator activity is induced under SOS conditions, which produces mutations in the apparent absence of DNA damage (untargeted mutagenesis) (Witkin, 1974; George et al., 1975; Witkin et al., 1979). Chromosomal untargeted mutagenesis requires the SOS-inducible proteins RecA, UmuD', and UmuC (Witkin, 1976; Ciesla, 1982; Fijalkowska et al., 1997), the same proteins that are required for translesion replication. In addition, it exhibits a particular mutational specificity, namely, the selective generation of transversions (Fijalkowska et al., 1997; Miller et al., 1984; Yatagai et al., 1991; Watanabe-Akanuma et al., 1997). Another pathway of untargeted mutagenesis is observed by transfecting UV-irradiated *E. coli* cells with unirradiated phage λ (Ichikawa-Ryo et al., 1975). This phage untargeted mutagenesis requires the dinB, uvrA, and polA gene products (Maenhaut-Michel et al., 1984; Brotcorne-Lannoye et al., 1986; Caillet-Fauquet et al., 1988; Kim et al., 1997) and produces frameshift mutations (Wood et al., 1984). Recently, dinB (a homologue of umuC) was shown to encode an error-prone DNA polymerase termed pol IV, which tends to produce frameshifts (Wagner et al., 1999). The role of pol IV in *E. coli* cells is not clear, because dinB mutants are proficient both in untargeted and targeted SOS mutagenesis (Brotcorne-Lannoye et al., 1986; Kenyon et al., 1980).

In *E. coli*, the major tolerance mechanism toward unrepaired lesions is recombinational repair. In contrast, recombinational repair in mammals is less active (Friedberg et al., 1995), perhaps because of the large proportion of repetitive sequences in the mammalian genome, which increases the danger of undesired gross rearrangements. This leaves translesion replication as the major candidate for tolerance of unrepaired lesions in mammals. The scarcity of knowledge on mammalian tolerance of DNA damage underscores the importance of elucidating similar mechanisms in model organisms such as bacteria and yeast.

Based on genetic analysis, SOS mutagenesis in *E. coli* required DNA polymerase III (Bridges et al., 1976; Brotcorne-Lannoye et al., 1985), which is the replicative DNA polymerase, as well as three SOS-inducible proteins: RecA, UmuD', and UmuC. RecA is a multifunctional protein, known to be the major recombinase in *E. coli* (Roca and Cox, 1990), but its function in SOS mutagenesis is not directly related to recombination. RecA fulfills three roles in SOS mutagenesis, of which two are regulatory (Witkin, 1991): First, it activates the SOS stress response by promoting the cleavage of the LexA repressor. This induces the expression of the mutagenesis-specific proteins UmuD and UmuC. Second, it promotes the posttranslational cleavage of UmuD to UmuD', the active form in mutagenesis (Burckhardt et al., 1988; Nohmi et al., 1988; Shinagawa et al., 1988). In addition, RecA has been suggested to have a third, presumably direct, role in the mutagenic process (Dutreix et al., 1989; Sweasy et al., 1990). UmuD' and UmuC are specifically required for SOS mutagenesis (Kato and Shinoura, 1977). A pioneering study by Rajagopalan et al. (1992) indicated the UmuD' and UmuC act as bypass factors and increase translesion replication by pol III holoenzyme. However, the further utilization of that experimental system was hampered by the difficulty in obtaining purified active UmuC (Woodgate et al., 1989).

Two homologues of the *E. coli* umuC gene were recently found in the yeast *S. cerevisiae*. The REV1 gene is required for UV mutagenesis and encodes a dCMP transferase (Nelson et al., 1996). The RAD30 gene encodes DNA polymerase η, a translesion replication DNA polymerase which effectively and accurately bypasses cyclobutyl pyrimidine dimers, the major UV lesions (Johnson et al., 1999 and Johnson et al.; 1996). In addition yeast cells contain DNA polymerase ζ, which is required for UV mutagenesis, but is not a homolog of umuC. It is encoded by the REV3 and REV7 genes (Nelson et al., 1996). Human cells contain 4 proteins which belong to this superfamily: DNA polymerase η is encoded by the XP-V (hRAD30A) gene (Masutani et al., 1999 and Johnson et al., 1999). This protein is defective in the genetic disease Xeroderma Pigmentosum Variant, which causes sunlight sensitivity, and predisposition to skin cancer. The function of two other homologues, DNA polymerase ι, encoded by hRAD30B (McDonald et al., 1999 and Tissier et al., 2000), and DNA polymerase θ, encoded by hDINB1 (Gerlach et al., 1999 and Johnson et al., 2000); also termed DNA polymerase κ, (Ohashi et al., 2000), is still unknown. Human cells contain also the REV1 gene, which encodes a dCMP transferase (Lin et al., 1999 and Gibbs et al., 2000), and a homologue of the yeast REV3 gene, which were shown to be required for UV mutagenesis in human cells (Gibbs et al., 1998).

An interesting group of umuC and umuD homologues contains genes residing on native conjugative plasmids. These plasmids have a broad host range specificity, and they often carry multiple antibiotics resistance genes (Woodgate et al., 1992). Their existence in human pathogenic bacteria may account, in part, for the growing problem of antibiotics resistance among bacterial pathogens (Davies, 1994; Dennesen et al., 1998 and Swartz, 1994). The most extensively studied of these is the mucAB operon, carried on plasmid pKM101 (Perry et al., 1982), which is a natural variant of plasmid R46. Plasmid pKM101 was introduced into the Salmonella strains used in the Ames test for mutagens, where it increased the sensitivity of the assay via mucAB-mediated mutagenesis (McCann et al., 1975). Other known plasmidic umuDC homologues include, impCAB (Lodwick et al., 1990), Sam AB (Nohmi et al., 1991), and rum AB (Kulaeva et al., 1995). The laboratory of the present inventors have previously overproduced MucA, MucA' and MucB, and showed that MucA' forms a homodimer, and that MucB is a ssDNA-binding protein (Sarov-Blat et al., 1998). In addition, the laboratory of the present inventors found that MucB interacts with a SSB-coated ssDNA, causing a major conformational change, but without causing massive dissociation of SSB from the DNA (Sarov-Blat et al., 1998).

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a method for replicating a DNA molecule with DNA lesion damage by incubating a translesion replication DNA polymerase, which is UmuC (designated DNA Polymerase V) or a functional prokaryotic homologue thereof, with a sample containing a DNA molecule with one or more sites of DNA lesion damage in the presence of nucleoside 5'-triphosphates, a divalent metal ion, and a combination of UmuD', RecA and single stranded DNA-binding protein (SSB), or functional prokaryotic homologues thereof, to replicate the damaged DNA by replicating through the site(s) of lesion damage.

The present invention also provides for a hybrid protein that is a fusion between maltose binding protein and UmuC protein and a recombinant DNA molecule encoding such a hybrid protein.

The present invention further provides a method for mutagenesis of a DNA molecule by using UmuC or a functional prokaryotic homologue thereof as a DNA polymerase which is highly mutagenic during in vitro gap-filling replication.

BRIEF DESCRIPTION OF THE DRAWINGS

In FIG. 3A, lane 1 contains markers for unreplicated DNA (15-mer) and fully replicated DNA (43-mer). They were obtained by restriction of nonreplicated plasmid or by $^{32}$P-end labeling of a synthetic 43-mer with the corresponding DNA sequence, respectively. Lane 11 contains the marker for fully replicated products (43-mer). In FIG. 3B, open bars, total translesion replication; closed bars, full translesion replication, represented by the 43-mer only.

In FIG. 4A, lane 2 contains UmuD instead of UmuD'; lane 3, the MBP tag was added instead of the fusion MBP-UmuC protein. Lanes 6 and 7, and 8 and 9 contain side-by-side reactions carried out with substances GP21 and GP31, respectively. In FIG. 4B, lanes 1 and 10 contain markers for the fully replicated DNA (a synthetic 43-mer). Open bars, total translesion replication; closed bars, full translesion replication, represented by the 43-mer only.

In FIG. 5A, the M lanes show size markers for unreplicated DNA (15-mer; right M lane) and for completely replicated DNA (left M lane). In FIG. 5B, open circles, translesion replication with polIII holoenzyme alone; closed circles, translesion replication with polIII holoenzyme, SSB, RecA, UmuD', and the fusion UmuC protein (M-UmuC).

In FIG. 7A, the constitutive bypass involves misalignment of the lesion, resulting in skipping by the polymerase across the lesion, and the formation of a −1 deletion is presented. This is a drastic mutation, which usually leads to inactivation of genes. Under SOS stress conditions, translesion replication occurs without skipping, resulting in insertion of a nucleotide opposite the lesion. This base substitution is usually a tolerable type of mutation. The DNA sequence is from the gap lesion plasmid GP21. In FIG. 7B, a minor bypass pathway without deletion in the absence of SOS induction is presented. After copying the nucleotide past the lesion in the misaligned state, the lesion realigns, and replication proceeds. This leads to complete translesion replication, with the nucleotide present opposite the lesion being complementary to the nucleotide past the lesion.

FIG. 8 shows the phosphorimage of the replication products obtained by UmuD', RecA and SSB in the presence of UmuC or DNA polymerase II, alone or in combination. The time points are 5, 10, and 15 minutes per set of three lanes 2–4, 5–7, and 8–10.

In FIG. 9A, DNA sequence (SEQ ID NOS: 1 and 2) in the vicinity of the site-specific synthetic abasic site in gapped plasmid GP21 is shown. The asterisk marks an internal radiolabeled phosphate on SEQ ID NO:2; The cleavage sites of restriction nucleases Asp700 (XmnI), BstXI, and MspA1I are indicated. The reaction products obtained after cleavage with restriction nucleases Asp700 and MspA1I were 19, 29 and 47 nucleotides long, for the unextended primer, the product arrested at the lesion, and the bypass product, respectively (shown underneath the sequence). The abbreviation nt is for nucleotides. In FIG. 9B, a time course of translesion replication was performed as described in Example 2 herein with 10 or 50 nM MBP-UmuC, as indicated. DNA polymerase I in the control reactions was 90 nM. The reaction products were restricted with Asp700 and MspA1I, followed by urea-PAGE fractionation and phosphorimage analysis. M-UmuC is the MBP-UmuC fusion protein. Lane 14 contains a $^{32}$P-labeled 47-mer marker oligonucleotide, representing the expected bypass product.

FIG. 12 shows a phosphorimage of a urea-PAGE fractionation of products to investigate whether or not the addition of DNA polymerase III core stimulates lesion bypass by MBP-UmuC in the presence of UmuD', RecA and SSB. The translesion replication assay was performed as described under Experimental Procedures in Example 2, with 220 nM MBP-UmuC, and the indicated concentrations of pol III core. Reactions were performed for 8 min at 37° C. Reaction products were restricted with Asp700 and MspA1I, followed urea-PAGE fractionation and phosphorimaging. Lane 5 contains a $^{32}$P-labeled 47-mer marker oligonucleotide, representing the expected bypass product.

FIG. 14 shows a phosphorimage demonstrating that the UmuC($\Delta$26C) protein is defective in lesion bypass but not in DNA synthesis. The translesion replication reactions were preformed as described under Experimental Procedures in Example 2 with 160 nM MBP-UmuC or MBP-UmuC ($\Delta$26C), in the presence of UmuD', RecA and SSB. The reactions were incubated for 2, 4, 8, 10 and 15 min at 37° C., after which the reaction products were restricted with Asp700 and MspA1I, followed by urea-PAGE fractionation and phosphorimaging. Lane 12 contains a $^{32}$P-labeled 47-mer marker oligonucleotide of the expected bypass product.

FIG. 15 shows a phosphorimage of translesion replication assays as performed in FIG. 14, except that the reactions were performed also with MBP-UmuC or MBP-UmuC ($\Delta$26C) alone (160 nM each). The reactions in the presence of UmuD', RecA and SSB were preformed with either 25 nM or 160 nM MBP-UmuC or MBP-UmuC($\Delta$26C). Reactions were carried out for 8 min at 37° C. Lane 8 contains a $^{32}$P-labeled 47-mer marker oligonucleotide of the expected bypass product.

Reaction products were restricted with Asp700 and MspA1I, followed by urea-PAGE fractionation and phosphorimaging.

Figure 17:
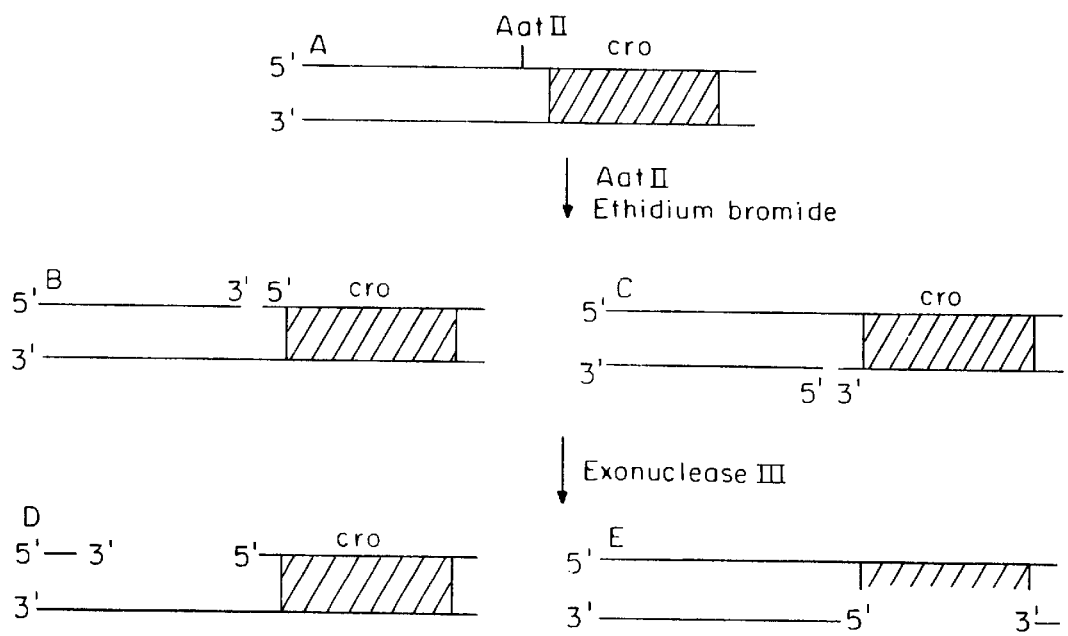

FIG. 17 shows a schematic diagram of the preparation of the gapped plasmid pOC2. Plasmid pOC2 (A) was nicked upstream of the cro gene with restriction enzyme AatII in the presence of ethidium bromide. This generated two subpopulations of nicked plasmids (B) and (C). Addition of exonuclease III extended the nicks into gaps in the 3'→5' direction. Half of the molecules contain the cro gene in the single-stranded region.

Figure 18:
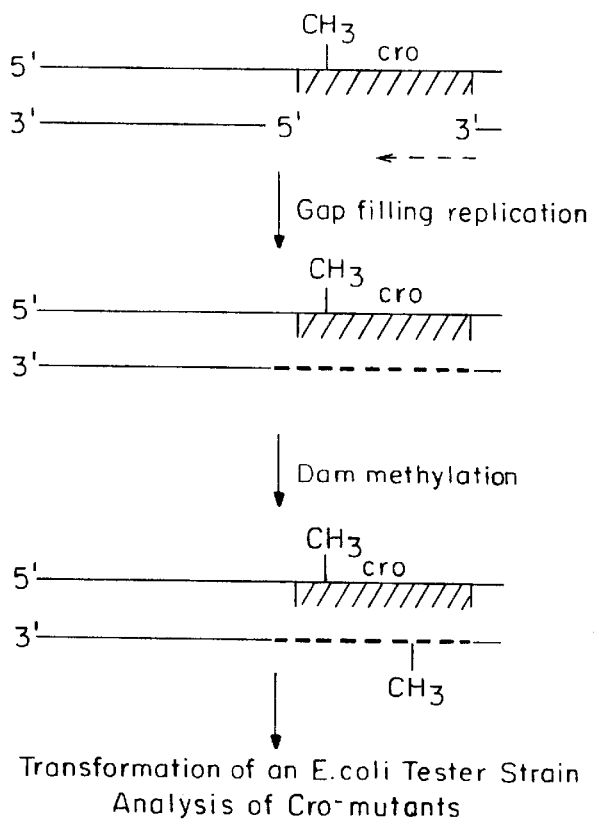

FIG. 18 shows an schematic outline of the cro replication fidelity assay.

Figure 19:
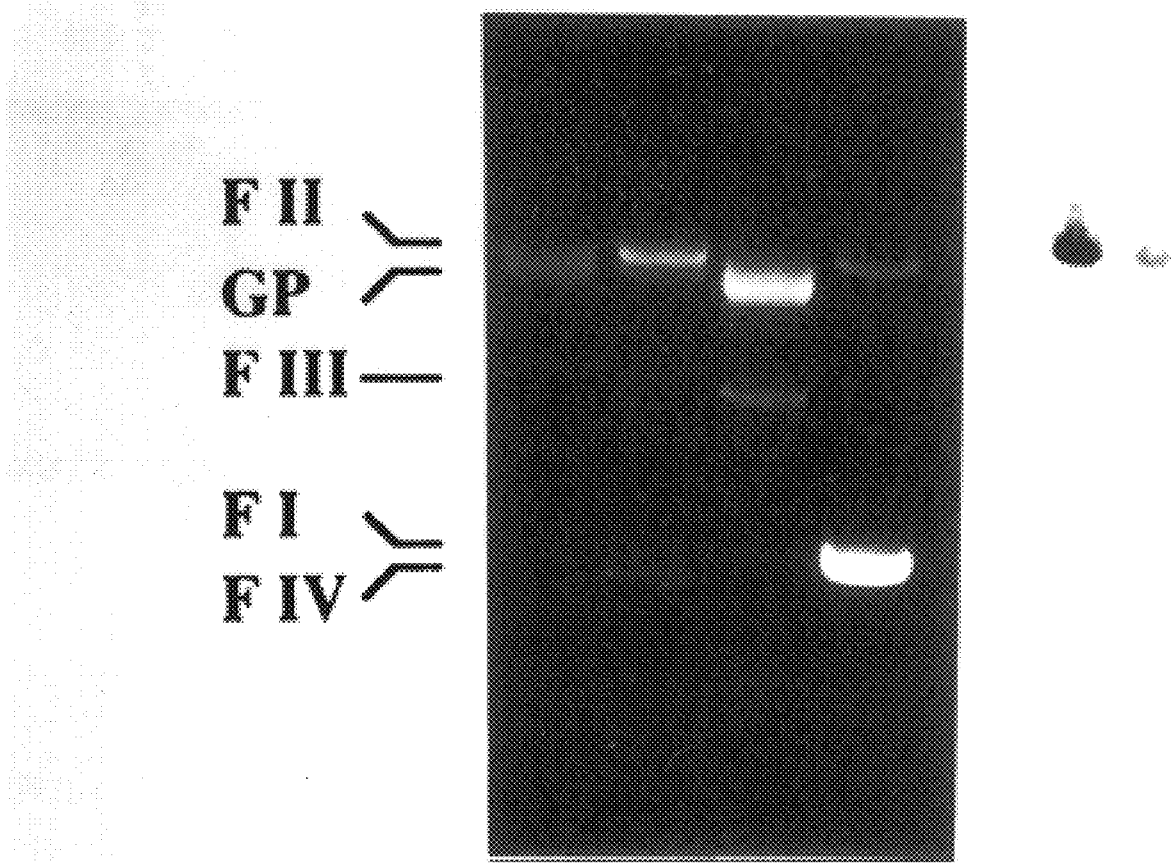

FIG. 19 shows ethidium bromide staining (left panel) and phosphorimaging (right panel) of the reaction products of gap-filling DNA replication by pol V (UmuC) and pol III holoenzyme fractionated by agarose gel electrophoresis. Gap-filling replication was performed with pol V (MBP-UmuC) in the presence of UmuD', RecA, and SSB, or with pol III holoenzyme, by using gapped pOC2 as a substrate. Reactions were performed in parallel in the presence and the absence of radiolabeled dTTP at 37° C. for 20 min. The abbreviations used are: FI, supercoiled plasmid; FII, open, circular plasmid; FIII, linearized plasmid; FIV, covalently closed and relaxed plasmid; GP, gapped plasmid.

Figure 20:
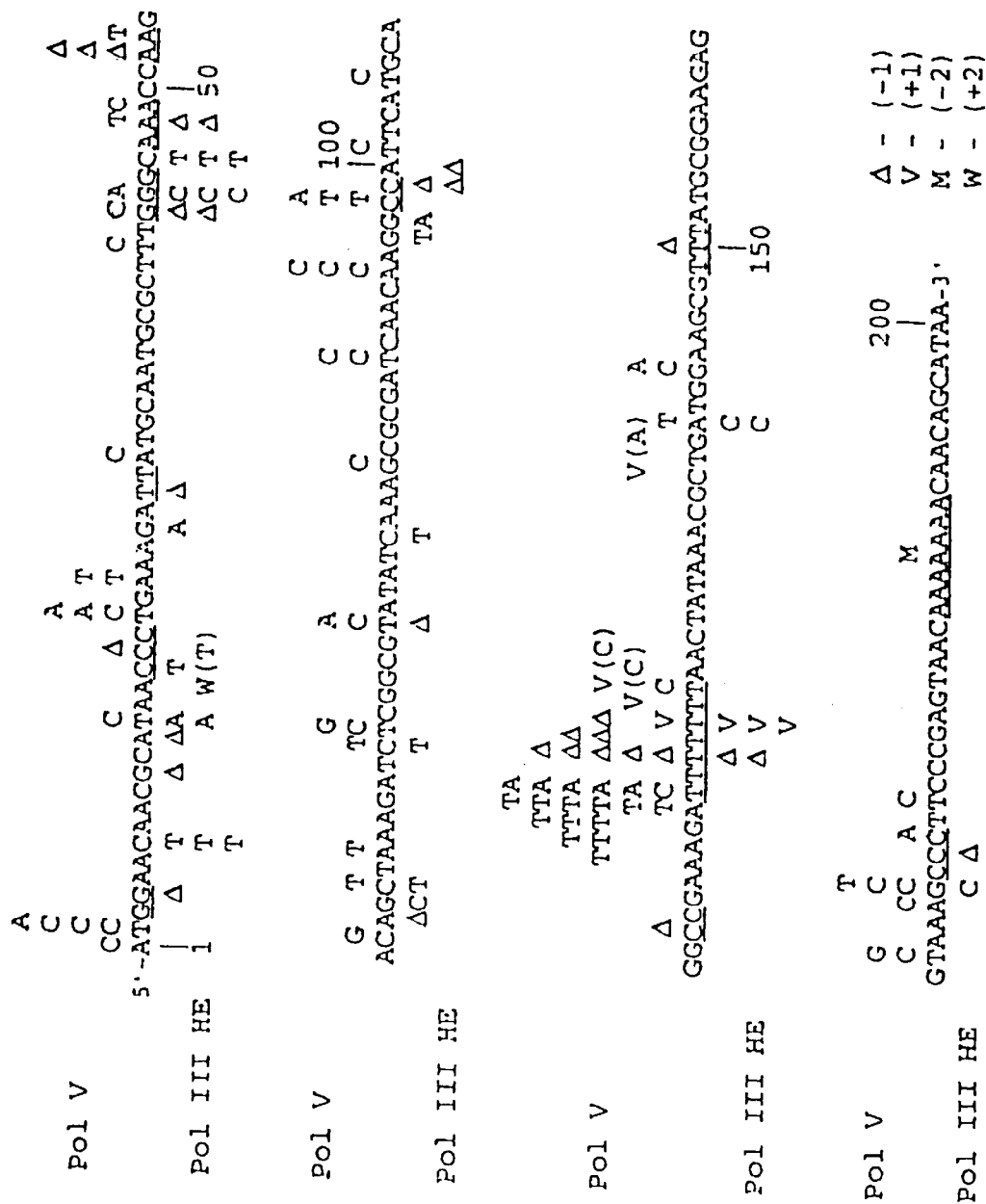

FIG. 20 shows the spectra of mutations generated in the cro gene during in vitro replication by pol V or by pol III holoenzyme. The 201 nucleotides of the coding region of cro are shown. Mutations generated by pol V are shown above the cro sequence, whereas mutations generated by pol III holoenzyme are shown underneath the sequence. Δ, −1 deletion; M, −2 deletion; V, +1 insertion next to the marked nucleotide. The identity of the inserted nucleotide is shown in parentheses, unless it is identical to the template nucleotide after which it was inserted. W, −2 insertion. In addition to mutations in the coding region, eight mutations were found upstream to cro: for pol V, two C→A and one each of T→G, T→A, C→T, +T; for pol III holoenzyme, C→T and G→T, one each.

Figure 21:
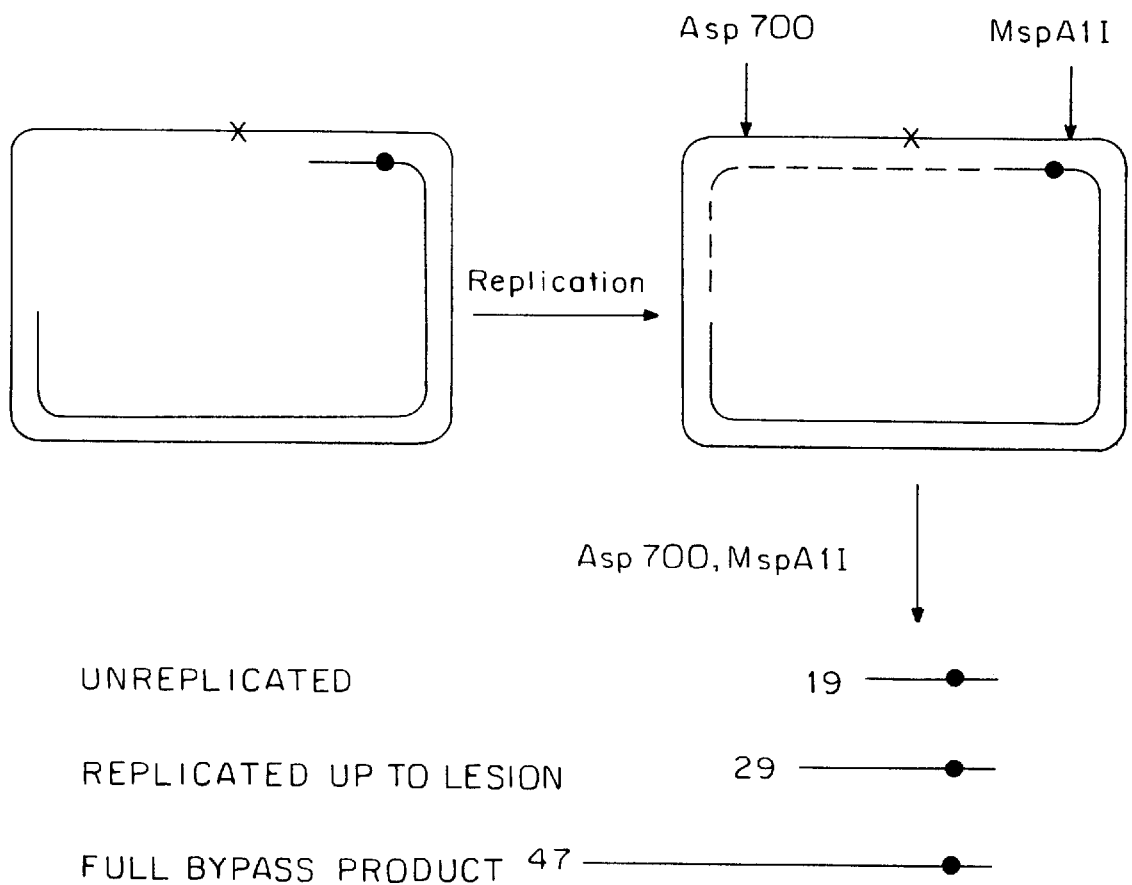

FIG. 21 is a schematic outline of the translesion replication assay. The X marks the site-specific synthetic abasic site, and the black circle represents the internal radiolabeled phosphate.

FIGS. 22A and 22B show the phosphorimage of the gel analysis on the effects of RecA, SSB, and MucA' on translesion replication by MucB (FIG. 22A) or polII (FIG. 22B). In FIG. 22A, DNA polymerase activity of MucB gap-filling bypass replication was performed with MucB alone, or in the presence of MucA', RecA and SSB, using the gap-lesion plasmid GP21 as a substrate. Reactions were performed as described under Experimental Procedures in Example 4 at 37° C. for 10 min. When present, pol II was at a concentration of 100 nM. Reaction products were restricted, fractionated by urea-PAGE, and visualized by phosphorimaging. The DNA bands of 19, 29 and 47-nucleotides long represent the unextended primer, the replication product blocked at the abasic site, and the bypass product, respectively. M, size marker for the 47-mer bypass product.

Figure 23A:
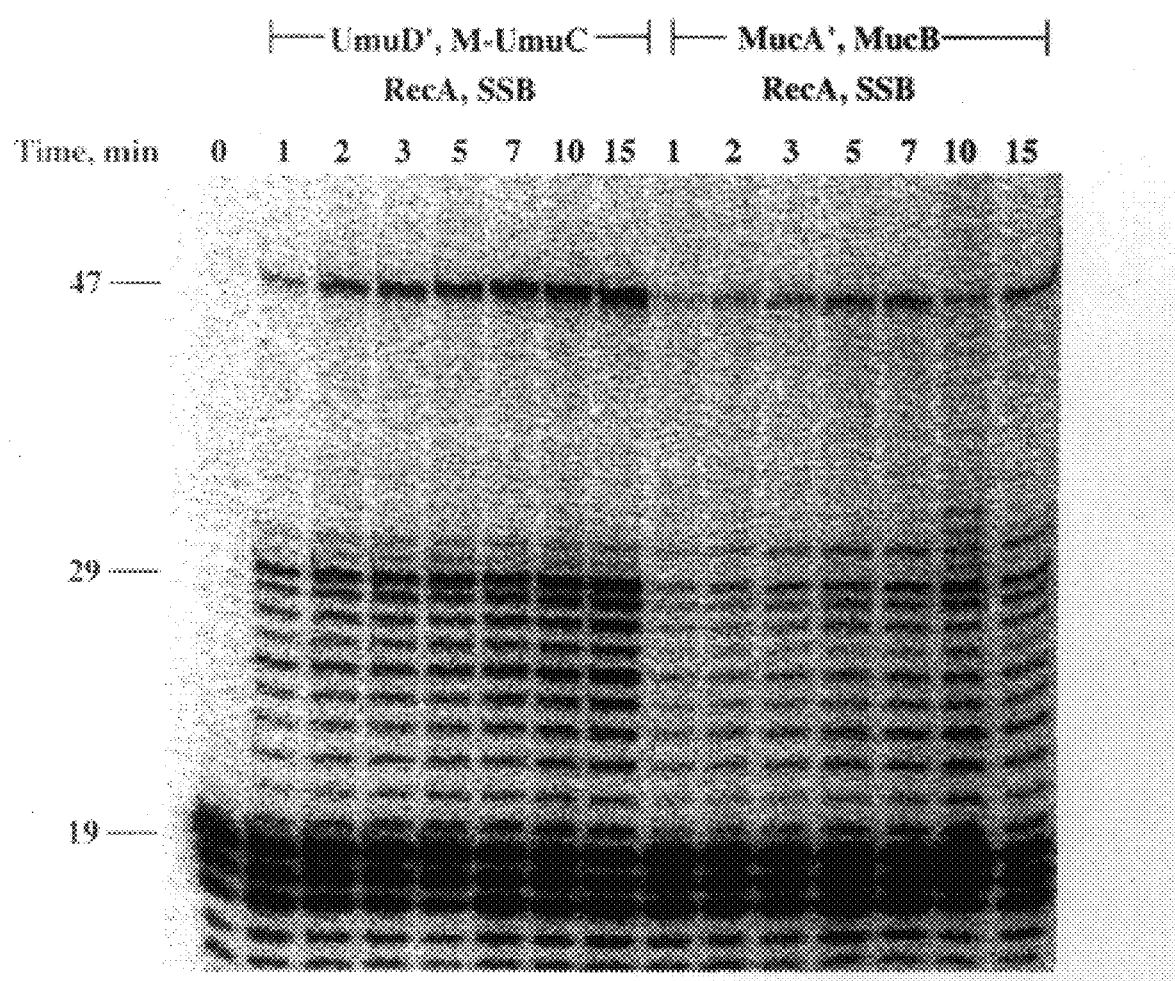
Figure 23B:
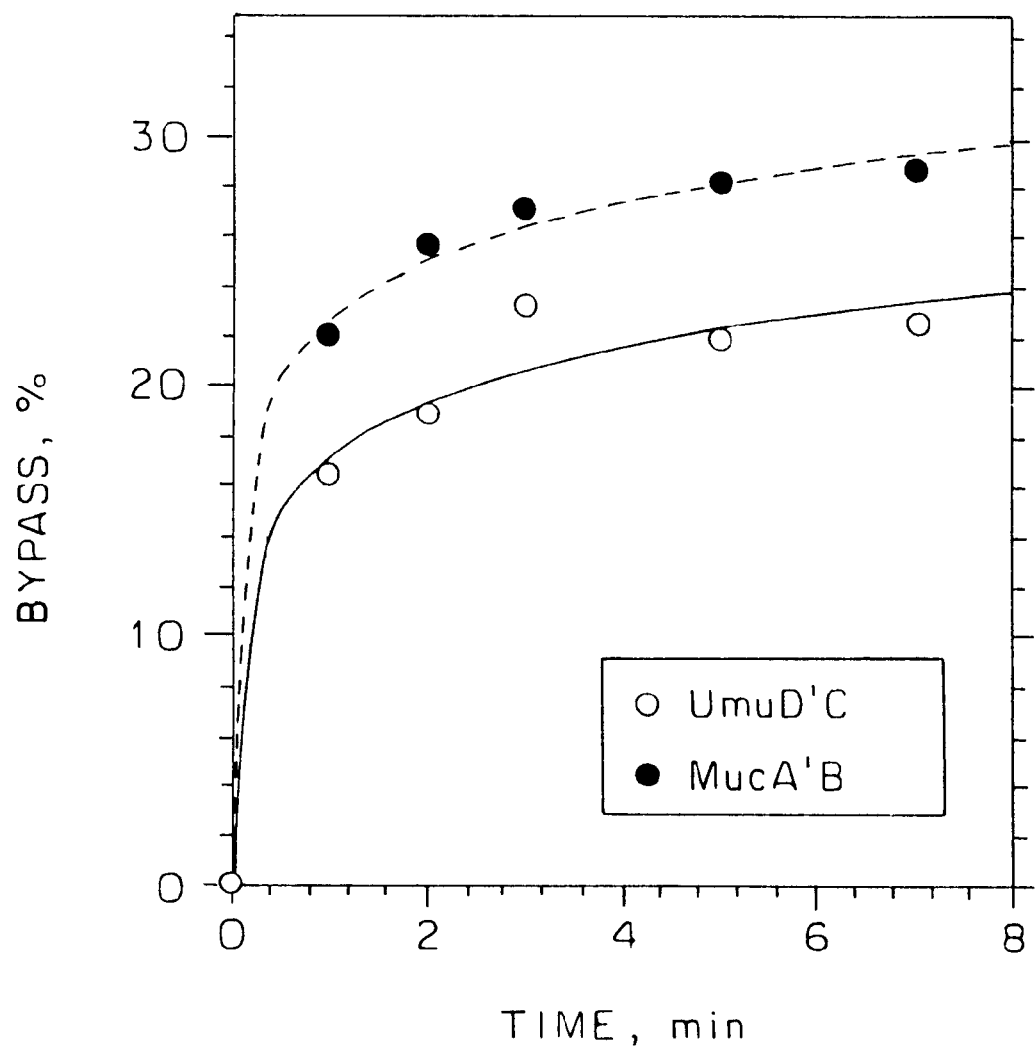

FIGS. 23A and 23B show a phosphorimage (FIG. 23A) and a graph (FIG. 23B) of the kinetics of translesion replication by MucB in the presence of MucA', RecA and SSB. The translesion replication assay was performed as described under Experimental Procedures in Example 4, with 2.5 μM MucA' and 250 nM MucB for the indicated periods of time. In FIG. 23B, the percent lesion bypass is calculated as the total amount of DNA extended beyond the abasic site, divided by the total amount of extended primers.

Figure 24:
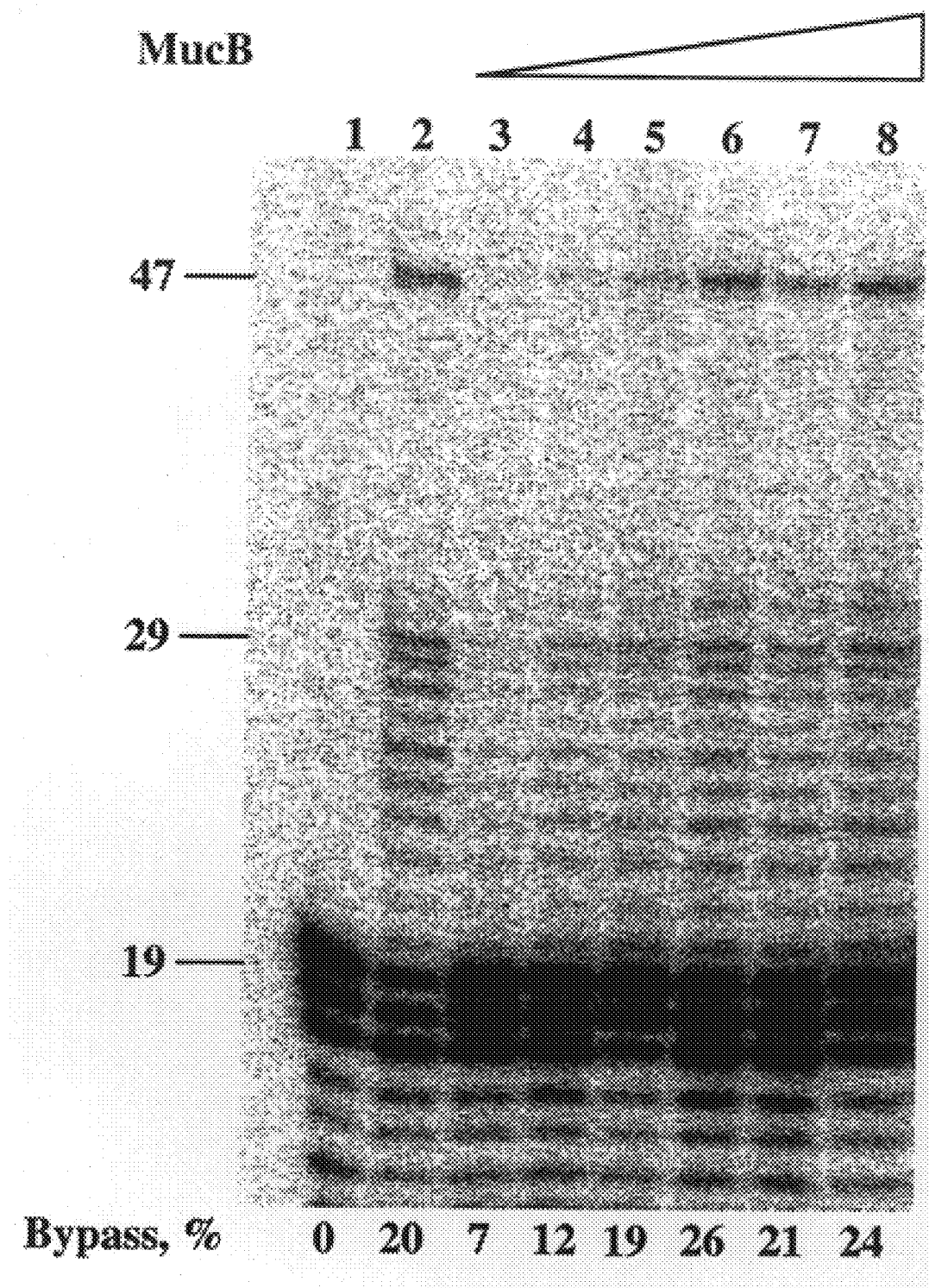

FIG. 24 shows a phosphorimage of the titration of MucB in translesion replication in the presence of MucA', RecA and SSB. The translesion replication assay was performed as described under Experimental Procedures in Example 4, with 2.5 μM MucA', for 5 min. The concentrations of MucB were as follows: Lane 3, 50 nM; lane 4, 100 nM; lane 5, 150 nM; lane 6, 200 nM; lane 7, 250 nM; lane 8, 300 nM. Lane 1 is a control without proteins, whereas lane 2 contains products of a reaction promoted by pol V (250 nM), and UmuD' (2.5 μM) in the presence of RecA and SSB.

Figure 25:
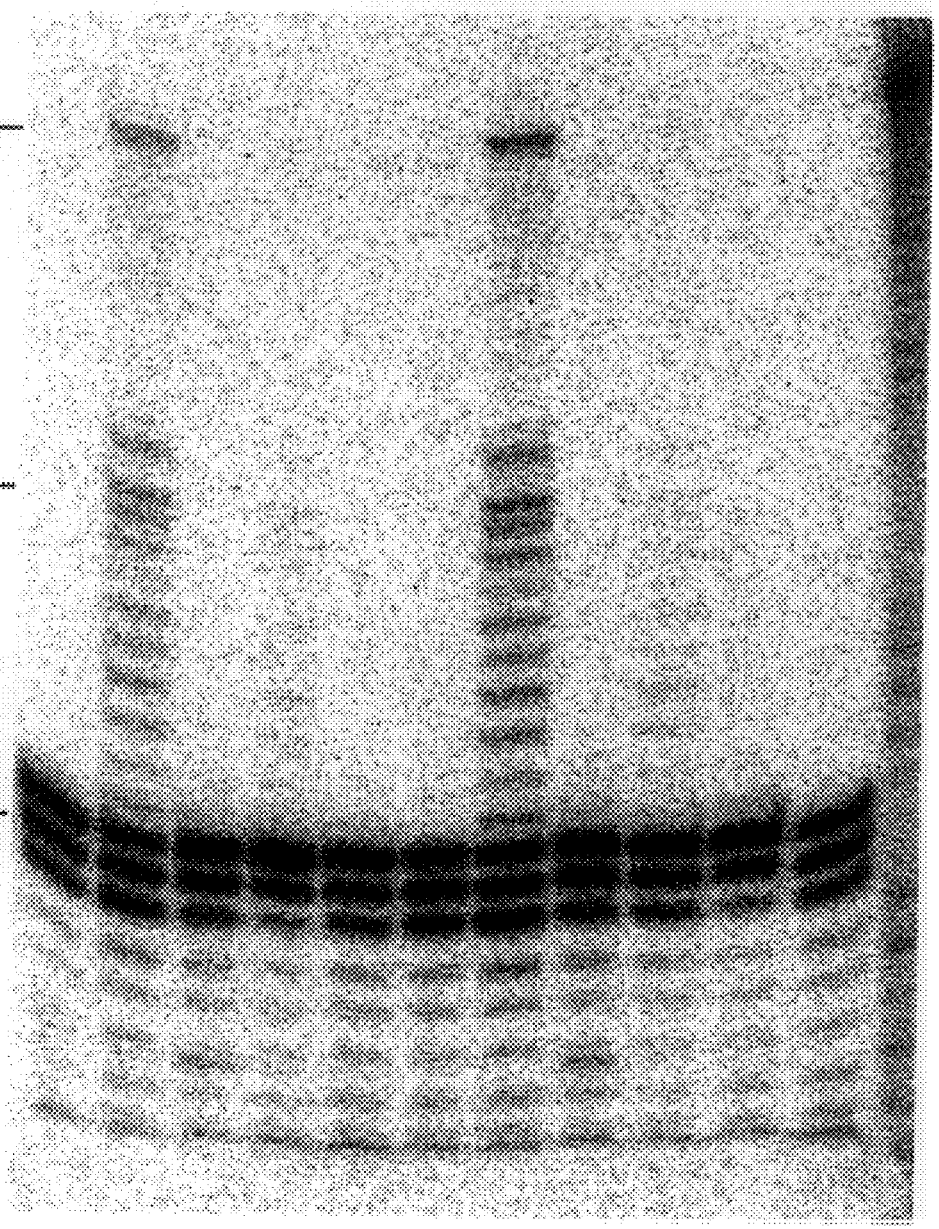

FIG. 25 shows a phosphorimage of the protein requirement of MucB-promoted translesion replication. The translesion replication assay was performed as described under Experimental Procedures in Example 4, with 2.5 μM MucA' and 250 nM MucB, for the indicated periods of time. Parallel reactions were run, in which individual components were omitted, one at a time. M, size marker for the 47-mer bypass product.

Figure 26:
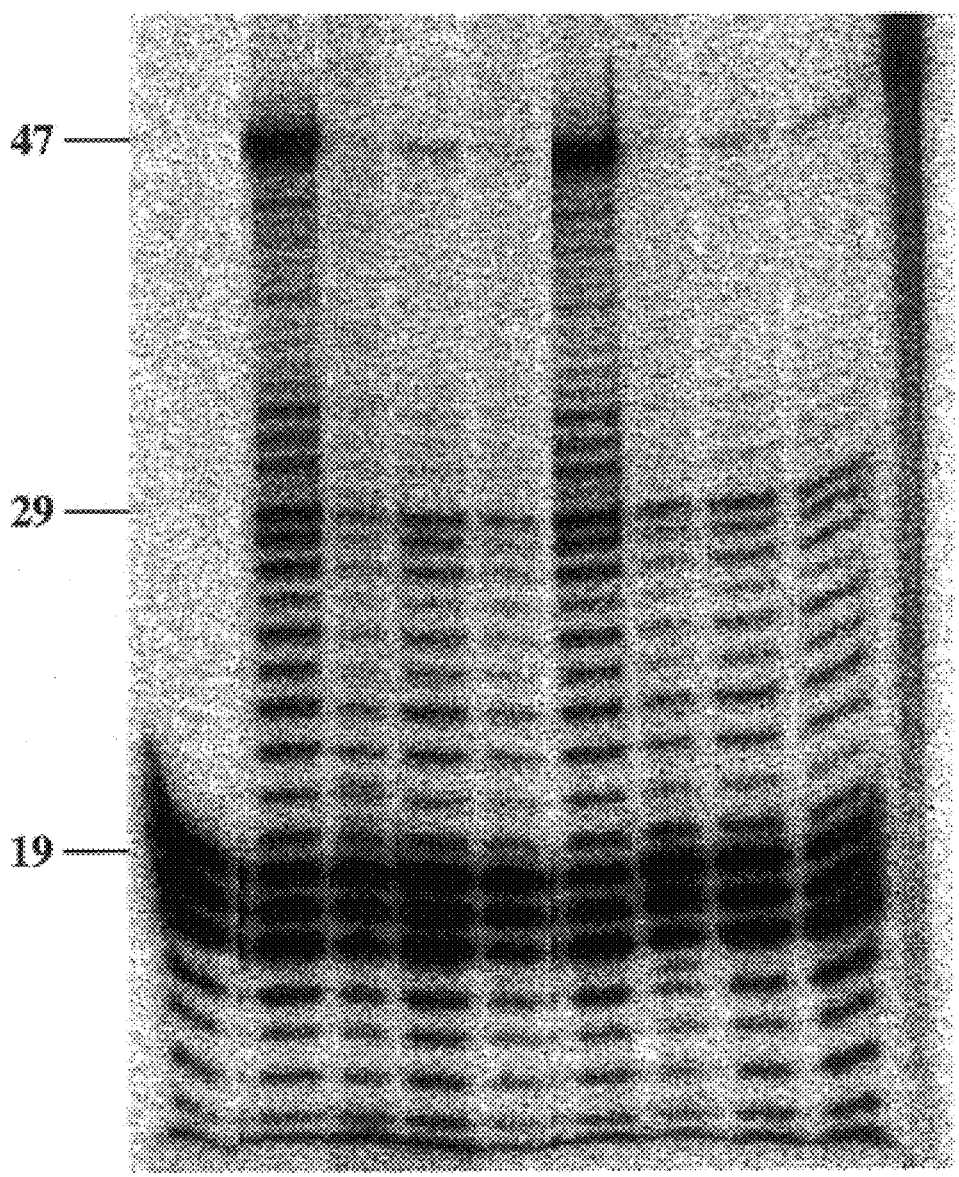

FIG. 26 shows the phosphorimage of a gel demonstrating that MucA cannot substitute for MucA' in MucB-promoted lesion bypass. The translesion replication assay was performed as described under Experimental Procedures in Example 4, for the indicated periods of time, with 250 nM MucB and 4 μM MucA', or the indicated concentrations of MucA. Reaction products were restricted, and analyzed by urea-PAGE followed by phosphorimaging. M, size marker for the 47-mer bypass product.

DETAILED DESCRIPTION OF THE INVENTION

The present invention, which is based partly on the discovery by the present inventors that SOS translesion replication in vitro was reconstituted with purified mutagenesis proteins UmuC and UmuD', DNA polymerase III, RecA, and SSB proteins, and that this reconstituted system was found to be effective in replicating through a blocking lesion (a synthetic abasic site). More significantly, the present invention is based on the further discovery that effective translesion replication is promoted by UmuC, UmuD', RecA and SSB, in the absence of any exogenous DNA polymerase. Thus, the present inventors found that, surprisingly, UmuC is a novel DNA polymerase (designated DNA polymerase V and abbreviated pol V), specialized for translesion replication, which is activated by UmuD' RecA and SSB. In addition to being a lesion-bypass polymerase, UmuC/DNA polymerase V was also found to be highly mutagenic during in vitro gap-filling replication.

One method according to the present invention involves contacting a sample containing damaged DNA molecules, which have one or more sites of DNA lesion damage, with a translesion replication system that includes a mixture of UmuC, as the translesion replication DNA polymerase (no other DNA polymerase is required), UmuD', RecA and SSB proteins, a divalent metal ion, and nucleoside 5'-triphosphates at an appropriate incubation temperature to effect replication of damaged DNA by replicating through one or more sites of DNA lesion damage.

Another method according to the present invention, which is directed to a method for mutagenesis, involves replicating a DNA molecule with a replication system that includes a mixture of UmuC, as the highly mutagenic DNA polymerase, UmuD', RecA and SSB proteins, $Mg^{+2}$ and nucleoside 5'-triphosphates at an appropriate incubation temperature to mutagenize the DNA molecule. UmuC (pol V), in the presence of UmuD', RecA and SSB is highly mutagenic and exhibits a specificity for transversion mutations. These protein requirements and mutagenic specificity suggest that replication of single stranded DNA regions by UmuC/pol V, in the presence of UmuD', RecA, and SSB, is the mechanistic basis of SOS untargeted mutagenesis.

While UmuC from *Escherichia coli* is preferred as the translesion or gap-filling replication DNA polymerase, it will be appreciated by those of skill in the art that a functional fragment/truncated form of UmuC or a functional protein fusion of UmuC with another protein are also suitable as a translesion or gap-filling replication DNA polymerase. A preferred but nonlimiting example of a functional UmuC protein fusion is the maltose binding protein (MBP)-UmuC protein fusion used in the experiments described in Pxamples 1, 2 and 3, which comprises the amino acid sequence of SEQ ID NO:5. A functional fragment of UmuC, such as a truncated form, can be readily obtained by generating a series of staggered deletions from the 5' end, 3' end, or from both ends of a gene encoding UmuC and then cloning and expressing truncated forms of UmuC.

Furthermore, a functional homologue of UmuC or a fragment or fusion protein thereof from *E. coli*, such as dinB (Kim et al., 1997), or from another prokaryotic species, such as, but not limited to UmuC (and UmuD), SamB (and SamA) or impB (and impA) of *Salmonella typhimurium* (Smith et al., 1990; Nohmi et al., 1991; Lodwick et al., 1990), MucB (and MucA' as a UmuD'homologue; Perry et al., 1985) found on native onjugative plasmids in Salmonella strains, rumB (and ruma) of *Proteus rettgeri*, later reclassified as *Providencia rettgeri* (Kulaeva et al., 1995) and dbh of *Sulfolobus solfataricus* (Kulaeva et al., 1996) may be suitably used as long as the UmuC homologue is capable of replicating through DNA lesions with the other protein components of the translesion replication system or is capable of highly mutagenic gap-filling replication of single stranded gaps. Preferably, the prokaryotic homologues of UmuC are used with homologues of UmuD', RecA and SSB proteins from the same species. For example, the preferred translesion or gap-filling replication system protein components are UmuC, UmuD', RecA and SSB from *E. coli*. In another preferred embodiment, the UmuC and UmuD' homologues, MucB and MucA', originally found on a native conjugative plasmid in Salmonella strains but which functions well in *E. coli*, replace UmuC and UmuD', respectively, in the protein component mix with *E. coli* RecA and SSB proteins. This is demonstrated by the experimental results presented in Example 4.

The prokaryotic homologue of UmuC preferably has a sequence identity of at least 50%, and more preferably at least 55%, on alignment with the *E. coli* UmuC of SEQ ID NO:3 (Perry et al., 1985). The amino acid sequence of MucB (SEQ ID NO:27), which is encoded by the nucleotide sequence of SEQ ID NO:26, has approximately 55% homology with UmuC. The term "sequence identity" as used herein means that the amino acid sequences are compared by alignment according to Hanks and Quinn (1991) with a refinement of low homology regions using the Clustal-X-program. Such an amino acid alignment where the identical amino acid residues are indicated (cutoff=50%), and homologous amino acid residues are determined according to the PAM 250 matrix (cutoff=65%).

The Clustal-X program referred to in the previous paragraph is the Windows interface for the ClustalW multiple sequence alignment program (Thompson et al., 1994). The Clustal-X program is available over the internet at ftp://ftp-igbmc.u-strasbg.fr/pub/clustalx/. Of course, it should be understood that if the link becomes inactive, those of ordinary skill in the art can find versions of this program at other links using standard internet search techniques without undue experimentation. Unless otherwise specified, the most recent version of any program referred herein, as of the effective filing date of the present application, is the one which is used in order to practice the present invention.

If the above method for determining "sequence identity" is considered to be nonenabled for any reason, then one may determine sequence identity by the following technique. The sequences are aligned using Version 9 of the Genetic Computing Group's GDAP (global alignment program), using the default (BLOSUM62) matrix (values −4 to +11) with a gap open penalty of −12 (for the first null of a gap) and a gap extension penalty of −4 (per each additional consecutive null in the gap). After alignment, percentage identity is calculated by expressing the number of matches as a percentage of the number of amino acids in the claimed sequence.

The functional prokaryotic homologue of UmuC is intended to encompass a variant of UmuC or of a native prokaryotic homologue found naturally in a prokaryotic organism. When the prokaryotic homologue is an artificially engineered variant (i.e., created by recombinant technology), the sequence identity with UmuC or a native prokaryotic homologue thereof is preferably at least 85%, more preferably 90% and most preferably 95%. However, when the prokaryotic homologue is a variant of UmuC (or MucB), which is mutated to be active in the absence of one or more of the additional required proteins, i.e., UmuD' (or MucA') RecA and SSB, then the level of sequence identity with UmuC (or MucB) may be less than 85% but is still preferably at least 85%, more preferably 90%, and most preferably 95%.

It will be appreciated by those in the art that chemical derivatives of UmuC and of its prokaryotic homologues, in which the amino acid residues are covalently modified with additional chemical moieties not normally part of amino acid residues, are also intended to be encompassed in the present invention. Such modifications may be introduced by reacting targeted amino acid residues with an organic derivatizing agent that is capable of reacting with selected side chains or terminal residues. Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, alpha-bromo-beta-(5-imidazoyl) propionic acid, chloroacetyl phosphate, -alkylmaleimides, 3-nitro-2-pyridyl disulfide, methyl-2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Parabromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2, 4-pentanedione; and transaminase-catalyzed reaction with glyoxylate.

Arginyl residues are modified by reaction with one or several conventional reagents, among them phenylglyoxal, 2,3-butanedione, 1,2-cyclodexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidazole and tetranitromethane are used to form O-acetyl tyrosyl species and 3-nitro derivatives, respectively.

Carboxyl side groups (aspartyl or glutamyl) are selectively modified by reaction with carbodiimides (R'—N—C—N—R') such as 1-cyclohexyl-3-[2-morpholinyl-(4-ethyl)]carbodiimide or 1-ethyl-3-(4-azonia-4,4-dimethlypentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

RecA and SSB homologues in many species of prokaryotes are well-known in the art. When protein components in the translesion or gap-filling replication system have cross-species activity, i.e., capable of translesion or gap-filling replication with one or more protein components from another prokaryotic species, then the equivalent protein components of UmuC, UmuD', RecA and SSB can be any combination of UmuC, UmuD', RecA, SSB, and their functional prokaryotic homologues, as long as that particular combination is capable of translesion or highly mutagenic replication in vitro. The translesion or mutagenic replication of a selected combination can be rapidly and readily determined according to the replication assays described in Examples 1–4.

The method for translesion replication according to the present invention is particularly useful for the amplification of DNA samples which were damaged such as ancient DNA or DNA from blood stains (i.e., for forensic purposes) that were exposed to excessive sunlight or oxidation. Such damaged DNA cannot be amplified by PCR because the polymerase in the PCR reaction gets stuck at a site of DNA damage and cannot continue to replicate past the site of DNA damage. The translesion replication system used in the method according to the present invention overcomes this problem and allows for synthesis/replication of a "good" copy of the DNA from the original damaged DNA ("bad" copy). The "good" copy can then be amplified by PCR. Thus, the present invention can be applied to any application where damaged DNA needs to be copied, restored or amplified.

The nucleoside 5'-triphosphates used in the methods according to the present invention include not only the nucleoside triphosphates commonly found in naturally occurring DNA but also unusual or modified nucleoside triphosphates, which can serve as substrates for DNA synthesis. The active site of DNA polymerases brings together the primer terminus, the DNA template, and the incoming dNTP, and catalyzes the formation of a phosphodiester bond between the primer and the substrate nucleotide, which is complementary to the template base (Kornberg et al., 1991). The great accuracy of this process is attributed, primarily, to a tight geometrical fit of the components in the active site, stabilized by interactions with surrounding amino acids (Kornberg et al., 1991; Joyce et al., 1987; Echols et al., 1991 and Pelletier et al., 1996). Most 'classical' DNA polymerases are blocked by template lesions which cause local distortions in the DNA (Strauss et al., 1985 and Livneh et al., 1993). This is usually explained by the strict geometrical and interaction requirements in the active site of the DNA polymerase, which ensure the high fidelity of DNA synthesis.

The fact that pol V (UmuC) and pol RI (MucB) can replicate through DNA template lesions, that block classical DNA polymerases, suggests a certain degree of flexibility in the active site of these DNA polymerases, at least as far as the DNA template binding is concerned. A flexibility in the active site of the enzyme might be also manifested at the level of the incoming dNTP. This can lead to two consequences: (1) 'Incorrect' dNTPs might be inserted opposite native template nucleotides, leading to a high error frequency during replication in the absence of DNA damage. (2) Modified or unnatural nucleotides might be utilized as substrates by these polymerases. Possibility (1) indeed occurs, at least in the case of pol V, which was shown by the laboratory of the present inventors to form base mismatches at high frequency during replication on undamaged DNA in Example 3 and in Maor-Shoshani et al. (2000). This implies that the pairing requirements are not as strict as for the classical polymerases, and suggest a flexibility not only at the template binding level, but also at the level of incoming dNTP. This means that these DNA polymerases might be able to tolerate and accept as substrates also nucleoside triphosphates which are usually not utilized by DNA polymerases. This possibility can be examined by using the translesion replication assay described in the Examples, and following the incorporation of modified dNTPs into DNA by pol V and by pol RI. Non-limiting examples of suitable modified dNTPs are rNTPs, biotinylated dNTPs, dNTPs modified with fluorescent moieties, and other modifications. The ability to efficiently incorporate modified dNTPs can be useful for labeling and detection of DNA, e.g., for purposes of detection by non-radioactive methods such as antibodies or fluorescence.

Most, if not all DNA polymerases require $Mg^{+2}$ ions for activity (1), and the same is true for pol V. Substituting other metal ions for $Mg^{+2}$ usually leads to altered polymerase activity. For example, using of $Mn^{+2}$ instead of $Mg^{+2}$ caused a decrease in the fidelity of DNA synthesis (Loeb et al., 1982 and El-Deiry et al., 1984), and increased lesion bypass (Larson et al., 1987 and Michaels et al., 1987). Metal ions can thus be used to alter the properties of pol V and pol RI, such that their ability to bypass lesions, to incorporate unusual nucleotides, or to miscode during replication is enhanced, as can be examined using the assay systems presented in the Examples, by using metal ions other than $Mg^{+2}$, e.g., $Mn^{+2}$, $Co^{+2}$, $Ni^{+2}$, $Zn^{+2}$, $Fe^{+2}$ etc. Accordingly, the divalent metal ion which is used in the method according to the present invention can be any of a number suitable divalent metal ion, such as $Mg^{+2}$, $Mn^{+2}$, $Zn^{+2}$, $Co^{+2}$, $Ni^{+2}$, $Fe^{+2}$ etc.

The method for highly mutagenic replication of DNA according to the present invention can be used in an in vitro mutagenesis protocol to mutagenize regions in DNA by replication. Essentially any type of DNA molecule can be used. For instance, single stranded DNA can be used after annealing a primer to it and double stranded DNA can be used after denaturation to single stranded DNA, followed by annealing to a primer.

Another aspect of the present invention is directed to a hybrid protein formed from a fusion of maltose binding protein (MBP) and UmuC protein for use in the method according to the present invention. This hybrid protein has the properties of being produced in E. coli in a soluble and active form. While the preferred embodiment of the hybrid MBP-UmuC protein includes the amino acid sequence of SEQ ID NO:5, it is well-appreciated by those of skill in the art that such a fusion protein can be modified for use in the method according to the present invention, such as by using a truncated MBP and/or truncated UmuC protein in the fusion.

An additional aspect of the present invention is a recombinant DNA molecule which includes a nucleotide sequence encoding the above hybrid MBP-UmuC protein. This nucleotide sequence is preferably SEQ ID NO:4. When the recombinant DNA molecule further includes a self-replicating vector sequence, it can be used to transform host cells and produce the hybrid MBP-UmuC protein by culturing such transformed host cells and recovering the produced hybrid MBP-UmuC from the culture.

Having now generally described the invention, the same will be more readily understood through reference to the following examples which are provided by way of illustration and is not intended to be limiting of the present invention.

EXAMPLE 1

DNA lesions that have escaped DNA repair are tolerated in E. coli by one of two known mechanisms: recombination, or translesion replication (also termed lesion bypass, synthesis or error-prone repair). Genetic experiments have shown that translesion replication is under regulation of the SOS stress response, and requires the umuD, umuC, recA and dnaE (DNA polymerase III) gene products. The in vitro SOS translesion replication was reconstituted using a gapped plasmid containing a site-specific synthesic abasic site in the single-stranded region, and the following purified E. coli proteins: UmuC (fused to maltose-binding protein), UmuD' (the shorter activated form of UmuD), RecA, SSB and DNA polymerase III holoenzyme. With this system, effective replication through the blocking lesion (a synthetic abasic site) occurred.

EXPERIMENTAL PROCEDURES

Overexpression and purification of UmuD', UmuD, and UmuC fused to MBP. The fragments used for cloning umud', umuD and umuC into the expression vector pMAL-c2 (New England Biolabs, Beverly, Mass.) were prepared by PCR, using plasmid pSE117 as a template (Marsh et al., 1985). The 5' primers used for PCR corresponded to the 5' end of the respective genes as follows: umuC primer, 5'-ATGTTTGCCCTCTGTGATGTAAACGCG-3' (SEQ ID NO:6); umuD primer, 5"-ATGTTGTTTATCAAGCCTGCGGATC-3' (SEQ ID NO:7); umuD primer, 5'-GGCTTTCCTTCACCGGCAGCAG-3' (SEQ ID NO:8). The 3' primers contained an EcoRI site at their 5' end to facilitate cloning and continued with sequences complementary to the 3' end of the genes, including the stop codons as follows: umuC primer, 5'-CCGGAATTCTTTATTTGACCCTCAGTAAATC-3' (SEQ ID NO:9); and umuD/D' primer, 5'-CGGAATTCATCAGCGCATCGCCTTAACG-3' (SEQ ID NO:10).

The PCR products were cut with EcoRI and cloned into pMAL-c2 at the XmnI and EcoRI sites. The expression products from these vectors are fusion proteins with a 42.7 kDa maltose binding protein (MBP) portion at the N-terminus. A cleavage site for Factor Xa protease is situated such that cleavage with this protease liberates the native Umu proteins without adding additional amino acids.

Figure 1:
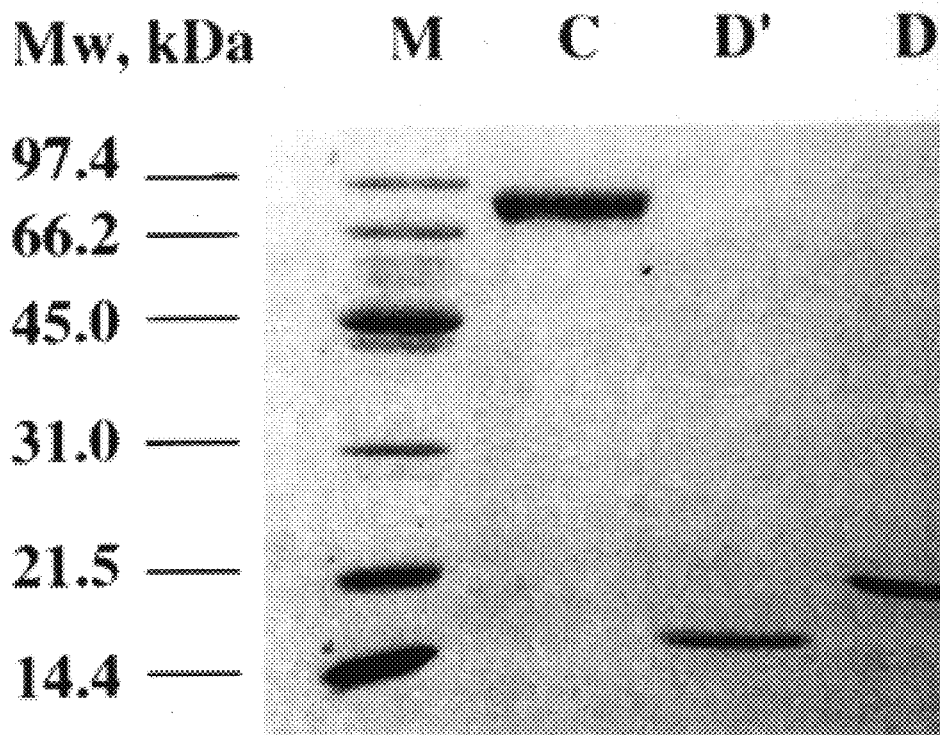
FIG. 1 shows gel electrophoresis analysis of purified Umu proteins, UmuD (D), UmuD' (D'), and MBP-UmuC (C) on 12% PAGE followed by Coomassie-blue staining. M designates the lane of molecular weight markers.

Vectors expressing UmuD or UmuD' were transformed into WBY11, a Δrec ΔumuDC strain. Cells were grown to $OD_{595}$ 0.4–0.6 at 30° C. in LB supplemented with 0.2% glucose. IPTG was added to 0.3 mM, and cells were grown for an additional 3 hr. The cells were harvested, resuspended in buffer A (20 mM Tris-HCL, pH 7.5, 10% glycerol, 200 mM NaCl, 1 mM EDTA, 1 mM DTT), and quick-frozen. The cells were then thawed, sonicated, and centrifuged at 180,000 g for 1 hr at 4° C. The supernatant was loaded on an amylose column, and fusion proteins eluted with buffer A containing 10 mM maltose. The fusion proteins were cleaved with 0.3% (w/w) Factor Xa at 4° C. for 20 hr. For UmuD' purification, the mixture was loaded onto a Sephacel G-75 gel filtration column (to separate residual uncleaved fusion protein), and fractions containing UmuD' were pooled. This step was unnecessary for UmuD purification because cleavage of its fusion protein was complete. The fractions were dialyzed to bring the salt concentration to 80 mM NaCl. The proteins were then loaded on a DEAE SEPHAROSE column, and proteins eluted using a gradient of 80–500 mM NaCl. UmuD eluted at 195 mM NaCl, and UmuD' at 150 mM NaCl. The purity of UmuD and UmuD' was >90%, as judged by Coomassie blue-stained gels (FIG. 1).

Extracts were prepared from cells overexpressing MBP-UmuC as for UmuD, except that a cocktail of protease inhibitors (Sigma, St. Louis, Mo.) was added to the cells before sonication. Cell extract was loaded on a phosphocellulose P-11 column using buffer A. The protein was eluted using a gradient of 0.2–1.0 M NaCl. The fusion protein eluted at 500 mM NaCl. Fractions containing the fusion protein were collected and loaded onto an amylose column. The fusion protein was eluted from the amylose column with buffer A containing 10 mM maltose. The purity of MBP-UmuC was 90%, as judged by Coomassie blue-stained gels (FIG. 1).

Other Proteins

Pol III holoenzyme (Cull et al., 1995), SSB (Lohman et al., 1985), and RecA (Cox et al., 1981) were purified as described, except that a phosphocellulose purification step was added for RecA. Restriction nucleases, T4 DNA ligase, and T4 polynucleotide kinase were from New England Biolabs, Beverly, Mass. T7 gp6 exonuclease was from Amersham Indianapolis, Ind.

DNA Substrates

The preparation of the gapped plasmid carrying a site-specific lesion was recently described (Tomer et al., 1999). In brief, plasmid pSKSL (3361 bp), a derivative of plasmid pBludescript II SK(+), was cleaved with restriction nucleases BstXI and BsaI and ligated to a synthetic gapped duplex oligonucleotide whose termini were complementary to those of the cleaved plasmid. The DNA sequences of the gapped duplexes, which carried a site-specific synthetic abasic site (X), were prepared by annealing the following sequences: gapped duplex GD21, 5'-ACCGCAACGAAGTGATTCCCGTCGTGACTGX GAAAACCCTGGGCTACTTGAACCAGACCG-3' (SEQ ID NO:11), 3'-GTTGCTTCACTAAGG-5' (SEQ ID NO:12), and 3'-CCGATGAACTTGGTC*-5' (SEQ ID NO:13); and gapped duplex GD31, 5'-ACCGCAACGAAGTGATTCCTGGCGTTACCCXA CTTAATCGCGGCTACTTGAACCAGACCG-3' (SEQ ID NO:14), 3'-GTTGCTTCACTAAGG-5' (SEQ ID NO:15), and 3'-CCGATGAACTTGGTC*-5 (SEQ ID NO:16). (The asterisks mark a 5'-$^{32}$P radiolabeled phosphate group, and the XmnI cleavage site is in bold). The desired gapped plasmids, termed GP21 and GP31, respectively, were gel-purified, and the gaps were extended to a size of approximately 350 nucleotides using the T7 gp6 5'-3' exonuclease, as described before (Tomer et al., 1998). Undamaged control plasmids were prepared similarly, except that the oligonucleotides had a G instead of the abasic site. All oligonucleotides were synthesized and purified by the Synthesis Unit of the Biological Services Department at the Weizmann Institute of Science. Oligonucleotides containing the synthetic abasic site analog were synthesized similarly using dSpacer CE phosphoramidite (Glen Research) as a building block. The abasic site analog is a modified tetrahydrofuran moiety, which is a stable analog of 2'-deoxy-ribose in the abasic site. It has a hydrogen instead of a hydroxyl residue on 1' carbon of the deoxyribose ring (Takeshita et al., 1987).

Translesion Replication Assay

The translesion replication reaction mixture (25 $\mu$l) contained 20 mM Tris-HCl (pH 7.5), 8 $\mu$g/ml bovine serum albumin, 5 mM DTT, 0.1 mM EDTA, 4% glycerol, 1 mM ATP, 10 mM MgCl$_2$, 0.5 mM each of dATP, dGTP, dTTP, and dCTP, 0.1 $\mu$g (2 nM) gapped plasmid and 1 nM pol III holoenzyme, 0.6 $\mu$M SSB, 4 $\mu$M RecA, 2.5 $\mu$M UmuD' or UmuD, and 0.23 $\mu$M M-UmuC or MBP. Reactions were carried out at 37° C. for 2–20 min, after which they were terminated by adding SDS to 0.2%, EDTA to 20 mM, and NaCl to 200 mM and heat-inactivated at 65° C. for 10 min. The proteins were digested with 0.4 mg/ml proteinase K at 37° C. for 1 hr, after which the DNA was extracted with phenol-chloroform and ethanol-precipitated. The DNA was digested with XmnI (3 U/tube) at 37° C. for 2 hr. Then, 5 U of BstXI was added, and incubation continued at 55° C. for another 2 hr. The DNA was fractionated by electrophoresis on 15% polyacrylamide gels containing 8 M urea. Gels were run at 1500–2000 V for 2–3 hr, after which they were dried, and visualized and quantified using a Fuji Bas 1000 phosphorimager. The extent of translesion replication was calculated by dividing the amount of bypass product by the amount of extended primer.

DNA Sequence Analysis of Translesion Replication Products

DNA (100 ng) from the translesion replication assay was processed as indicated above, until the XmnI cleavage step. Instead of cleaving with XmnI, the DNA was cut with HindIII (20 U/tube), which cuts the plasmid at a single site 867 bp from the abasic site. DNA was then digested with 2 U of S1 nuclease in a final volume of 32 $\mu$l for 30 min at 30° C. to degrade unextended ssDNA template regions. The reaction was stopped by adding 128 $\mu$l of 25 mM EDTA and heating at 80° C. for 10 min. The mixture was extracted with phenol:chloroform (1:1), then chloroform. Twenty microliters of this DNA sample was linearly amplified in a 50 $\mu$l PCR reaction using 1 U Taq DNA polymerase (Appligene), 200 $\mu$M dNTPs, and 50 pmol of primer #1, containing an EcoRI site at its 5' end, and complementary to the newly synthesized strand. The sequence of primer #1 was 5'-GAGAATTCGCAATGATACCGCCGCAACGAAGTG-3' (SEQ ID NO:17), and its 3' end was 16 nucleotides upstream from the abasic site. The PCR mixture was heated to 95° C. for 1 min, 56° C. for 5 min, and 72° C. for 3 min. This was followed by 39 cycles of denaturation at 95° C. for 1 min, annealing at 56° C. for 2 min, and extension at 72° C. for 3 min. The PCR products were fractionated on a 0.8% low-melting agarose gel, and the 913-nucleotide-long PCR products in gel slices were subjected to a second round of regular PCR. Twenty microliters of melted gel samples containing the DNA was amplified with primer #1 and primer #2, which contains a BamHI site at its 5'. The sequence of primer #2, complementary to nucleotides 466–449 of plasmid pSKSL, was 5'-CGGGATCCGAAGGTGGAGGAAGGTG-3' (SEQ ID NO:18). The PCR program used was the same as above, except that only 35 cycles and 2 min extension times were used. This procedure yielded 273 bp PCR products. A control amplification protocol performed with the gapped plasmid that had not undergone a translesion replication reaction gave no PCR products, indicating that the S1 nuclease treatment was effective in eliminating nonreplicated DNA molecules. The 273 bp PCR products were gel-purified, digested with BamHI and EcoRI, and cloned into pUC18 at those sites. Individual transformants were picked, and their plasmid contents extracted and subjected to automated DNA sequence analysis, performed by the Biological Services Department in the Weizmann Institute of Science. In this procedure, each translesion replication event was scored, and there was no selection for specific mutagenic events.

In Vivo Mutagenesis of Gap Lesion Plasmids

The gap lesion plasmids GP21 or GP31, each carrying a site-specific synthetic abasic site, and the respective control plasmids GP20 or GP30 without a lesion were used to transform competent E. coli AB1157 argE3 hisG4 leuB6 $\Delta$(gpt-proA)62 thr-1 ara-14 galK2 lacY1 mtl-1 xyl-5 thi1 tsx-33 rpsL31 supE44 or its isogenic $\Delta$umuDC derivative, WBY100. For experiments under SOS-induction, the cells were UV-irradiated at 30 Jm$^{-2}$, followed by a 30 min incubation period at 37° C., to allow expression of SOS functions. The cells were then transformed with the gapped plasmids (0.1 $\mu$g) using the Ca-MOPS method (Strike et al., 1979). The "survival" of the plasmid was calculated by dividing the number of transformants obtained with a gap lesion plasmid by that obtained with the control gapped plasmid without the lesion. Cultures were grown from individual colonies, and their plasmid contents extracted and subjected to automated DNA sequence analysis, performed by the Biological Services Department at the Weizmann Institute of Science.

RESULTS

Based on in vivo studies, and on the pioneering study of Rajagopalan et al. (1992), SOS mutagenesis results from a translesion replication reaction that required DNA polymerase III, RecA, UmuD', and UmuC (Livneh et al., 1993; Walker, 1995; Woodgate and Levine, 1996). The major obstacles in the attempts to study the mechanism of SOS mutagenesis using an in vitro reconstituted system were the inability to obtain reproducibly purified and active UmuC (Woodgate et al., 1989) and the difficulty in constructing an appropriate DNA substrate. We have overproduced and purified UmuD, UmuD', and UmuC as soluble proteins fused to a portion of the maltose-binding protein (MBP). Once purified, the MBP tag was removed from the UmuD and UmuD' fusion proteins using factor Xa protease (FIG. 1). The MBP-UmuC protein was found to be resistant to cleavage and was used in subsequent experiments as the fusion protein (FIG. 1). It was found to bind ssDNA (data not shown), consistent with previous reports that UmuC binds ssDNA (Petit et al., 1994; Bruck et al., 1996).

Figure 2:
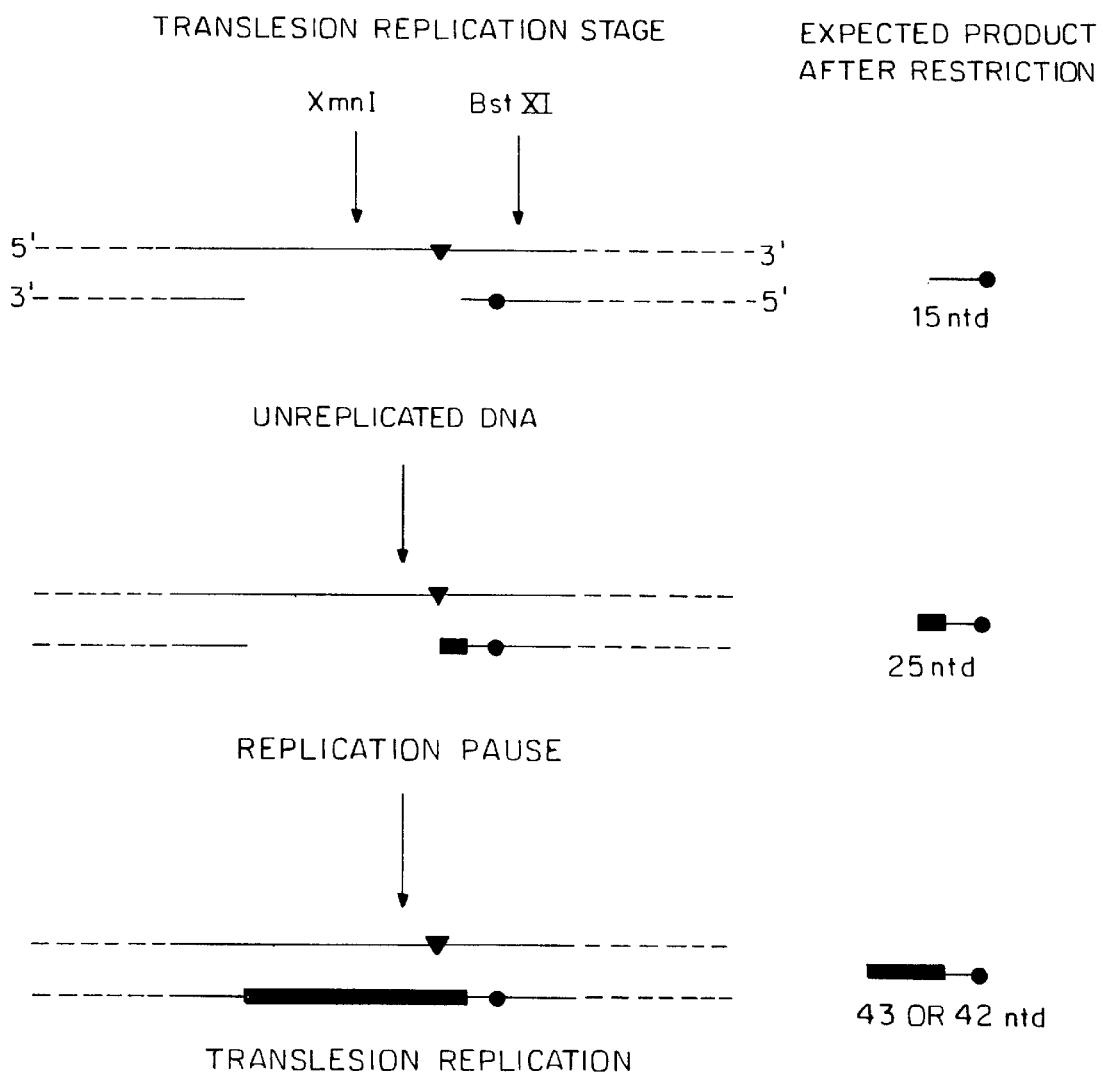
FIG. 2 shows the outline of the translesion replication assay using a gap lesion plasmid. The replication products are shown before (left side) and after (right side) cleavage with restriction nucleases Xmnl and BstXl. Only a portion of the plasmid is shown. The ssDNA gap was approximately 350 nucleotides long, and the primer terminus was located 11 nucleotides upstream of the lesion. Closed triangle, synthetic abasic site; closed circle, radiolabeled phosphate.

A critical component in reconstitution of SOS translesion replication was the DNA substrate used, which consisted of a gapped plasmid carrying a site-specific lesion located within a single-stranded region of 350 nucleotides (FIG. 2).

Such a construct serves as a good substrate for replication by the multisubunit pol III holoenzyme, and for binding by RecA and SSB. A method for the preparation of these gap lesion plasmid was recently developed in the laboratory of the present inventors (Tomer et al., 1999). When a DNA polymerase was added to the substrate, the 3' terminus was extended, and this was monitored by a gel assay, after cleaving the DNA with two restriction nucleases: BstXl, which cleaves just upstream to the interna $^{32}$ P-radiolabel, and Xmnl, which cleaves downstream to the lesion (FIG. 2). This cleavage was introduced in the assay in order to reduce the sizes of radiolabeled replication products, and thus to increase resolution. A synthetic abasic site was used as a model lesion. Abasic sites, which are very common lesions DNA, are known to inhibit DNA replication and give rise to mutations via the UmuD' and UmuC pathway (Loeb et al., 1986).

Figure 3A:
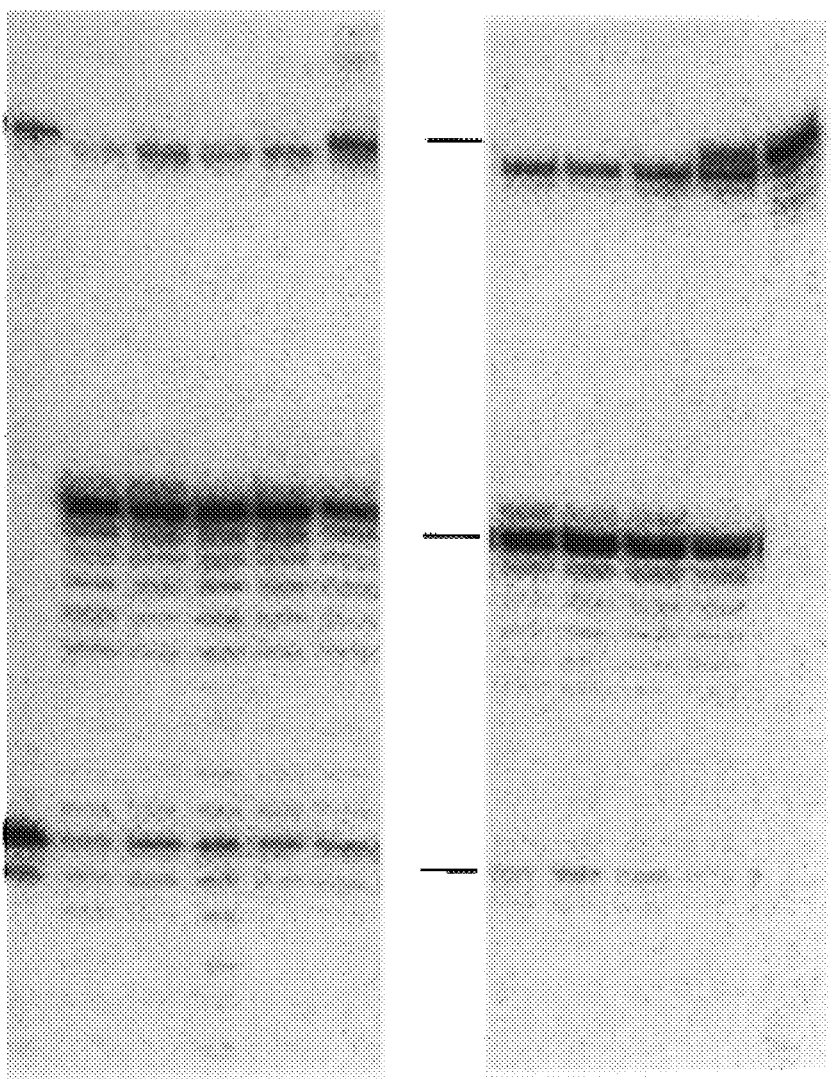
FIG. 3A shows the phosphorimage of the gel analysis on the effects of RecA, SSB, UmuD', and the fusion UmuC protein on translesion replication by DNA polymerase III holoenzyme
Figure 3B:
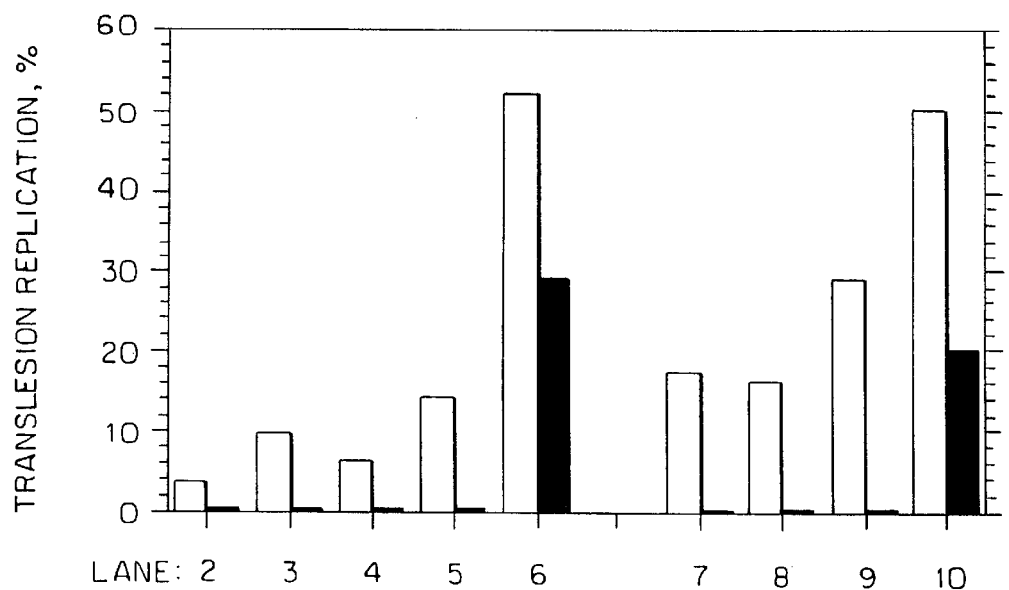
FIG. 3B shows the quantification of the results shown in FIG. 3A. Translesion replication was carried out with polIII holoenzyme and the gap lesion plasmid GP21, in the presence of RecA, SSB, UmuD', and the fusion UmuC protein (M-UmuC) as indicated, at 37° C. for 8 min. The samples were deproteinized, fractionated by urea-PAGE, and visualized and quantified by phosphorimaging. The details are presented in the materials and methods in Example 1.
Figure 4B:
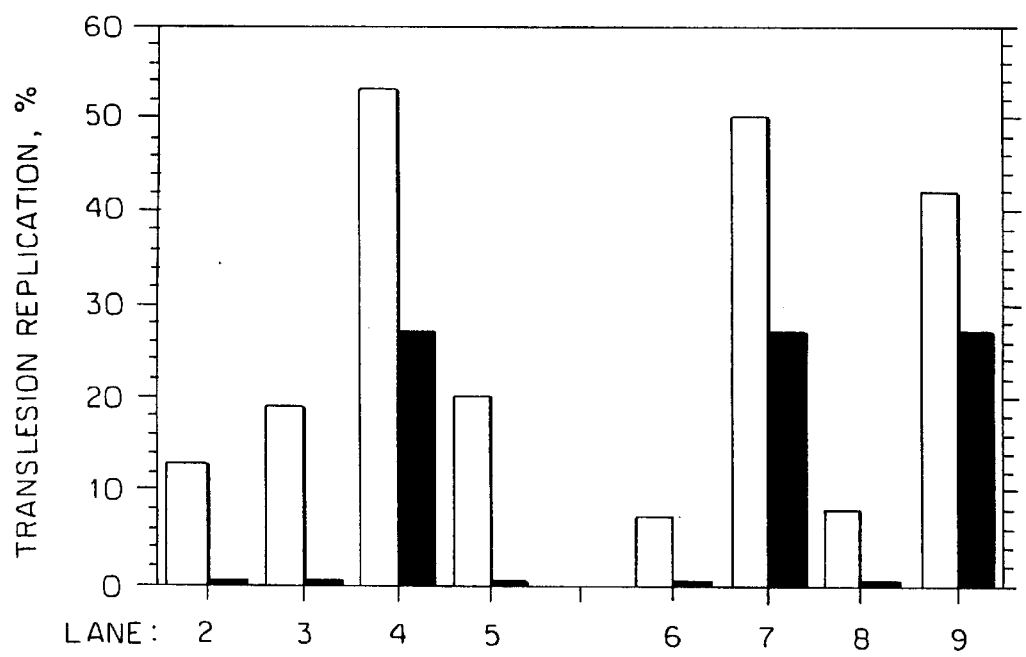
FIG. 4A shows the phosphorimage of the gel analysis of the characteristics of SOS translesion replication and FIG. 4B shows the quantification of the results shown in FIG. 4A. Reactions were carried out as described above in FIGS. 3A and 3B with the proteins and DNA substrates as indicated.
Figure 4A:
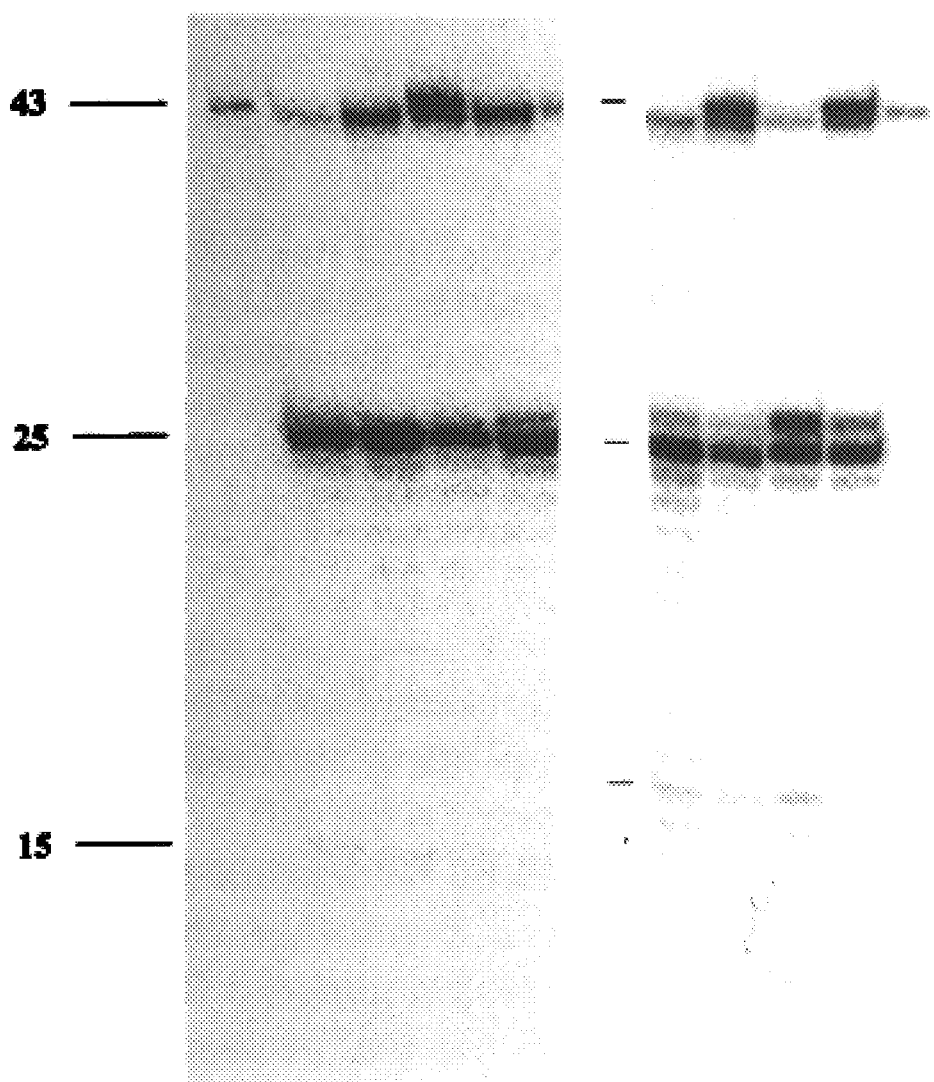

Incubation of the gap lesion plasmid with DNA polymerase III holoenzyme resulted in inhibition of replication at the nucleotide preceding the lesion (25-nucleotide-long product), but translesion replication was also observed (FIG. 3, lane 2). This is consistent with previous results on the ability of pol III holoenzyme to bypass a native or synthetic abasic site, unassisted by other proteins (Hevroni et al., 1999). Addition of RecA led to a 2-to 3-fold increase in translesion replication (FIG. 3, lane 3). This demonstrates that RecA directly stimulates translesion replication. SSB, which melts out secondary structures and was recently found to interact with a UmuC homolog (MucB; Sarov-Blat and Livneh, 1998), also increased translesion replication 2- to 3-fold (FIG. 3, lane 4), consistent with previous results (Livneh, 1986; Tomer et al., 1999). When both RecA and SSB were added, stimulation of translesion replication was only marginally higher than with either of the proteins alone, reaching an effect of 3- to 4-fold over pol III holoenzyme alone (FIGS. 3A and 3B, lanes 5 and 7). When UmuD' and the UmuC fusion protein were added as well, forming a five-protein reaction, there was an additional 3-fold increase in translesion replication, reaching 50%. Most importantly, when all five proteins were present, an additional bypass product, one nucleotide longer was formed (FIG. 3A, lanes 6 and 10). This product was not formed in the absence of either the UmuC fusion proteins, or UmuD' (FIG. 3A, lanes 8 and 9, respectively), nor was it formed when UmuD was used instead of UmuD' (FIG. 4A, lane 2), or when MBP was used instead of the MBP-UmuC fusion protein (FIG. 4A, lane 3). By comparison to the migration of a DNA size marker, the longer product was found to be 43 nucleotides long, representing the full-length translesion replication product. The shorter, 42-nucleotide-long band was formed when the polymerase skipped over the lesion, that it, did not incorporate a nucleotide opposite the synthetic abasic site during the gap-filling replication (see also FIG. 7A).

Figure 5A:
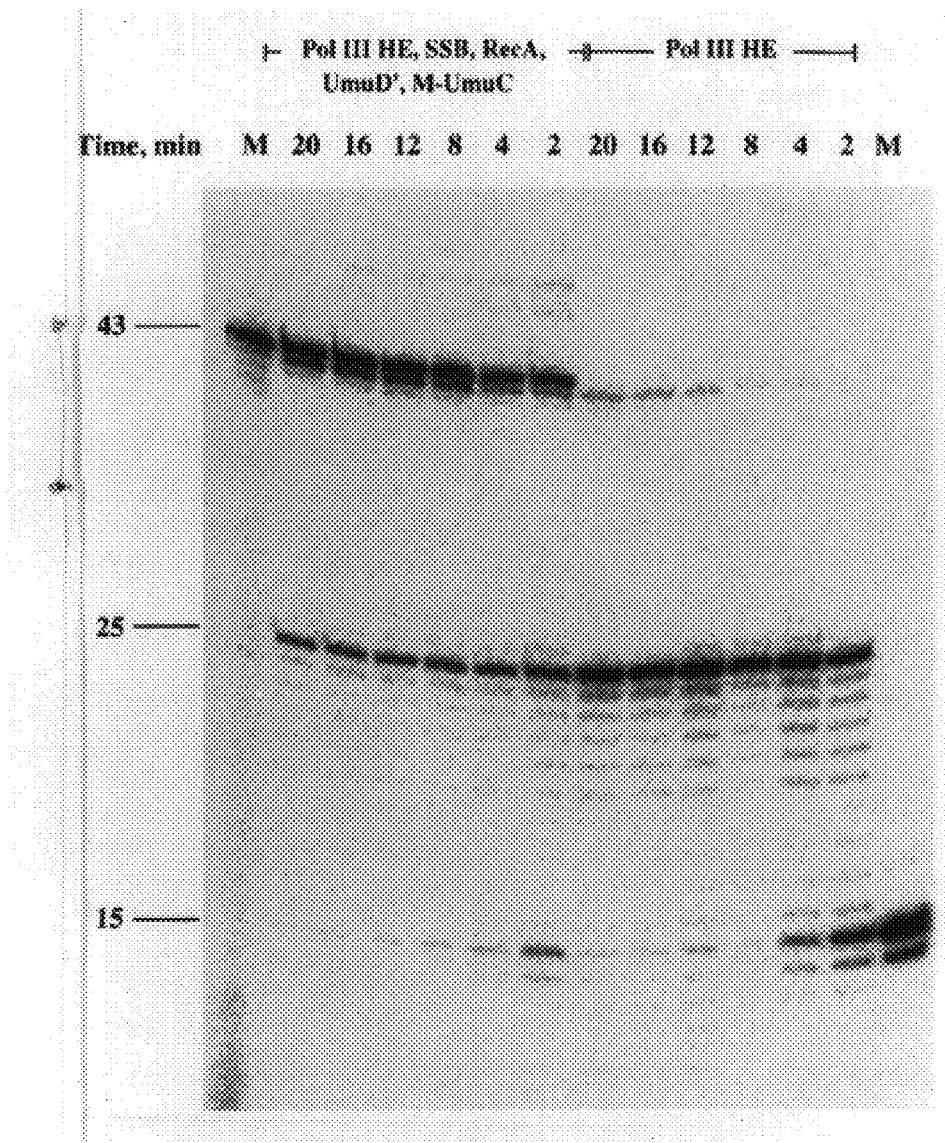
FIG. 5A shows the phosphorimage of the gel analysis of the time course of in vitro reconstituted SOS translesion replication and Figure 5B shows the quantification of the results shown in FIG. 5A. Translesion replication of substrate GP21 was carried out with polIII holoenzyme alone, or in the presence of SSB, RecA, UmuD', and M-UmuC for the indicated time periods. The details are presented in the materials and methods section of Example 1.
Figure 5B:
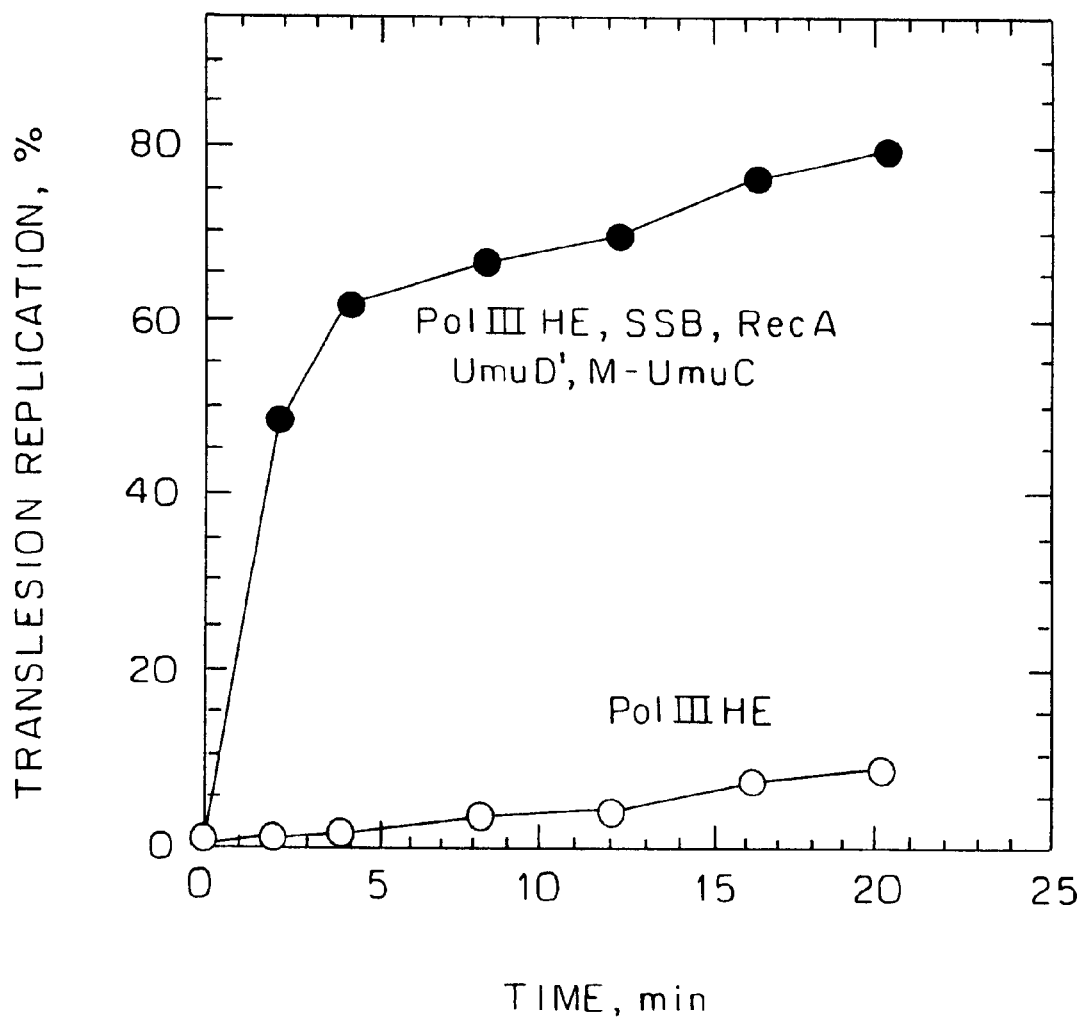

To determine whether the reconstituted translesion replication reaction occurs in another DNA sequence context, the gap lesion plasmid GP31, in which the sequence surrounding the lesion was changed, was used. As can be seen in FIGS. 4A and 4B (lanes 6–10), similar results were obtained with the two substrates. Addition of SSB, RecA, UmuD', and the UmuC fusion protein stimulated replication by pol III holoenzyme through the lesion on both substrates, and a 43-nucleotide band, not observed with pol III holoenzyme alone, was formed (FIG. 4A, lanes 6–10). A time course of translesion replication with pol III alone or with the addition of SSB, RecA, UmuD', and the UmuC fusion protein is shown in FIGS. 5A and 5B. As can be seen, the reconstituted system is robust and performs highly effective translesion replication leading to 70% bypass in 12 min. The major bypass product is 43 nucleotides long, representing full replication, without skipping over the lesion.

In order to establish the replication specificity across the synthetic abasic site, we have amplified the replication products using PCR and determined the DNA sequence at the site of the lesion. The results of these experiments are shown in Table 1.

TABLE 1

Analysis of Mutations Formed during
In Vitro Translesion Replication

| Mutation Type | Translesion Replication Reaction Components Pol III HE | Pol III HE, SSB, RecA UmuD', M-UmuC |
|---|---|---|
| Base substitution | | |
| A | — | 11 |
| G | — | 5 |
| T | — | 1 |
| C | — | — |
| Total base substitutions | — (0%) | 17 (<u>63%</u>) |
| Deletions | | |
| −1 | 22 (<u>85%</u>) | 10 |
| −2 | 3 | — |
| −3 | 1 | — |
| Total deletions | 26 (<u>100%</u>) | 10 (37%) |
| Total mutants analyzed | | 27 |

Translesion replication of substrate GP21 was carried out in the presence of the indicated proteins, after which the newly synthesized strand was amplified, cloned into plasmid pUC18, and introduced into *E. coli* cells. The table shows the DNA sequence opposite the lesion obtained for individual clones. The details are presented under Experimental Procedures. The values in parentheses represent the percentage of the particular mutation type. The most abundant type of mutation is underlined.

All of the 26 isolates obtained during replication by pol III holoenzyme alone contained small deletions at the site corresponding to the lesion in the original substrate. Of the 26 mutants, 22 were one-nucleotide deletions (85%). No base substitutions were observed. Thus, although pol III holoenzyme can replicate through the synthetic abasic site, it does so by skipping the lesion. DNA sequence analysis of bypass products synthesized in the fully reconstituted system revealed that in this case, too, all mutations were targeted to the lesion. However, a dramatic change was observed in mutation type. The majority of mutations were now base substitutions (63%), implying insertion of a nucleotide opposite the lesion during the translesion replication reaction. Most base substitutions has an A inserted opposite the abasic site, in agreement with in vivo results on the mutagenic specificity of abasic sites (Kunkel, 1984; Lawrence et al., 1990). These results confirm the identity of the 42- and 43-nucleotide-long DNA products seen in the gel assay as representing a one-nucleotide deletion and full-length bypass product, respectively. In addition, they reveal a function of the SOS-induced proteins, as anti-deletion agents.

Previous in vivo studies have established that under SOS conditions abasic sites cause primarily base substitutions, with insertion of a dAMP residue being the major event (Kunkel, 1984; Lawrence et al., 1990). However, in these studies mutational specificity was not examined in noninduced cells or in the absence of the Umu proteins. The gap lesion plasmids used in the in vitro experiments were utilized in order to examine the in vivo mutagenicity of the synthetic abasic site. The experimental protocol involved transformation of uninduced or SOS-induced cells with gap lesion plasmids that were not subjected to any treatment. The plasmids can be maintained in the host cells only after the gap is repaired in vivo. In the absence of a homologous double-stranded DNA, the only known mechanism to repair the gap is translesion replication. Thus, the number of transformants obtained is a reflection of the efficiency of in vivo translesion replication operating on the plasmid. The survival of a gapped plasmid carrying a lesion is defined by the efficiency in which it transforms a particular *E. coli* strain, compared to a gapped plasmid without a lesion. Plasmids were isolated from cultures of transformed cells, and the DNA sequence in the region that originally carried the lesion was determined.

Figure 6A:
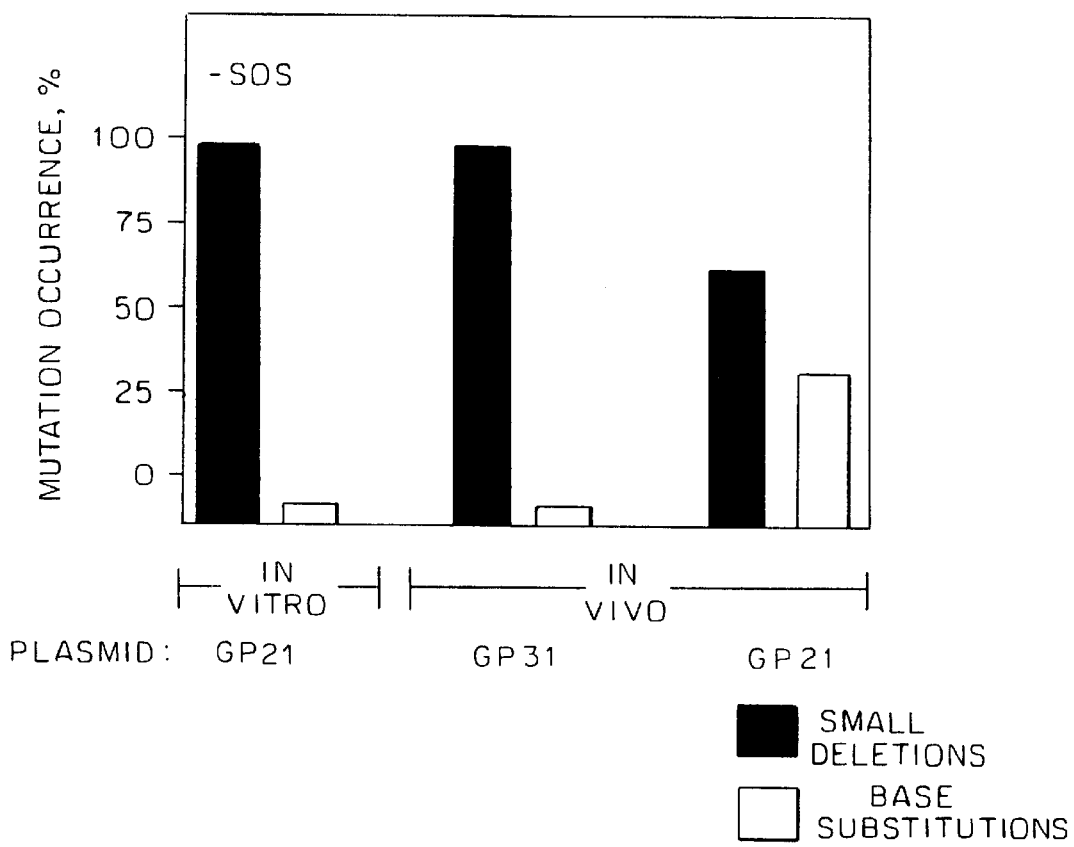
FIGS. 6A and 6B show a comparison of mutations produced with (FIG. 6B) or without (FIG. 6A) SOS induction with the data being taken from Tables 1 and 2.
Figure 6B:
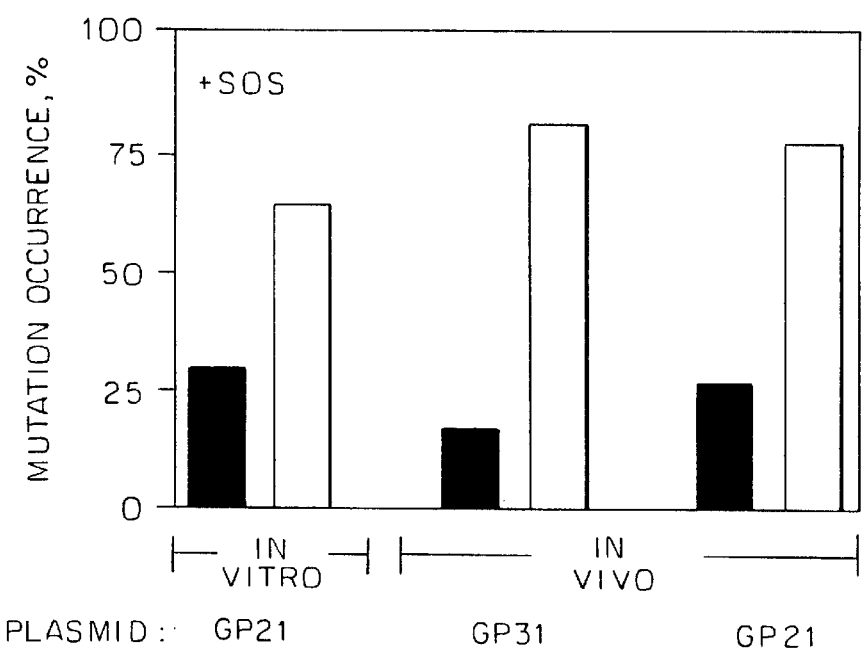

The results of these experiments are presented in Table 2 and FIGS. 6A–6B.

In order to examine whether the UmuD and UmuC proteins were involved in this process in vivo the transformation experiments with an uninduced and SOS-induced ΔumuDC strain were repeated. Plasmid survival was 0.7% in the noninduced ΔumDC cells, but unlike in UmuDC$^+$ cells it was unchanged after SOS induction (Table 2). Thus, increased survival of the gap lesion plasmid in SOS-induced cells was totally dependent on the Umu proteins. The DNA sequence analysis revealed that in the noninduced ΔumuDC cells 86% of the mutations were small deletions, similar to the situation in noninduced UmuDC$^+$ cells. The predominance of small deletions occurred also when the ΔumuDC cells were SOS-induced (Table 2). These results strongly suggest that the UmuD' and UmuC proteins function to suppress small deletions, a lethal type of mutation, and promote base substitutions, a mild type of mutation.

TABLE 2

In Vivo Mutational Specificity of Gapped Plasmids Containing Sit-Specific Synthetic Abasic Sites

| Mutation Type or Plasmid Survival | Substrate GP21 AB1157wt | | WBY100ΔumuDC | | Substrate GP31 AB1157wt | |
|---|---|---|---|---|---|---|
| | −SOS | +SOS | −SOS | +SOS | −SOS | +SOS |
| Base Substitution | | | | | | |
| A | — | 14 | — | — | — | 15 |
| G | — | 1 | — | — | — | 1 |
| T | — | 1 | — | — | — | — |
| C | 8 | 3 | 3 | 8 | — | — |
| Total base substitutions | 8 (32%) | 19 (76%) | 3 (14%) | 8 (36%) | — (0%) | 16 (80%) |
| Deletions | | | | | | |
| −1 | 7 | 2 | 11 | 8 | 18 | 4 |
| −2 | 4 | 3 | 5 | 2 | 5 | — |
| −3 | 4 | 1 | 3 | — | 2 | — |
| Others | 2 | — | — | 4 | — | — |
| Total deletions | 17 (68%) | 6 (24%) | 19 (86%) | 14 (64%) | 25 (100%) | 4 (20%) |
| Total mutants analyzed | 25 | 25 | 22 | 22 | 25 | 20 |
| Plasmid survival | 0.9% | 5.0% | 0.7% | 0.7% | 0.6% | 2.1% |

The gap lesion plasmids GP21 and GP31 were introduced into SOS-induced or noninduced *E. coli* cells, as indicated. Plasmid survival is calculated by dividing the number of transformants by that obtained with the corresponding control gapped plasmid without the lesion.
The table shows the DNA sequence opposite the lesion obtained for individual clones. The details are presented under Experimental Procedures. The values in parentheses represent the percentage of the particular mutation type. The most abundant type of mutation is underlined.

The survival of the gap lesion plasmid GP21 in the noninduced "wild-type" cells was 0.9% compared to a gapped plasmid without a lesion, and it increased to 5.0% in SOS-induced cells (Table 2, bottom). The survival of another gapped plasmid, GP31, was increased by SOS induction from 0.6% to 2.1%. Each plasmid recovered contained a mutation, and all mutations were targeted to the lesion. In the absence of SOS induction, 68% of the mutations in plasmid GP21 were small deletions. Interestingly, when a nucleotide was inserted opposite the lesion in the absence of SOS induction, it was a C, not an A as in SOS-induced cells. The picture changed dramatically when SOS-induced cells were examined: 76% of the mutations were base substitutions, consisting mostly of insertion of A opposite the lesion. The difference in mutational specificity was even more pronounced with plasmid GP31: 100% of the mutations in noninduced cells were small deletions, whereas in SOS-induced cells 71% of the mutations were base substitutions, mostly A (Table 2). These results are consistent with the in vitro results presented above and indicate that SOS induction leads to a suppression of small deletions, and to the promotion of base substitutions (FIG. 6B).

DISCUSSION

Figure 7A:
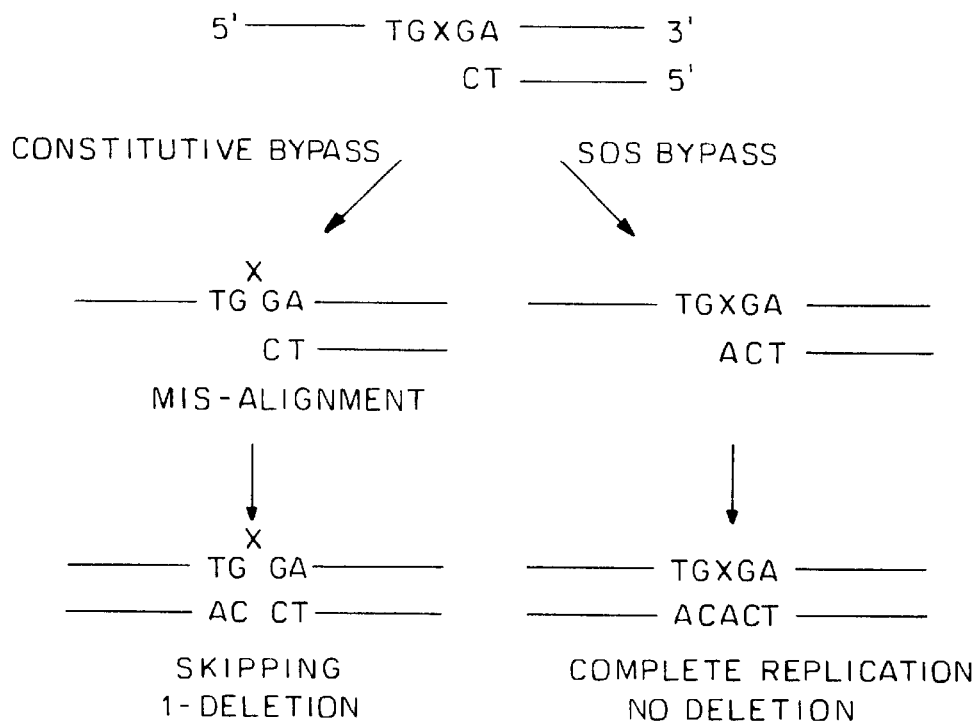
FIGS. 7A and 7B show a model describing SOS and constitutive modes of translesion replication.

The in vitro reconstitution of SOS translesion replication establishes that SOS mutagenesis, at least in the case of abasic sites, proceeds via UmuD', UmuC, RecA, and SSB-stimulated translesion replication, confirming the basic results of Rajagopalan et al. (1992). The laboratory of the present inventors have previously shown that DNA polymerase III holoenzyme can replicate "blocking" lesions at high efficiency, unassisted by any other protein (Livneh, 1986; Hevroni et al., 1988; Tomer et al., 1999). These results presented an apparent paradox: In vitro bypass did not require UmuD', UmuC, and RecA, whereas in vivo bypass did require these proteins. This paradox seems now to be resolved: Pol III holoenzyme can indeed bypass a synthetic abasic site unassisted, but it does so in a "sloppy" way, by skipping over the lesion, and producing mostly −1 deletions (FIG. 7A). Such deletions cause translational frameshifts, which usually render genes nonfunctional. The UmuD' and UmuC proteins stimulate translesion replication and at the same time cause a dramatic change in its mutagenic specificity: They prevent the lethal frameshift mutations while increasing base substitution, a mild type of mutation.

Figure 7B:
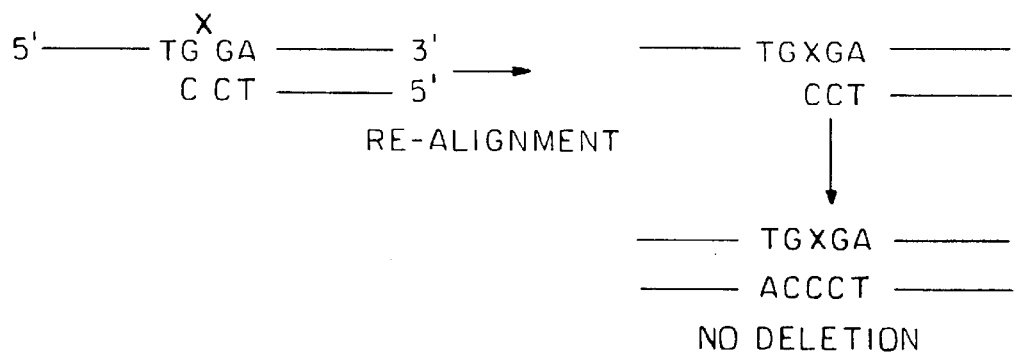

The reason that the polymerase skips over the lesion in the absence of the SOS proteins might be the stabilization of a misaligned abasic site (FIG. 7B). Support for such a model comes from the in vivo experiments that show the identity of nucleotides inserted opposite the lesion in the absence of SOS induction. In contrast to SOS conditions, under which an A is inserted opposite the lesion, in the absence of SOS, when nucleotide was inserted opposite the lesion, it was a C (Table 2). This nucleotide is complementary to the nucleotide next and downstream to the lesion in substrate GP21 (FIG. 7B). Such a phenomenon can be explained as follows: The polymerase skips the lesion and copies the next nucleotide, but in some cases, before proceeding to the next polymerization step, the abasic site flips back in, and the polymerase again copies the nucleotide next to the abasic site and proceeds in replication (FIG. 7B). SOS proteins might prevent misalignment of the lesion, possibly through the formation of a stable multiprotein-DNA complex. The generation of −1 frameshifts during translesion replication by pol III holoenzyme may be related to the propensity of its catalytic α subunit to produce −1 frameshift mutations during a gap-filling replication on undamaged templates (Mo et al., 1996) and to a Umu-independent branch of mutagenesis associated with 2-acetylaminofluorene adducts (Napolitano et al., 1997). A similar behavior was observed for mammalian DNA polymerase β (Kunkel, 1990; Efrati et al., 1997).

A striking feature of the translesion replication system is its very high effectiveness: 70% of the gap lesions were filled in within 12 min (FIG. 5B). This suggests that translesion replication is potentially an effective way to repair gap lesion structures. Its efficiency in acting on chromosomal gap lesion structures in vivo may be limited by at least two factors: First, inhibition of translesion replication by DNA damage-binding proteins through direct binding to the gap lesion (Paz-Elizur et al., 1997b). Second, competition from recombinational repair, which provides an error-free alternative for filling in gap lesion structures. Indeed, it was reported that overproduction of UmuD'C. inhibited recombinational repair (Sommer et al., 1993; Boudsocq et al., 1997).

SOS translesion replication was suggested to act both as a cellular DNA repair mechanism, as well as an inducible mutator (Radman, 1975; Witkin, 1976; Bridges, 1978; Echols, 1981). The suppression of deletion mutations is important for both purposes: there is no point in repairing a gap if the result will be a lethal deletion, and it is inefficient to generate genetic variation by promoting harmful deletion mutations. In both cases, base substitution is a better mutation, because it is usually milder in its biological consequences.

The yeast S. cerevisiae is similar to E. coli with regard to dealing with gap lesion structures by both an error-free recombinational repair mechanism and translesion replication. Unlike E. coli, it has two specialized DNA polymerase for translesion replication reaction: DNA polymerase zeta (ζ), product of the REV3 and REV7 genes (Nelson et al., 1996b) and DNA polymerase eta (η), product of the RAD30 gene (Johnson et al., 1999). In addition, it has a dCMP nucleotidyl transferase, product of the REV1 gene (Nelson et al., 1996a). Mammalian cells do not seem to use homologous recombination extensively (Friedberg et al., 1995), probably due to the high content of repetitive sequences in the mammalian genome. Nevertheless, the DNA is fully replicated, and cells divide even when DNA repair is not complete, and damage persists in the genome (Friedberg et al., 1995). Homologs of the yeast REV3 and RAD30 genes were found in human cells (Gibbs et al., 1998 and Masutani et al., 1993, respectively).

EXAMPLE 2

Effective Translesion Replication is Promoted by UmuC in the Presence of UmuD', RecA and SSB and in the Absence of Added Exogenous DNA Polymerase The experiments in this example were conducted according to the Experimental Procedures below or to the Experimental Procedures in Example 1 unless otherwise noted. DNA polymerase II and DNA polymerase I were used in place of DNA polymerase III.

EXPERIMENTAL PROCEDURES

Proteins

UmuD', UmuD, the MBP-UmuC fusion protein were overexpressed and purified as previously described (Reuven et al., 1998). The UmuC was further purified by heparin SEPHAROSE CL-6B chromatography (Pharmacia). A gradient of 80–1000 mM NaCl was used, and UmuC eluted at 600 mM NaCl. The MBP-UmuC(Δ26C) clone was constructed by cleaving the MBP-UmuC expression plasmid (pMAC) with restriction nuclease BamHI, which makes two cuts: in the C-terminal portion of UmuC, and in the vector. This leads to the deletion of 26 codons of UmuC. An additional codon is added from the vector (CTC; Leu), after which there is a termination codon (TAG). The plasmid was termed pMAC(Δ26C). The MBP-UmuC(Δ26C) protein was overproduced and purified by the same procedure used for the wild type MBP-UmuC. The umuC104 allele was constructed by PCR-based site-directed mutagenesis, introducing the $^{720}$GAT→AAT mutation. This causes an $^{101}$Asp→Asn amino acid substitution in UmuC (Koch et al., 1992). Using plasmid PMAC as a template, the 5'-terminal portion of umuC was amplified using the primers 5'-ATG GGG TAA ACC GGT GGT TGT-3' (#338; SEQ ID NO:19) and 5'-CTC ATT AAT ACT GTA AAT CTC-3' (#342; SEQ ID NO:20); and the 3'-terminal portion of umuC was amplified using the primers 5'CCG GAA TTC TTT ATT TGA CCC TCA GTA AAT C-3' (#131; SEQ ID NO:9) and 5'-GTA TTA ATG AGG CAT TCT GCG -3' (#341; SEQ ID NO:21). The PCR reaction mixture contained 10 mM Tris-HCl pH 8.8, 25 mM KCl, 5 mM $(NH_4)_2SO_4$, 2 mM $MgCl_2$, 200 μM dNTPs, 10 ng pMAC and 2.5 units Pwo DNA polymerase. The reaction protocol included 5 min at 94° C.; then 25 cycles of 30 sec at 94° C., 30 sec at 45° C., and 2 min at 72° C. Finally the mixtures were incubated for 10 min at 72° C. The resulting fragments (241 bp and 983 bp, respectively) contained a sequence overlap of 11 nucleotides spanning the umuC104 mutation. The DNA fragments were gel-purified, mixed and used in a final PCR step with primers #338 and #131 to construct the entire umuC104 gene. The PCR reaction mixture contained 200 ng of each of the umuC104 gene fragments and 50 pmol of each of primers #338 and #131. The protocol included 5 min at 94° C.; 5 cycles of 30 sec at 94° C., 1 min at 23° C. and 2 min at 72° C.; 20 cycles of 30 sec at 94° C., 1 min at 56° C., and 2 min at 72° C. Finally, the mixture was incubated for 10 min at 72° C. The PCR product (1214 bp) was gel-purified, digested with restriction nucleases AgeI and EcoRI, and subcloned into pMAC, that was previously cleaved with the same restriction nucleases. The resulting plasmid was termed pMAC104. The sequence of the umuC104 gene was verified by DNA sequence analysis. The MBP-UmuC104 protein was purified as described for MBP-UmuC.

SSB and RecA were purified as described (Lohman and Overman, 1985; and Cox et al., 1981, respectively), except that a phosphocellulose purification step was added for RecA. Pol II was a generous gift from Myron Goodman (University of Southern California, Los Angeles, Calif.), and pol III core was a generous gift from Michael O'Donnell (Rockerfeller University, New York, N.Y.). Restriction nucleases, T4 DNA ligase and T4 polymucleotide kinase were from New England Biolabs, Beverly, Mass. Pwo DNA polymerase, pol I, and exouclease III were from Boehringer-Mannheim, and T7 gp6 exonuclease was from Amersham.

DNA Substrates

The preparation of the gapped plasmid carrying a site-specific lesion was recently described (Tomer et al., 1998; Tomer and Livneh, 1999). Throughout this study, gapped plasmid GP21, which contained a site-specific synthetic abasic site (FIG. 1), was used. The gapped plasmid was gel-purified, and the gap was extended to a size of approximately 350 nucleotides using the T7 gp6 5'→3' exonuclease, as described before (Tomer et al., 1998). All oligonucleotides were synthesized and purified by the Synthesis Unit of the Biological Services Department at the Weizmann Institute of Science. Oligonucleotides containing the synthetic abasic site analog were synthesized similarly using dSpacer CE phosphoramidate (Glen Research) as a building block. The abasic site analog is a modified tetrahydrofuran moiety which is a stable analog of 2' deoxyribose in the abasic site. It has a hydrogen instead of a hydrozyl residue on the 1' carbon of the deoxyribose ring (Takeshita et al., 1987).

The undamaged gapped plasmid (a plasmid with no base lesion) was prepared as follows. Plasmid pOC2 (Cohen-Fix and Livneh, 1992; 80 μg), a derivative of pBR322, was nicked with restriction nuclease AatII (160 units), in the presence of 0.1 mg/ml ethidium bromide, in a total volume of 320 μl, for 30 min at 37° C. Under these conditions the activity of AatII was inhibited, and as a result it introduced a single nick rather than a double strand cut. Two populations of open circular plasmids (FII) were formed, each nicked on another DNA strand. The nicks were converted into gaps using exonuclease III, in a reaction mixture (300 μl) containing 30 μg FII pOC2 and 300 units exonuclease III, for 25 min at 37° C. The size of the gap was deduced to be approximately 350 nucleotides, based on the electrophoretic migration of the DNA after digestion of the ssDNA region with S1 nuclease.

Figure 13:
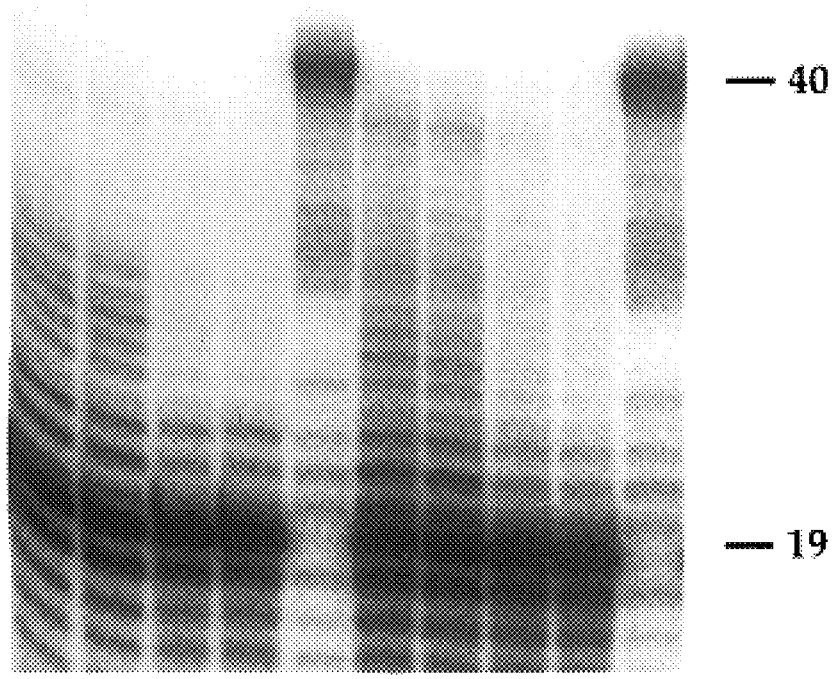
FIG. 13 shows the phosphorimage of DNA synthesis products from the DNA polymerase activity of UmuC in the absence of RecA and SSB. The reactions were performed with a primed oligonucleotide, or a gapped duplex oligonucleotide, as described under Experimental Procedures in Example 2, with 230 nM MBP-UmuC and 2.5 $\mu$M UmuD'. Pol I (90 nM) was used as a control. The reactions were conducted for 30 min at 37° C. UmuC (HP) is the MBP-UmuC protein purified by an additional heparin SEPHAROSE column.

The primed and the gapped oligonucleotides were prepared as previously described (Paz-Elizur et al., 1996; Paz-Elizur et al., 1997). Briefly, a $^{32}$P-5'-labeled synthetic 19-mer (5'TGCTGCAAGGCGATTAAGT-3') (SEQ ID NO:22) was annealed to the template 5'GGAAAACCCTG-GCGTTAGCCGACTTAATCGC CTTGCAGCA-3' (40-mer; SEQ ID NO:23), to generate the primed template. The gapped duplex oligonucleotide was prepared in a similar way, except that an additional oligonucleotide, 16 nucleotides long (5'AACGCCAGGGTTTTCC-3') (SEQ ID NO:24) was annealed to the template, such that a duplex with a 5 nucleotides ssDNA gap was formed (FIG. 13).

Translesion Replication Assay

Figure 9A:
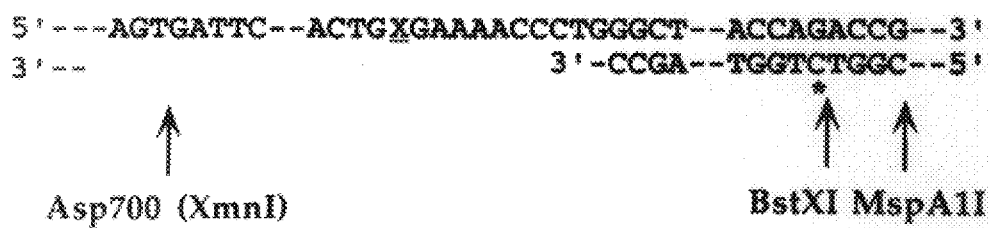
FIG. 9A shows the DNA substrate used in the lesion bypass assay and FIG. 9B shows the phosphorimage of products from translesion replication by low concentrations of UmuC in the presence of UmuD', RecA and SSB.

The translesion replication reaction mixture (25 μl) contained 20 mM Tris-HCl, pH 7.5, 8 μg/ml bovine serum albumin, 5 mM DTT, 0.1 mM EDTA, 4% glycerol, 1 mM ATP, 10 mM MgCl$_2$, 0.1 mM each of dATP, dGTP, dTTP and dCTP, 0.1 μg (2 nM) gapped plasmid, 0.6 μM SSB, 4 μM RecA, 2.5 uM UmuD' or UmuD, and 10–230 nM MBP-UmuC. Reactions were carried out at 37° C. for the indicated periods of time, after which they were terminated by adding SDS to 0.2%, EDTA to 20 mM and NaCl to 100 mM, and heat-inactivated at 65° C. for 10 min. The proteins were digested with 0.4 mg/ml proteinase K at 37° C. for 1 hr, after which the DNA was extracted with phenol-chloroform and ethanol-precipitated. Before electrophoretic fractionation of the replication products, they were digested with restriction nucleases, in order to reduce their size, and therefore increase resolution. The original cleavage procedure with XmnI and BstXI (Example 1 and Reuven et al., 1998) was modified as follows: prior to the addition of restriction nucleases, the translesion replication products were treated with calf intestine alkaline phosphatase (0.2 units, 1 hr, 37° C.), to hydrolyze any remaining dNTPs. This step was introduced because some restriction nuclease preparations were found to be contaminated with DNA polymerase. Then restriction nucleases Asp700 (an isoschizomer of XmnI; 5 units/tube) and MspA1I (which cleaves 4 nucleotides upstream to BstXI; FIG. 9A; 5 units/tube) were added, and incubated for 2 hours at 37° C. This produced radiolabeled DNA bands which were 4 nucleotides longer than with the XmnI/BstXI cleavage. The DNA sample was treated with proteinase K, after which it was fractionated by electrophoresis on 15% polyacrylamide gels containing 8 M urea. Gels were run at 1500–2000 V for 2–3 hr, after which they were dried, and visualized and quantified using a Fuji BAS 2500 phosphorimager. The extent of translesion replication was calculated by dividing the amount of bypass products by the amount of the extended primers.

DNA Synthesis Assays

Gap-filling DNA synthesis was performed with unlabeled gapped plasmid pOC2, which contained no nucleotide lesions. The reaction mixture (25 μl) was performed under conditions similar to those of the translesion replication reaction, except that it contained 5 nM gapped plasmid pOC2, 0.1 mM each of dATP, dCTP and dGTP, 10 μM α-$^{32}$P dTTP, 0.6 μM SSB, 4.2 μM RecA, 2.0 or 4.8 μM UmuD', 50–500 nM of the fusion UmuC protein, and 8 units/μl of T4 DNA ligase. Pol II, when used, was at 9 nM. Reactions were incubated for 5–40 min at 37° C., after which the reaction products were analyzed by agarose gel electrophoresis followed by phosphorimaging. Primer extension assays by UmuC were performed with $^{32}$P end-labeled primed oligonucleotide or gapped duplex oligonucleotide. The reaction mixture (25 μl) was similar to that of the translesion replication assay except that oligonucleotide substrates were at 55 nM. Primer extension was performed with the UmuC fusion protein (230 nM), or after an additional heparin SEPHAROSE chromatography step, in the presence or absence of 2.5 μm UmuD'. The control reactions were with pol I (90 nM). Reactions were incubated for 30 min at 37° C., after which they were analyzed by urea-PAGE followed by phosphorimaging.

RESULTS

Further analysis of the system in Example 1, with or without DNA polymerase, surprisingly revealed that effective translesion replication was promoted by UmuC, UmuD', RecA and SSB, in the absence of added exogenous DNA polymerase. FIG. 8 shows a side-by-side comparison of translesion replication by purified DNA polymerase II or by UmuC in the presence of UmuD', RecA and SSB. The reaction conditions are: 2 nM DNA GP21, 20 mM Tris-HCl pH 7.5, 10 mM MgCl$_2$, 0.5 mM dithiothreitol, 0.1 mM EDTA, 8 μg/ml bovine serum albumin, 4% glycerol, 1 mM ATP, 0.5 mM each of dATP, dGTP, dCTP and dTTP, 4 μM RecA, 0.6 μM SSB (as tetramers), 2.5 μM UmuD', and 234 nM MBP-UmuC fusion protein. DNA polymerase II was at 90 nM. The reaction products were processed and analyzed as described in Example 1. Replication by DNA polymerase II was strongly inhibited at the abasic site (FIG. 8, lanes 2–4; the 25-mer product), a behavior typical for all known DNA polymerases from E. coli (Paz-Elizur et al., 1996; Paz-Elizur et al., 1997; Tomer et al., 1999). In contrast, UmuC/UmuD'/RecA/SSB easily bypassed the same lesion with little inhibition at the lesion (FIG. 8, lanes 5–7). Interestingly, when DNA polymerase II was added to UmuC/UmuD'/RecA/SSB, it inhibited lesion bypass, most likely by competition for the primer terminus (FIG. 8, lanes 8–10).

Figure 9B:
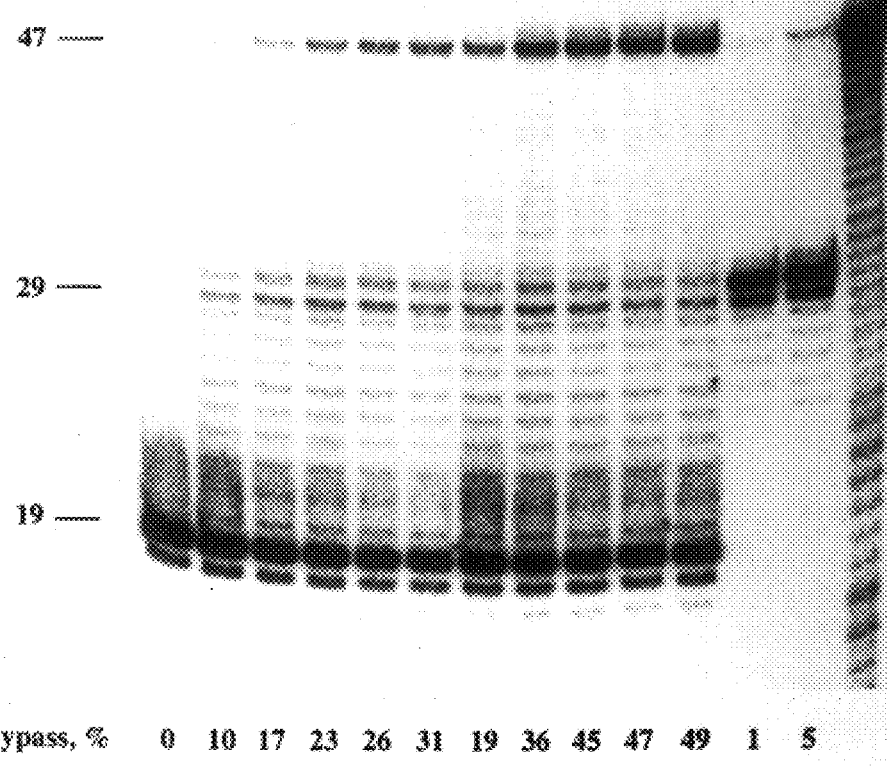

In the attempt to elucidate the mechanism of this lesion bypass reaction, the question of whether all 10 subunits of pol III holoenzyme were required for Umu-dependent translesion replication was examined. The substrate used, termed GP21, was a gapped plasmid containing a synthetic abasic site in the ssDNA region, and a internal radiolabeled phosphate in the primer terminus strand (Example 1 and Reuven et al., 1998; Tomer et al., 1998). A portion of GP21, including the vicinity of the lesion, is shown in FIG. 9A. Addition of a DNA polymerase led to extension of the primer up to the lesion, and when lesion bypass occurred, synthesis continued past the lesion. The analysis of replication products was done by cutting the products with restriction nuclease MspA1I, which cuts 4 nucleotides upstream to the radiolabel, and Asp700 (or its isoschizomer XmnI), which cuts downstream to the lesion (FIG. 9A), followed by urea-PAGE. The products were then visualized and quantified by phosphorimaging (FIG. 9B). Surprisingly, translesion replication was found to occur in the absence of any added pol III holoenzyme subassembly. This suggested that one of the components other than pol III contained DNA polymerase activity. The prime candidate was UmuC, because in contrast to UmuD' (molecular mass 12 kDa), it is large enough to be a DNA polymerase (molecular mass 48 kDa).

Initially, UmuC was used at a concentration of 200–250 nM, which is its presumed in vivo concentration under SOS induction (FIG. 8). Such high concentrationS raised the possibility of a contaminating DNA polymerase in the UmuC preparation. The concentration of UmuC was then reduced to 50 nM and 10 nM, and the time course of translesion replication with these low UmuC concentrations, in the presence of UmuD', RecA and SSB, was examined. The reaction conditions were as described above for FIG. 8, except that UmuC was at 10 or 50 nM, as indicated. The analysis of the products was as described in Example 1, except that the products were cleaved with MspA1 (instead of BstXI) and Asp700 (isoschizomer of XmnI that was previously used), yielding products of 19, 29 and 47 nucleotides long for the unextended primer, the blocked product, and the bypass product, respectively. As can be seen in FIG. 9B, translesion replication occurred also under low UmuC concentrations. Initiation of replication by the UmuC polymerase was not very effective, as indicated by the amount of unextended primer (FIG. 9B). This means that there might exist a protein that stimulates initiation by UmuC. However, once polymerization started, there was little pausing at the lesion, progressing without much inhibition at the lesion. For comparison, FIG. 9B also contains reactions with DNA polymerase I (pol I). Like the results with DNA polymerase II (FIG. 8), DNA polymerase I was strongly inhibited at the abasic site, and very little bypass occurred (FIG. 9B, lanes 12, 13). These results indicate that one of the proteins, most likely UmuC, is a DNA polymerase, specialized for translesion replication.

Figure 10:
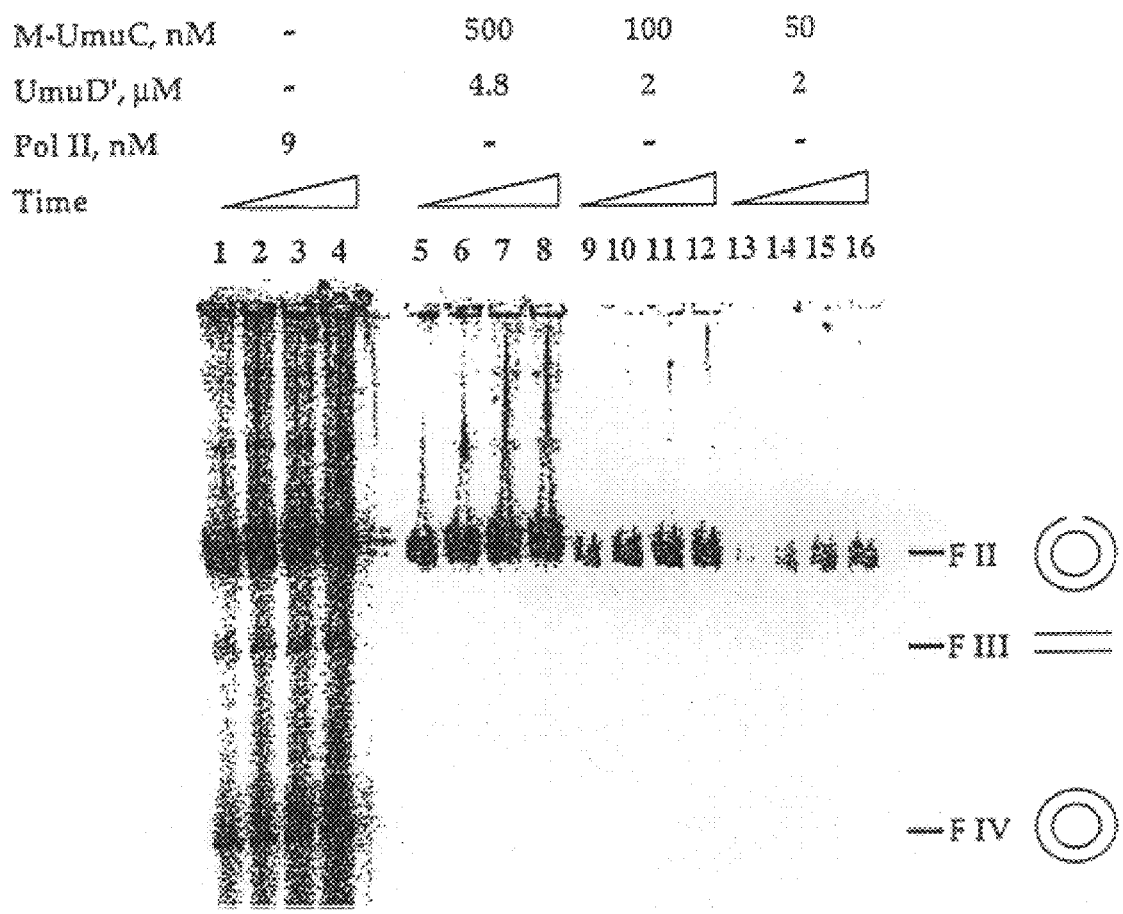
FIG. 10 shows the phosphorimage of products of DNA synthesis by UmuC on an undamaged gapped plasmid, in the presence of UmuD', RecA and SSB. The time points are 5, 10, 20 and 40 minutes per set of four lanes 1–4, 5–8, 9–12, and 13–16. The samples were then treated with proteinase K and fractionated by agarose gel electrophoresis, dried and visualized by phosphorimaging. Form III (FIII) is a linear form; form II (FII) is a nicked circle; and form IV (FIV) is a covalently closed circle. M-UmuC is the MBP-UmuC fusion protein.

The DNA polymerase activity of UmuC on undamaged DNA in the form of a gapped plasmid without any lesions was examined. This was done by following the incorporation of radiolabeled dTTP during gap-filling replication with an unlabeled gapped plasmid which contained no base lesions. The plasmid was prepared by nicking plasmid pOC2 (Cohen et al., 1992) with restriction nuclease AatII in the presence of ethidium bromide. Under such conditions, AatII introduces a nick on one strand, such that two populations, each carrying the nick on another strand are produced. The nicks in this plasmid were converted to gaps of approximately 350 nucleotides by using exonuclease III. Gap-filling DNA replication was assayed on these substrates by following the incorporation of $\alpha$-$^{32}$P radiolabeled dTTP. Reaction conditions were as described above for FIG. 8 except that undamaged gapped plasmid pOC2 (6.2 nM) was used, T4 DNA ligase was included (4 units/μl), dATP, dGTP and dCTP were at 0.1 mM each, $\alpha$-$^{32}$P dTTP was at 10 μM, and UmuC, UmuD' and polII were at the concentrations indicated in FIG. 10. After the reaction, the DNA was treated with proteinase K and fractionated by agarose gel electrophoresis, followed by visualization by phosphorimaging. FIG. 10 shows a time course of DNA synthesis promoted by UmuC/UmuD'/RecA/SSB, with various concentrations of UmuC. DNA synthesis by DNA polymerase II (pol II) served as a positive control. As can be seen in FIG. 10, the control reactions, performed with DNA polymerase II, showed gap-filling replication, yielding primarily the circular nicked plasmid (form II, FII; FIG. 10, lanes 1–4). Similarly, incubation of the gapped plasmid with UmuC/UmuD'/RecA/SSB led to a time dependent, and UmuC concentration-dependent DNA synthesis. Thus, it is clear that UmuC/UmuD'/RecA/SSB proteins catalyze DNA synthesis on this undamaged gapped plasmid.

Figure 11:
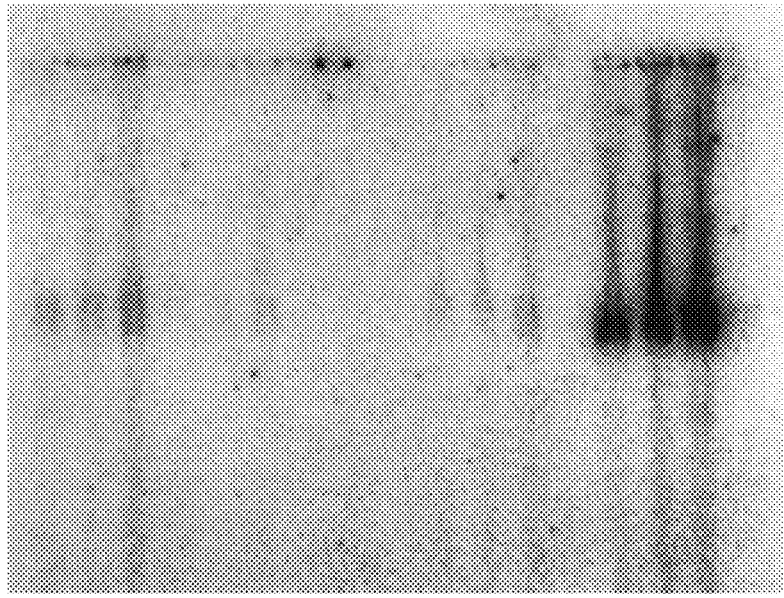
FIG. 11 shows the phosphorimage of DNA synthesis by UmuC DNA polymerase activity as stimulated by the presence of UmuD', RecA and SSB. The reaction conditions are the same as in FIG. 10 and with the protein compositions indicated in the top of FIG. 10, except that MBP-UmuC was at 500 nM, and UmuD' was at 4.8 $\mu$M. The time points are 5, 10 and 20 minutes at 37° C. per set of three lanes 1–3, 4–6, 7–9, 10–12, and 13–15. The samples were then treated with proteinase K and fractionated by agarose gel electrophoresis, dried and visualized by phosphorimaging. As in FIG. 10, FII is a nicked circle.

The new DNA polymerase was suspected to be UmuC. In order to examine this possibility, an experiment was performed with the undamaged gapped plasmid, in which each of the components was omitted, one at a time, from the reaction mixtures. The reaction conditions were as described above for FIG. 10, and with the protein compositions indicated on top of FIG. 11, except that MBP-UmuC was at 500 nM, and UmuD' was at 4.8 μM. Following the reaction, the samples were treated with proteinase K, and fractionated by agarose gel electrophoresis. The gels were dried and visualized by phosphorimaging. As can be seen in FIG. 11, omission of each of RecA (FIG. 11, lanes 1–3), SSB (FIG. 11, lanes 4–6), and UmuD' (FIG. 11, lanes 10–12) caused a strong reduction, but not complete elimination of DNA synthesis activity. In contrast, omission of UmuC caused a complete elimination of DNA synthesis (FIG. 11, lanes 7–9). This indicates that UmuC is indeed a DNA polymerase and that UmuD', RecA and SSB cause a strong stimulation of its activity.

The ability of the UmuC fusion protein to promote lesion bypass at a concentration as low as 10 nM (FIG. 9B) argues against the possibility that the DNA polymerase activity in the MBP-UmuC preparation stems from a contamination of pol I, pol II or pol III. The MBP-UmuC protein was purified from a strain lacking pol II, and full lesion bypass activity was obtained (data not shown). This eliminated the possibility of a contamination of pol II. In another approach, the effect of adding purified pol III core on lesion bypass by UmuC/UmuD'/RecA/SSB was examined. The rationale was that if pol III core existed as a minor contaminant in the MBP-UmuC preparation, adding more of it would increase lesion bypass. As can be seen in FIG. 12, addition of pol III core to UmuC/UmuD'/RecA/SSB did not cause any increase in lesion bypass; In fact a slight inhibition was observed, possibly due to competition for the primer-template (FIG. 12). Similar results were obtained when pol I was added to UmuC/UmuD'/RecA/SSB (data not shown).

Finally, whether or not DNA polymerase activity of UmuC alone could be detected was tested. This was done using a synthetic oligonucleotide template, 40-nucleotides long, primed with a $^{32}$P end-labeled 19-mer oligonucleotide. In addition, a gapped duplex oligonucleotide was prepared, by annealing an additional 16-mer oligonucleotide to the same template, such that a five nucleotides single-stranded gap is formed (FIG. 13; Paz-Elizur et al., 1997a). The reactions were performed with a primed oligonucleotide, formed by the annealing of a 40-mer template and a $^{32}$P ended-labeled 19-mer primer. This substrate was converted to a gapped duplex by annealing with an additional oligonucleotide, 16-nucleotide long, such that a five nucleotide single-stranded DNA gap was formed (illustrated in the upper part of FIG. 13). DNA polymerase activity leads to the extension of the radiolabeled primer. The reaction conditions were as described in for FIG. 8, except that the reactions were performed without RecA and SSB, the DNA substrates were at 55 nM, UmuC was at 230 nM, and UmuD' at 2.5 $\mu$M. DNA polymerase I (90 nM) was used as a control. The reactions were conducted for 30 min at 37° C. UmuC (HP) is the fusion UmuC protein purified by an additional heparin Sepharose column. As can be seen in FIG. 13, UmuC alone had a very weak DNA polymerase activity, but was slightly stronger on the gapped duplex (FIG. 13, compare lane 4 to lane 9). The UmuC protein was subjected to an additional purification step on a heparin-Sepharose affinity column. As can be seen in FIG. 13, the DNA polymerase activity of this preparation was higher, as compared to the previous preparation (FIG. 13, compare lane 2 to lane 4). Again, activity on the gapped duplex was higher than on the primer template (FIG. 13, compare lane 2 to lane 7). Adding UmuD' did not change the activity of UmuC (FIG. 13, lanes 1, 3, 6, 8). The ability of UmuC to bypass an abasic site was tested with the same set of oligonucleotides, which contained a synthetic abasic site in the template strand at position 20 (Paz-Elizur et al., 1996). It was found that UmuC alone, or together with UmuD', were unable to bypass the lesion (data not shown). The same result was obtained with the gapped plasmid GP21 (see below). Therefore, although UmuC is a DNA polymerase, its remarkable lesion bypass ability depended on UmuD', RecA and SSB.

Figure 16:
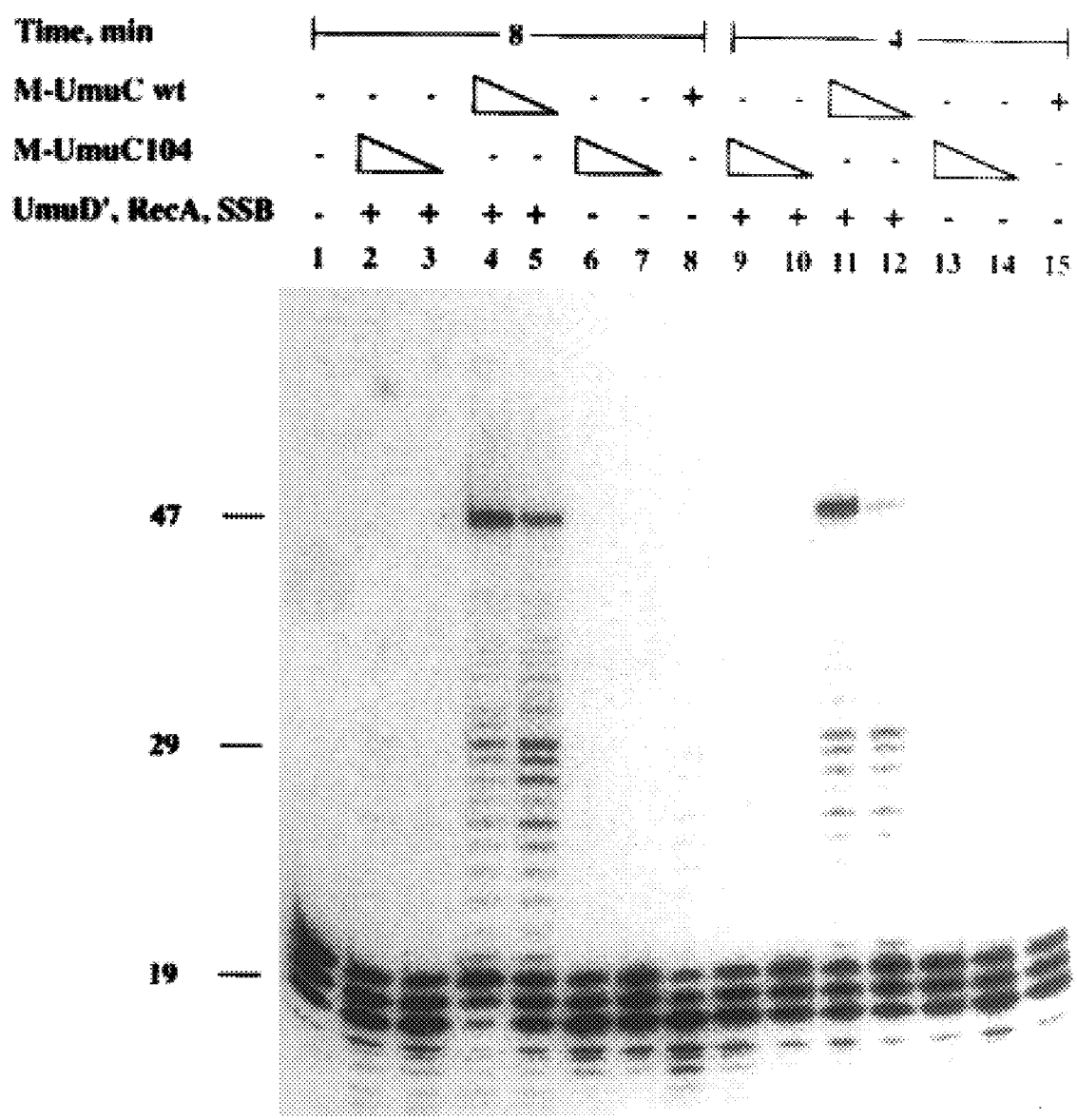
FIG. 16 shows a phosphorimage demonstrating that the UmuC104 protein is defective in both lesion bypass and DNA synthesis. The translesion replication reactions were performed as described under Experimental Procedures in Example 2 with MBP-UmuC or MBP-UmuC104 (50 and 200 nM each), in the presence of UmuD', RecA and SSB. MBP-UmuC and MBP-UmuC104 were at 200 nM each when assayed in the absence of UmuD', RecA and SSB.

Two umuC mutants were constructed, a truncated UmuC missing the C-terminal 26 amino acids UmuC($\Delta$26C), and UmuC104, a known chromosomal mutant, which contains an $^{101}$Asp$\rightarrow$Asn amino acid substitution. Both mutant proteins were overproduced and purified. A side-by-side comparison was performed of the activities of UmuC and UmuC($\Delta$26C) in the translesion replication assay in the presence of UmuD', RecA and SSB. As can be seen in FIG. 14, the mutant protein was completely defective in lesion bypass. Interestingly, it retained DNA synthesis activity, as indicated by the extension of the primers up to the lesion (FIG. 14). This was confirmed by examining the DNA synthesis activity of the UmuC($\Delta$26C) protein alone. As can be seen in FIG. 15, the mutant protein did not lose its DNA polymerase activity; in fact, its activity was slightly higher than of the wild-type UmuC (FIG. 15, lanes 6, 7). A similar analysis was performed for the UmuC104 protein. In vivo the umuC104 mutant is defective in SOS mutagenesis (Steinborn, 1978; Koch et al., 1992). Similar to its in vivo phenotype, and to the behavior of UmuC($\Delta$26C), UmuC104 was totally defective in translesion replication (FIG. 16, compare lanes 2, 3 to 4, 5; and lanes 9, 10, to lanes 11, 12). However, in contrast to UmuC($\Delta$26C), it was also defective in DNA synthesis (FIG. 16, lanes 6, 7 and lanes 13, 14). Taken together these results indicate that UmuC is a lesion bypass DNA polymerase, whose activity requires UmuD', RecA and SSB.

DISCUSSION

Several lines of evidence demonstrate that the SOS-inducible mutagenesis protein UmuC is a DNA polymerase, specialized for translesion replication in the presence of UmuD', RecA and SSB: (1) Translesion replication occurred in vitro without adding any of the three well-known DNA polymerases of E. coli; (2) Lesion bypass was obtained at low UmuC concentrations of 10 nM (FIG. 10), and even 5 nM (data not shown), conditions under which the amount of contaminants in the purified MBP-UmuC is extremely low; (3) The DNA polymerase activity of the Umuc fusion protein was retained when it was purified from an E. coli strain lacking pol II, therefore eliminating the possibility of a contamination of pol II; (4) Adding pol I or pol III core to translesion replication reactions did not increase lesion bypass; in fact it caused some inhibition, probably due to competition for the primer-template terminus; and (5) The UmuC($\Delta$26C) protein was defective in translesion replication, but not in DNA synthesis, and the UmuC104 mutant protein was defective both in lesion bypass and DNA synthesis. Tang et al have recently reported that a complex of UmuD'$_2$C performed DNA synthesis, indicating that it might be a DNA polymerase (Tang et al., 1998). However, since a high concentration of UmuD'$_2$C was used (200 nM), the presence of a contaminating DNA polymerase could not be excluded, as the authors themselves stated (Tang et al., 1998). A major difference between our results and those of Tang et al, is that in their system bypass depended on six accessory subunits of pol III: The $\beta$ subunit DNA sliding clamp, and the 5-subunit clamp loader $\gamma$ complex (Tang et al., 1998). In our system, only MBP-UmuC, UmuD', RecA and SSB are required.

Homologues of the umuC gene exist in a wide range of organisms from bacteria to humans (Sedgwick et al., 1991; McDonald et al., 1997; Johnson et al., 1999a; Masutani et al., 1999). This year, two eukaryotic homologues, RAD30 of S. Cerevisiae, and XP-V, which is mutated in human genetic disease Xeroderma Pigmentosum Variant, were found to encode a novel DNA polymerase termed DNA polymerase $\eta$ (Johnson et al., 1999a; Masutani et al., 1999). This DNA polymerases was shown to have the remarkable ability of replicating through DNA lesions. Therefore, there is a new class of DNA polymerase, the UmuC class, which shares no homology with any of the other known DNA polymerase classes. This class of DNA polymerases is specialized for translesion replication. In addition, the E. coli dinB gene was recently shown to encode a DNA polymerase (Wagner et al., 1999). This gene is a umuC homologue, which functions in phage $\lambda$ untargeted mutagenesis (Brotcorne-Lannoye and Maenhaut-Michel, 1986), and produces primarily frameshift mutations (Kim et al., 1997). It is not required for SOS mutagenesis targeted to DNA lesions, neither is it required for chromosomal untargeted mutagenesis (SOS mutator activity) (Kenyon and Walker, 1980;

Fijalkowska et al., 1997). DinB was termed DNA polymerase IV, hence the present inventors term UmuC, DNA polymerase V.

The translesion replication behavior of the UmuC/UmuD'/RecA/SSB DNA polymerase in SOS mutagenesis bears striking differences from the three well known DNA polymerases of E. coli. The initiation of polymerization by the SOS polymerase is slow under our reaction conditions, as indicated by the amount of unextended primer termini. This might indicate that loading of the UmuC DNA polymerase on DNA may require a special factor, although at this stage the possibility that the fused MBP moiety interferes with initiation cannot be excluded. As indicated above, Tang et al have reported that SOS lesion bypass required the β subunit sliding DNA clamp, and the γ complex clamp loader, which together make up for six of the subunits of pol III holoenyme (Tang et al., 1998). The laboratory of the present inventors have shown in Example 1 that pol III holoenzyme was required for lesion bypass, without establishing which of the 10 subunits of pol III holoenzyme were needed. It is clear from the results presented here that the actual replication of the abasic site did not require any of the subunits of pol III holoenzyme. However, pol III holoenzyme, or at least some of its subunits may act along with UmuC to increase the overall efficiency of translesion replication. This can be done, for example, by stimulating the initiation stage of translesion replication, or by facilitating the extension of products bypassed by UmuC/UmuD'/RecA/SSB. Such possiblitities might explain in vivo requirement for pol III in SOS mutagensis (Bridges et al., 1976; Brotcorne-Lannoye et al., 1985; Bridges and Bates, 1990).

Strikingly, once replication started, there was hardly any inhibition at the synthetic abasic site: The UmuC polymerase has the remarkable ability to effectively replicate the synthetic abasic site, which severely blocks DNA polymerases I, II and III (Takeshita et al., 1987; Paz-Elizur et al., 1996; Paz-Elizur et al., 1997; Tomer and Livneh, 1999). An interesting feature of the translesion replication activity of the UmuC DNA polymerase, its total dependence on UmuD', RecA, and SSB. This is different from the yeast or human DNA polymerase η, each of which is capable of unassisted translesion replication (Johnson et al., 1999a; Masutani et al., 1999). The dependence of lesion bypass by UmuC on UmuD' and RecA parallels the in vivo requirement for UmuD' and RecA in SOS mutagenesis. SSB was not reported to be required for in vivo UV mutagenesis; however, this does not exclude the possibility it is required, given the severe phenotype of most ssb conditional mutations (ssb is an essential gene). The present inventors favor the hypothesis that SSB helps in loading the RecA filament on the pre-mutagenic ssDNA region which carries the lesion.

It was previously shown that the C-terminal 50 amino acids of UmuC are important for its activity in SOS mutagensis (Woodgate et al., 1994). This is consistent with the results with the UmuC(Δ26C) mutant in the laboratory of the present inventors, which showed complete loss of translesion replication activity. Interestingly, this mutatant protein has not lost its weak DNA synthesis activity, suggestign that the active site of the UmuC polymerase does not involve the C-terminal 26 amino acids. The defect might be in the interaction of UmuC with one of the other proteins which are required. The UmuC104 mutant protein was simultaneously defective in translesion replication and in DNA synthesis, indicating that [101]Asp is essential for both polymerase and bypass activities. This mutation is in the SIDE motif, which is conserved among all homologues of UmuC (Friedberg et al., 1995; McDonald et al., 1997), and was shown to be essential for the activity of the RAD30 gene product of S. cerevisiae (Johnson et al., 1999b).

The discovery of the UmuC family of DNA polymerase underscores the theme of DNA polymerases with specialized functions. There are DNA polymerases for chromosome replication, for excision repair, and now also for translesion replication. Based on translesion replication in S. cerevisiae, an interesting distinction emerges between two types of translesion replication reations, which differ in their mutagenic outcome, at least for some types of DNA damage. Mutagenic translesion replication in S. cerevisiae depends on the REV1, REV3 and REV7 genes, as indicated by the non-UV mutability of mutants defective in these genes (Lawrence, 1994). REV3 encodes a DNA polymerase, which combines with the REV7 geneproduct to form DNA polymease ζ (Nelson et al., 1996b). Interestingly, REV3 shares homology with DNA polymerase δ, and not with UmuC. REV1 shares homology with umuC, and encodes a dCMP terminal transferase (Nelson et al., 1996a). However, its role in translesion replication in vivo is not clear.

Another translesion replication pathway depends on the RAD30 gene, which encodes DNA polymerase η. However, despite the fact that pol η is a lesion bypass DNA polymerase (Johnson et al., 1999a), and a homologue of UmuC (McDonald et al., 1997), RAD30 mutants are not defective in mutagenesis by UV light or MMS (McDonald et al., 1997; Roush et al., 1998). This indicates that RAD30 might be involved in an error-free translesion replication process. A similar exists in human cells: Error-prone translesion replication might be conducted by a homologue of DNA polymerase ζ (Gibbs et al., 1998; Xiao et al., 1998), whereas error-free translesion replication appears to be preformed by pol η, product of the XP-V gene (Masutani et al., 1999). Indeed, XP-V cell lines were found to be UV-hypermutable (Maher et al., 1976; Wang et al., 1993). Therefore, although DNA polymerase η, and the UmuC DNA polymerase V are structural homologues, they function in translesion replication pathways which differ in their mutagenic outcome.

EXAMPLE 3

Highly Mutagenic Replication by Umuc (DNA Polvmerase V or PolV) Provides a Mechanistic Basis for SOS Untargeted Mutagenesis The experiments in this example were conducted according to the Experimental Procedures and Materials below.

EXPERIMENTAL PROCEDURES

Materials

The sources of materials used were as follows: nucleotides and DTT, Boehringer Mannheim, Indianapolis, Ind.; ethidium bromide, Sigma, St. Louis, Mo.; and [α-$^{32}$P]dTTP, Amersham, Piscataway, N.J.

Proteins

The fusion maltose-binding protein (MBP-UmC protein and UmuD' were purified as described previously in Example 2 and Reuven et al. (1998). Pol III holoenzyme, SSB, and RecA were purified according to published procedures (Cull et al., 1995; Lohman et al., 1985; Cox et al., 1981, respectively), except that a phosphocellulose purification step was added for RecA. DNA polymerase II was a gift from M. Goodman (University of Southern California, Los Angeles), and the E. coli MutM (Fpg) protein was a gift from J. Laval (Institute Gustave Roussy, Villejuif, France) and S. Boiteux (Commissariat Energie Atomique, Fontenay Aux Roses, France). Uracil DNA N-glycosylase was purchased from United States Biochemical, Cleveland, Ohio; pol I, exonuclease III, BSA, and proteinase K were from Boehringer Mannheim; S1 nuclease was from Promega, Madison, Wis. and restriction nuclease AatII, dam methylase, and T4 DNA ligase were from New England Biolabs, Beverly, Mass.

Gapped Plasmid

Plasmid pOC2 is a pBR322, derivative carrying the cro gene, which was used previously in the laboratory of the present inventors for mutagenesis studies (Cohen-Fix et al., 1992; Cohen-Fix et al., 1994; Skaliter et al., 1992; Barak et al., 1995; Tomer et al., 1996). Treatment of pOC2 with the restriction nuclease AatII in the presence of ethidium bromide (Barzilai, 1973) produced two populations of plasmid, each nicked in one of the two complementary strands (FIG. 17). Subsequently, exonuclease III was added to extend the nicks into gaps. Note that the cro region was single-stranded and, therefore, could be replicated in only half of the molecules (FIG. 17). This limitation, however, did not interfere with the assay, because the unreplicated DNA did not add a significant mutagenesis background (see below). The nicks were introduced upstream to the cro gene, using 0.025 unit/$\mu$l of the restriction nuclease AatII, in the presence of 0.11 $\mu$g/$\mu$l ethidium bromide, and 77 nM plasmid pOC2, at 37° C. for 30 min. The DNA was precipitated with ethanol to remove the ethidium bromide, then extracted with phenol, and precipitated again. The gap was generated in a reaction mixture containing 30 nM nicked pOC2, 1 unit/$\mu$l exonuclease III, 66 nM Tris-HCl (pH 7.5), 0.66 mM $MgCl_2$, 1 mM DTT, and 90 mM NaCl. The reaction was carried out at 37° C. for 20 min to obtain a ssDNA region of approximately 350 nucleotides. The size of the gap was deduced from the electrophoretic migration of the DNA after treatment with nuclease S1, which digested the single-stranded region in the plasmid.

In vitro Replication Fidelity Assay

The standard gap-filling replication reaction mixture (50 $\mu$l) contained 20 mM Tris-HCl (pH 7.5), 8 $\mu$g/ml BSA, 5 mM DTT, 0.1 mM EDTA, 4% glycerol, 1 mM ATP, 10 mM $MgCl_2$, 0.5 mM each of dATP, dGTP, dTTP, and dCTP, and 1 $\mu$g (6.2 nM) gapped pOC2. The replication was carried out with 0.5 $\mu$M UmuC fusion protein in the presence of 4.8 $\mu$M UmuD', 0.6 $\mu$M SSB, 4.2 $\mu$M RecA, and 200 units of T4 DNA ligase. Control reactions were performed with 1.5 nM pol III holoenzyme, 11 nM DNA pol I, or 11 nM DNA pol II. Reactions were carried out at 37° C. for 20 min, after which they were terminated by heat inactivation at 65° C. for 10 min. The DNA then was methylated by adding 32 units of dam methylase, 80 $\mu$M S-adenosylmethionine, 50 mM Tris-HCl (pH 7.5), 10 mM EDTA, and 5 mM 2-mercaptoethanol, in a total volume of 100 $\mu$l, at 37° C. for 1 hr. The reaction was terminated by adding SDS to 0.2% and EDTA to 15 mM, and the DNA was purified by digestion with 0.4 mg/ml proteinase K at 37° C. for 1 hr, followed by phenol extraction and ethanol precipitation. DNA molecules carrying $Cro^-$ mutations that were formed during the in vitro replication stage were detected in a subsequent bioassay step (Cohen-Fix et al., 1992), by transformation of an indicator strain, E. coli WBY11T (Barak et al, 1995), and plating on lactose-indicator plates containing kanamycin (70 $\mu$g/ml). Mutants were scored after an incubation period of 21 hr at 37° C. Under these conditions $Cro^-$ mutants yield dark-red colonies, whereas $Cro^+$ plasmids yield white colonies. Typically, each transformation plate contained a total of 3–4×$10^4$ colonies, and for each DNA sample, eight plates were plated. The mutation frequencies of pol V and pol III holoenzyme were obtained as an average of 8 and 15 experiments, respectively. Parallel reactions were performed to determine the amount of DNA synthesis. This was done under the same conditions, except that [$\alpha$-$^{32}$P]DTTP was included at 50 $\mu$M. Reaction products were analyzed by agarose gel electrophoresis followed by phosphorimaging.

Calculation of Mutation Frequency

The observed mutation frequency per gene was calculated by dividing the number of dark-red $Cro^-$ mutants by the total number of colonies on the plate. To obtain the actual mutation frequency, two corrections were made. (i) The subpopulation of the substrate that contained double-stranded cro transformed the indicator strain and led to the formation of $kan^R$ colonies, but did not contribute a significant number of $Cro^-$ mutants (see Table 3 below). To compensate for this, the mutation frequency obtained with each of the DNA polymerases was multiplied by 2. To check the accuracy of this correction factor, the gapped plasmid was pretreated with restriction nuclease EcoRI, which cuts within cro. Because ssDNA is resistant to EcoRI, all molecules in which cro is not in the gap are linearied, leaving only gapped circles with cro in the gap. When this DNA was used as a substrate to determine the frequencies of pol III holoenzyme and of pol V, mutation frequencies were obtained that were 2-fold higher than with substrate that was not pretreated. This validates the multiplication of mutations frequencies by 2. (ii) Whereas DNA synthesis by pol III holoenzyme led to essentially quantitative filling in of the single-stranded gap in the plasmid, the amount of DNA synthesis by pol V was 29.4% that of pol III holoenzyme (see FIG. 19). To correct for that, mutation frequencies obtained with pol V were divided further by 0.294. This correction was not required for reactions with pol I or pol II, which filled in the gaps essentially quantitatively (data not shown), similar to pol III holoenzyme. It should be noted that the use of these correction factors, although necessary, introduces some error in the final mutation frequencies. Therefore, although our conclusions are not affected, these numbers are not precise.

The frequencies of specific types of mutations per gene were calculated by multiplying the fraction of that type of mutation out of all sequenced mutants (taken from Table 4) by the overall mutation frequency (presented in Table 3). To estimate base substitution mutation frequency per nucleotide, the mutation frequency per gene was divided by 87, the number of mutable sites in cro. This number is based on sequence data from 600 $Cro^-$ mutants that were sequenced in the laboratory of the present inventors over the years that showed that 96%, of $Cro^-$ mutations mapped in the coding region, and they were distributed over 87 sites, representing 43% of the ORF. For frameshift, the number of mutable sites is the entire ORF (201 nucleotides).

DNA Sequence Analysis of the Mutants

Mutant colonies were picked and their plasmid contents were extracted. The sequence of the cro gene in these plasmids was determined by Biological Services Department of the Weizmann Institute of Science, Rehovot, Israel, by using automated DNA sequence analysis.

Treatment of the Gapped Plasmid with Uracil DNA N-Glycosylase and MutM Glycosylase/AP Lyase To eliminate from the gapped plasmid possible spontaneous lesions-i.e., abasic (AP) sites, uracil, and 8-oxoguanines-the gapped pOC2 was treated with uracil DNA N-glycosylase and MutM glycosylase/AP lyase before replication. The reaction mixture contained 26 nM gapped pOC2, 0.025 unit/$\mu$l uracil DNA N-glycosylase, 0.83 $\mu$M MutM, 0.1 M KCl, 1 $\mu$g/$\mu$l bovine gamma globulin, 20 mM Tris-HCl (pH 8.0), 10 mM NaCl, and 1 mM EDTA. The reaction was carried out at 37° C. for 30 min, after which it was terminated by phenol extraction, and the DNA was precipitated with ethanol.

RESULTS

Outline of the Experimental System

The replication fidelity of pol V was determined by using a fidelity assay (FIG. 18) in which mutations generated in a reporter gene during in vitro replication were analyzed by a subsequent bioassay. The substrate used was a gapped plasmid, carrying the phage λ cro reporter gene in the ssDNA region. The assay consisted of in vitro gap-filling replication with pol V (as a MBP-UmuC fusion protein), UmuD', RecA, and SSB or with pol III holoenzyme as a control. This was followed by methylation of the plasmid with dam methylase to prevent removal of in vitro generated mutations by in vivo mismatch repair during the propagation in the tester strain. The gap-filled and methylated DNA then was used to transform an indicator *E. coli* strain, in which Cro⁻ mutations were detected as dark-red colonies over a background of white Cro⁺ colonies (Cohen-Fix et al., 1992; Skaliter et al., 1992; Tomer et al., 1996).

Gap-Filling Replication by Pol V

In vitro gap-filling replication of the gapped plasmid with pol III holoenzyme led to efficient filling-in of the 350 nucleotide ssDNA gap. This is indicated by the strong reduction in the amount of the gapped-plasmid DNA band and the appearance of the nicked and covalently closed circular forms of the plasmid (FIG. 19, left panel). Similarly, pol V in the presence of UmuD', RecA, and SSB promoted gap-filling replication, but to a lesser extent, as indicated by the persistence of a fraction of the substrate (FIG. 19, left panel). To quantify differences in DNA synthesis promoted by the two DNA polymerases, the replication reactions were conducted in the presence of $\alpha$-$^{32}$P-radiolabeled dTTP. After replication, the substrates were fractionated by agarose gel electrophoresis, and the amount of radiolabel incorporated into the DNA was determined by phosphorimaging. It was found that DNA synthesis promoted by pol V, UmuD', RecA, and SSB amounted to 29.4% of that of pol III holoenzyme (FIG. 19, right panel).

Replication by Pol V is Error-Prone

The fidelity of the gap-filling replication reaction was determined by transforming an indicator strain with the replication products and scoring Cro⁻ mutant colonies on lactose-EMB plates. The plasmid replicated by pol III holoenzyme yielded a mutation frequency of 98×10⁻⁵ per gene, 12-fold higher than the nonreplicated, gapped DNA (8×10⁻⁵; Table 3). The intact untreated plasmid pOC2 gave even a lower mutation frequency of 0.9×10⁻⁵. Experiments performed with pol I or pol II yielded mutation frequencies of 138×10⁻⁵ and 148×10⁻⁵, respectively, indicating a similar fidelity of all three DNA polymerases in this assay system (Table 3).

TABLE 3

Frequency of Cro Mutations Generated During In Vitro Gap-Filling Replication

| Protein composition | Mutation frequency × 10⁻⁵ |
|---|---|
| Pol V (MBP-UmuC), UmuD', RecA, SSB | 2,325 ± 408 |
| Component omitted: | |
| UmuD' | 27 ± 12 |
| MBP-UmuC | 19 ± 2.6 |
| RecA | 25 ± 3.6 |
| SSB | 51 ± 12 |
| MBP-UmuC + MBP | 18 ± 3.4 |
| All proteins | 8 ± 4 |
| Pol III holoenzyme | 98 ± 36 |

TABLE 3-continued

Frequency of Cro Mutations Generated During In Vitro Gap-Filling Replication

| Protein composition | Mutation frequency × 10⁻⁵ |
|---|---|
| Pol III holoenzyme, UmuD', RecA, SSB | 81 ± 36 |
| Pol I | 138 ± 52 |
| Pol I, UmuD', RecA, SSB | 78 ± 12 |
| Pol II | 148 ± 40 |
| Pol II, UmuD', RecA, SSB | 65 ± 22 |

Gap-filling replication reactions were performed with the indicated proteins, after which the DNA products were introduced into an *E. coli* indicator strain and plated on lactose-eosin/methylene blue (EMB) plates. Mutant (dark-red) and wild-type (white) colonies were counted. Mutation frequency was calculated as described in the Experimental Procedures. Transformation of untreated intact pOC2 yielded a mutation frequency of 0.9 × 10⁻⁵.

When replication was conducted with pol V (as an MBP-UmuC fusion protein) in the presence of UmuD', SSB, and RecA, the overall Cro⁻ mutation frequency was 2,325×10⁻⁵, 24-fold higher than pol III holoenzyme. This frequency reflects primarily errors made by pol V during the replication reaction, because its omission from the reaction led to a drastic 122-fold decrease in mutation frequency (19×10⁻⁵; Table 3). In Example 2, it was shown that gap-filling replication by pol V requires UmuD', RecA, and SSB. Similarly, the formation of Cro⁻ mutations during the in vitro reaction required all components: omission of each of pol V, UmuD', RecA, or SSB abolished the increase of mutagenesis (Table 3). Using the MBP tag instead of the MBP-UmuC protein also abolished the mutagenic effect (Table 3). Addition of UmuD', RecA, and SSB to pol I, pol II, or pol III holoenzyme did not decrease the fidelity of these DNA polymerases in the gap-filling assay (Table 3). This shows that pol V could not be replaced by any of these DNA polymerase, suggesting that the effect of UmuD', RecA, and SSB is specific to pol V. These results on the error-prone nature of pol V are consistent with those of Tang et al. (Tang et al., 1998), who recently reported that a purified UmuD'₂C complex promoted misinsertion during DNA synthesis.

Pol V-Generated Mutations are Mainly Transversions

DNA sequence analysis of 214 mutants was performed to examine the specificity of the in vitro generated mutations. It was found that pol III holoenzyme produced transitions, transversions, and frameshifts, together with more complex events, mostly deletions (FIG. 20; Table 4). The major class of mutation generated by pol III holoenzyme was frameshift mutation (45% of the point mutations; Tables 4 and 5), which was formed with an average frequency of 1.4×10⁻⁶ per nucleotide (Table 5). A dominance of frameshifts among mutations generated by pol III holoenzyme was observed recently in two other systems based on the lacI (Pham et al., 1998) and rpsL (Fujii et al., 1999) reporter genes. The frequency of base-substitution mutations generated by pol III homoenzyme in this system was 33.1×10⁻⁵ per gene or approximately 3.8×10⁻⁶ per nucleotide. This is made up of transitions at 2.1×10⁻⁶ per nucleotide and transversion at 1.7×10⁻⁶ per nucleotide (Table 5). The mutagenic specificity of pol III holoenzyme remained essentially unchanged when replication was performed with pol III holoenzyme in the presence of SSB and RecA (data not shown).

TABLE 4

Mutations Generated in the Cro Gene During
In vitro Gap-Filling Replication

| | No. of mutations | | |
|---|---|---|---|
| Mutation type | Pol III† | Pol V‡ | No polymerase§ |
| Base substitution | 24 | 72 | 42 |
| Frameshift | 20 | 20 | 0 |
| Other¶ | 27 | 9 | 0 |
| All mutants | 71 | 101 | 42 |
| Transition | 13 | 23 | 27 |
| A → G | 0 | 0 | 1 |
| C → T | 11 | 5 | 24 |
| G → A | 2 | 2 | 1 |
| T → C | 0 | 16 | 1 |
| Transversion | 11 | 49 | 15 |
| A → C | 2 | 7 | 2 |
| A → T | 0 | 18 | 0 |
| C → A | 0 | 4 | 0 |
| C → G | 0 | 1 | 2 |
| G → C | 5 | 5 | 8 |
| G → T | 2 | 1 | 3 |
| T → A | 2 | 10 | 0 |
| T → G | 0 | 3 | 0 |

Gap-filling replication reactions were performed with the indicated DNA polymerases, after which the DNA products were introduced into an *E. coli* indicator strain and plated on lactose-EMB plates. Plasmids were extracted from dark-red mutant colonies, and the sequence of their cro gene was determined by DNA sequence analysis. The details are presented in the Experimental Procedures.
† Replication was performed with pol III holoenzyme.
‡ Replication with pol V, in the presence of UmuD', RecA and SSB.
§ Nonreplicated gapped plasmid was used to transform the indicator strain.
¶ Other mutations include big deletions and insertions as well as complex mutations.

TABLE 5

Frequency of Major Classes of Mutations Generated During In Vitro Gap-Filling
Replication by pol III Holoenzymes and by pol V

| | Mutation frequency × $10^{-5}$ per cro gene | | Mutation frequency × $10^{-5}$ per nucleotide | | |
|---|---|---|---|---|---|
| Mutation | Pol III | Pol V | Pol III | Pol V | Pol V/Pol III |
| Base substitution | 33.1 | 1/657 | 0.38 | 19.0 | 50 |
| Transition | 17.9 (30%) | 529 (25%) | 0.21 | 6.1 | 30 |
| Transversion | 15.2 (25%) | 1,1278 (53%) | 0.17 | 13.0 | 74 |
| Frameshift | 27.6 (45%) | 460 (22%) | 0.14 | 2.3 | 17 |
| Total point mutations | 60.7 | 2,118 | 0.52 | 21.3 | 35/41* |

Mutation frequency per cro gene was calculated based on the data presented in Tables 3 and 4. Mutation frequency per nucleotide was calculated by dividing the mutation frequency per gene by the number of mutable sites (87 for base substitution and 201 for frameshift), as described in the Experimental Procedures.
*The ratio is 35 for mutation frequency per gene and 41 for mutation frequency per nucleotide. The difference stems from the fact that the number of mutable sites is different for base substitutions and frameshifts.

When replication was performed with pol V in the presence of RecA, UmuD', and SSB, the frequency of all types of mutations was much higher compared with pol III holoenzyme. The most dramatic difference was in transversion mutations, which were generated by pol V at a frequency 74-fold higher than pol III holoenzyme, reaching an average value of 1.13% per gene or $13.0 \times 10^{-5}$ per nucleotide (FIG. 20; Tables 4 and 5). Also, other types of mutation were higher: transitions were 30-fold higher (0.53% per gene; $6.1 \times 10^{-5}$ per nucleotide), and frameshifts were 17-fold higher (0.46% per gene; $2.3 \times 10^{-5}$ per nucleotide) than with pol III holoenzyme. The control nonreplicated gapped pOC2 produced a distinct spectrum composed of exclusively base substitutions, of which 64% were transitions, mostly (89%) C→T (Table 4).

Analysis of the mutational spectra revealed that the most pronounced differences in specificity between the two polymerases were in the formation of A-A, T-G, T-T, C-T, A-G, and T-C mismatches (the template nucleotides are underlined), which were formed by pol V at frequencies 49- to 296-fold higher than by pol III holoenzyme (Table 6). The types of mismatches formed in DNA most frequently by pol V (≈0.1–0.4% per cro gene each) were A-A≈T-G>T-T>A-G>G-G≈C-A≈C-T (Table 6).

TABLE 6

Frequency of specific types of base substitution mutations
generated during in vitro gap-filling
replication by pol V and by pol III holoenzyme

| | | Mutation frequency × $10^{-5}$ per gene | | |
|---|---|---|---|---|
| Mutation | Mismatch* | Pol III | Pol V | Pol V/Pol III |
| Transition | | | | |
| A → G | A-C | <1.4 | <23.0 | — |
| C → T | C-A | 15.2 | 115.1 | 8 |
| G → A | G-T | 2.8 | 46.0 | 16 |
| T → C | T-G | <1.4 | 368.3 | >263 |
| Transversion | | | | |
| A → C | A-G | 2.8 | 161.1 | 58 |
| A → T | A-A | <1.4 | 414.4 | >296 |
| C → A | C-T | <1.4 | 92.1 | >66 |
| C → G | C-C | <1.4 | 23.0 | >16 |

TABLE 6-continued

Frequency of specific types of base substitution mutations
generated during in vitro gap-filling
replication by pol V and by pol III holoenzyme

| Mutation | Mismatch* | Mutation frequency × $10^{-5}$ per gene | | |
|---|---|---|---|---|
| | | Pol III | Pol V | Pol V/Pol III |
| G → C | G-G | 6.9 | 115.1 | 17 |
| G → T | G-A | 2.8 | 23.0 | 8 |
| T → A | T-T | 2.8 | 230.2 | 82 |
| T → G | T-C | <1.4 | 69.1 | >49 |

Mutation frequency was calculated based on the data in Tables 3 and 4. The mismatches formed most frequently by pol V, and their frequencies are underlined. The largest differences between pol V and pol III holoenzyme are in boldface type.
*The mismatches that gave rise to the observed mutations. The template nucleotide in each pair is shown first.

The gapped cro gene contains a run of seven T residues (FIG. 20; nucleotides 119–125), which was a mutational hot spot for both pol III holoenzyme and pol V. Eighteen of 101 mutations generated by pol V were located in this run, including 11 frameshifts and 7 base substitutions (FIG. 20). Five of the 71 mutations generated by pol III holoenzyme were located in this run, all of them frameshift mutations. The abundance of frameshift mutations in this T run is most likely due to slippage of the DNA polymerases (Strieisinger et al., 1966; Kunkel, 1990). A strong hot spot unique to pol V was located at the first nucleotide 5' to the T run, where 12 A→T transversions were found. Interestingly, none of the 71 pol III holoenzyme mutations mapped in this site. Long T runs were shown previously to cause pauses during DNA synthesis with purified DNA polymerases (Weisman-Shomer et al., 1989), events that might facilitate slippage or misinsertion. In addition, long A:T runs form bent DNA (Koo et al., 1986), and that might have affected misincorporation.

The Common Spontaneous DNA Lesions are not the Cause of the in Vitro Generated Mutations A critical question is whether the observed mutations result from translesion replication of spontaneous DNA lesions in the DNA, rather than from the infidelity of pol V. The most common spontaneous DNA lesions currently known are apurinic sites, 8-oxoguanine, and uracil (Lindahl, 1993; Friedberg et al., 1995). Based on their published rates of formation (Friedberg et al., 1995), no significant amount of spontaneous lesions was expected to accumulate. However, as a precaution, the gapped bNA was treated with purified uracil DNA N-glycosylase and the MutM glycosylase/AP lyase before replication. This combination of enzymes caused nicks in double-stranded DNA and in ssDNA at abasic sites, uracil, and 8-oxoguanine (Friedberg et al., 1995), as the laboratory of the present inventors have verified with substrates containing site-specific lesions (data not shown). Therefore, such a treatment of the gapped plasmid before replication was expected to cause linearization of plasmid molecules containing the most common spontaneous lesions. Because linear plasmid DNA transforms E. coli cells very poorly, the treatment was expected to eliminate substrate molecules carrying spontaneous lesions from the assay. It was found that the treatment did not reduce mutation frequency of the replicated DNA (data not shown), arguing against the involvement of the known spontaneous DNA lesions.

Another line of evidence against the involvement of the known spontaneous lesions in this system was the specificity of in vitro generated mutations. AP sites generate primarily G→T and A→T transversions, 8-oxoguanine produces primarily G→T transversions, and deamination of C produces C→T transitions (Friedberg et al., 1995). Of these three types of mutations, A→T was observed at a significant frequency, but, even so, it comprised only 18% of all mutants, and most of them were located at a single hot spot (position 118). In addition, two of the major mutational events promoted by pol V were at T residues (T→A and T→C; Tables 4 and 6), where no significant spontaneous DNA lesion is known to be formed. Taken together, these results suggest that DNA lesions are not responsible for the mutations generated during in vitro replication by pol V.

DISCUSSION

The gap-fillinG DNA replication by pol V, described above, is characterized by three elements: (i) it requires UmuD', RecA, and SSB (Table 3); (ii) it is highly mutagenic, generating point mutations (base substitutions and frameshifts) at a frequency 35-fold higher than pol III holoenzyme (Table 5); and (iii) it has a distinct mutational specificity, namely, the tendency to form transversions (Table 5 and 6). Whereas the spectrum of mutations generated by pol III holoenzyme was dominated by frameshifts (45%), the spectrum of pol V was dominated by transversion (53%). These features are similar to those of untargeted mutagenesis, a branch of SOS mutagenesis that occurs at undamaged DNA regions, also termed SOS mutator activity (Livneth et al., 1993; Witkin et al., 1974; Witkin et al., 1979; Fijalkowska et al., 1997; Friedberg et al., 1995). Chromosomal untargeted mutagenesis was shown to require UmuC (pol V), UmuD', and RecA (Witkin, 1976; Witkin, 1974; Witkin et al., 1979; Ciesla, 1982; Fijalkowska et al., 1997) and produced preferentially transversion mutations (Fijalkowska et al., 1997; Miller et al., 1984; Yatagai et al., 1991; Watanabe-Akanuma et al., 1997). These similarities suggest that replication of undamaged DNA by pol V, UmuD' RecA and SSB is the mechanistic basis for SOS untargeted mutagenesis.

Under which circumstances might pol V produce mutations during SOS. It is possible that pol V acts in ssDNA gaps that are formed during DNA transactions in SOS-induced cells. Such gaps may be formed even in the absence of DNA damage, e.g., when replication is interrupted at some higher-order structures in DNA, or during the processes of recombination or transposition. In addition, pol V may produce mutations in the vicinity of lesions. Thus, when the replication fork is blocked at a DNA lesion, pol V, which is recruited to perform lesion bypass, might proceed well beyond the lesion, leading to an increased frequency of mutations downstream to the lesion (hitchhiking mutations; Ruiz et al., 1987).

The mutagenic DNA synthesis by pol V generates base pair mismatches, which might be substrates for the mismatch repair (MMR) system. Indeed, it was shown previously that in mutants defective in MMR, SOS untargeted mutations were higher than in MMR-proficient cells, indicating that untargeted mutations are subjected to mismatch correction (Fijalkowska et al., 1997; Caillet-Fauquet et al., 1984). Interestingly, this increase was mainly in transition, not transversion mutations (Fijalkowska et al., 1997). MMR is very effective in preventing transition mutations (i.e., correcting purine-pyrimidine mismatches) and frameshifts, but it is less efficient in preventing transversions (i.e., correcting purine-purine or pyrimidine-pyrimidine mismatches) (Fijalkowska et al., 1997; Schaaper et al., 1987; Schaaper, 1993). This specificity of MMR is well suited to correct replication errors, because the replicative polymerase, pol III holoenzyme, produces primarily frameshifts and transitions (75% of all point mutations; Table 5 see also Pham et al., 1998; Fujii et al., 1999; and Schaaper, 1993). In addition to transversions, pol V also generates in vitro mismatches, which lead to transitions and frameshifts at high frequencies (Tables 5 and 6). When this occurs in the cell under in vivo SOS conditions, these mismatches are likely to be repaired by MMR. Thus, the net result of the activities of pol V and MMR would be to generate transversion mutations with a specificity higher than expected based solely on the fidelity of pol V. That pol V generates mutations that can escape mismatch repair is consistent with the notion that SOS has evolved as a means of increasing genetic diversity under stress, thereby accelerating adaptation of bacterial populations to hostile environments (Witkin et al., 1979; Radman, 1975; Echols, 1981).

EXAMPLE 4

Plasmid-Encoded MucB Protein is a DNA Polymerase (pol RI) Specialized for Lesion Bypass in the Presence of MucA', RecA and SSB Replication through damaged sites in DNA requires in *E. coli* the SOS stress-inducible DNA polymerase V (UmuC), which is specialized for lesion bypass. Homologues of the umuC gene were found on native conjugative plasmids, which often carry multiple antibiotics-resistance genes. MucB is a UmuC homologue present on plasmid R46, and its variant plasmid pKM101 has been introduced into Salmonella strains for use in the Ames test for mutagens. Utilizing a translesion replication assay based on a gapped plasmid carrying a site-specific synthetic abasic site in the ssDNA region as described in detail below, it was shown that MucB is a DNA polymerase, termed pol RI, which is specialized for lesion bypass. The activity of pol RI requires the plasmid-encoded MucA' protein, and the *E. coli* RecA and single-strand DNA binding proteins Elimination of any of the proteins from the reaction abolished lesion bypass and polymerase activity. The unprocessed MucA could not substitute for MucA' in the bypass reaction. The presence of a lesion bypass DNA polymerase on a native conjugative plasmid, which has a broad host range specificity, and carries multiple antibiotics resistance genes, raises the possibility that mutagenesis caused by pol RI plays a role in the spreading of antibiotics resistance among bacterial pathogens.

The experiments in this example were conducted according to the Experimental Procedures described below.

EXPERIMENTAL PROCEDURES

Proteins

MucB, MucA' and MucA (Sarov-Blat et al., 1998), and the fusion MBP-UmuC protein and UmuD' were purified as previously described in Examples 1 and 2 and in Reven et al. (1998 and 1999). SSB and RecA were purified according to published procedures (Lohman et al., 1985 and Cox et al., 1981), respectively, except that a phosphocellulose purification step was added for RecA. Restriction nucleases, T4 DNA ligase and T4 polynucleotide kinase were from New England Biolabs (Beverly, Mass.). T7 gp6 exonuclease was from Amersham (Piscataway, N.J.), and S1 nuclease was from Promega (Madison, Wis.). Although the DNA sequence of the genetically engineered mucA' gene (SEQ ID NO:30) starts with an ATG codon, the methionine residue is not found in the overproduced and purified MucA' protein (SEQ ID NO:31). Presumably it is removed in vivo (Sarov-Blat, 1998).

DNA substrates

The preparation of the gapped plasmid carrying a site-specific lesion was recently described (Tomer et al., 1998a and Tomer et al., 1999b). Gapped plasmid GP21 contained a site-specific synthetic (tetrahydrofuran) abasic site, and a ssDNA region of approximately 350 nucleotides (FIG. 21).

Translesion Replication Assay

The translesion replication reaction was performed essentially as previously described in Examples 1 and 2 and in Reuven et al. (1998 and 1999), except that MucA' and MucB were used instead of UmuD' and UmuC. The reaction mixture (25 µl) contained 20 mM Tris.HCl pH 7.5, 8 mg/ml bovine serum albumin, 5 mM DTT, 0.1 mM EDTA, 4% glycerol, 1 mM ATP, 10 mM $MgCl_2$, 0.1 mM each of dATP, dGTP, dTTP and dCTP, 50 ng (1 nM) gapped plasmid, 600 nM SSB, 4 µM RecA, 2.5 µM MucA', and 50–300 nM MucB. When used, MucA was at 1.5–5.0 µM. Reactions were carried out at 37° C. for various periods of time. Analysis of the bypass products was done as described (Reuven et al., 1999). Briefly, the reaction mixture was treated with proteinase K, followed by phenol/chloroform extraction and ethanol precipitation. The DNA was then treated with calf intestine alkaline phosphatase to hydrolyze remaining dNTPs, after which the DNA was digested with Asp700 and MspA1I (FIG. 21). The DNA samples were fractionated by 15% PAGE-urea, followed by phosphorimager analysis (Fuji BAS 2500). The extent of bypass was calculated by dividing the amount of bypass products by the amount of the extended primers.

RESULTS

MucB, MucA' and MucA were previously overproduced, purified in denatured form, and refolded (Sarov-Blat et al., 1998). With the development of an effective lesion bypass in vitro assay system (Examples 1 and 2; Reuven et al., 1998 and 1999), and the finding that UmuC is a lesion bypass DNA polymerase (Example 2; Tang et al., 1999 and Reuven et al., 1999), the possibility that MucB is also a DNA polymerase was explored. The experimental bypass assay system was previously described (Reuven et al., 1998 and Tomer et al., 1998a). Briefly, the DNA substrate consists of a gapped plasmid carrying a site-specific synthetic abasic site in the ssDNA region, and an internal radiolabeled phosphate in the primer strand (FIG. 21). Upon addition of a DNA polymerase the 3' primer terminus is extended up to the abasic site. Lesion bypass will yield extension past the lesion, with the formation of a longer nascent DNA strand. To facilitate analysis, after termination of the reaction, the DNA products were extracted, and restricted with MspA1I, which cleaves 4 nucleotides upstream the radiolabel, and with Asp700, which cleaves downstream to the lesion. This yielded radiolabeled DNA fragments of 19, 29 and 47 nucleotides long, for the uninitiated primer, the nascent strand blocked at the lesion, and the bypass product, respectively (FIG. 21). These products were fractionated by urea-PAGE, and visualized and quantified by phosphorimaging.

Incubation of the gap-lesion plasmid with MucB in the presence of dNTPs and $Mg^{+2}$ did not reveal any polymerase activity, as indicated by the lack of extension of the DNA primer (FIG. 22A, lane 3). Therefore, MucB has very little or no polymerase activity on its own. Upon addition of MucA', RecA and SSB, there was a strong stimulation of DNA synthesis activity, indicating the activity of a DNA polymerase. This activity led to the extension of the radiolabeled primer up to the abasic site, and past it, generating the full length 47-nucleotides long product (FIG. 22A, lane 2). For comparison, FIG. 22B shows the activity of DNA polymerase II (pol II) in the same assay system. Although primer utilization by pol II was high, polymerization was severely arrested at the abasic site, and very little lesion bypass was observed (FIG. 22B, lane 3), similar to previous results (Tomer et al., 1999). In contrast, initiation of primer extension by MucB, in the presence of MucA', RecA and SSB was low, but once DNA synthesis started, it showed little inhibition at the abasic site, leading to bypass of the abasic site (FIG. 22B, lane 2). When the two polymerases were mixed, there was generally little effect on lesion bypass, and in fact a slight inhibition was observed, probably due to competition between the polymerases for the primer terminus (FIG. 22B, lane 5). Omission of MucB from this mixture reduced bypass, suggesting that the stimulation of bypass caused by MucA', RecA and SSB, is specific to MucB (FIG. 22B, lane 4).

A time course of translesion replication by MucB, MucA', RecA and SSB revealed that 28% of the molecules on which DNA synthesis was initiated, showed lesion bypass within 5 min (FIG. 23). For comparison, the bypass reaction was performed with UmuC, UmuD' RecA and SSB (FIG. 23). As can be seen, the two systems show generally similar results. The number of initiations in the Pol V reaction was higher than with MucB, and therefore the bands of all the extended primer are stronger than with MucB. However, when the extent of lesion bypass is calculated out of the initiated products, it is in fact slightly lower than with MucB. These results indicate that MucB is indeed a DNA polymerase. Notice that there was little inhibition of DNA synthesis at the synthetic abasic site, indicating a high propensity to bypass the synthetic abasic site.

The experiment described in FIG. 23 was performed using 250 nM MucB. Titration of MucB to lower concentration showed bypass at concentrations as low as 50 nM (FIG. 24). In this context, it is interesting to note that the intracellular concentrations of MucA and MucB in constitutively SOS-induced cells were reported to be very high, approximately 60 $\mu$M and 20 $\mu$M, respectively (Venderbure et al., 1999). Similarly to what was seen in FIGS. 22A, 22B, 23A and 23B, there seem to be replication pauses up to the lesion; however, once the lesion is bypassed, the pauses in synthesis are largely reduced. At this point, the reason for this behavior is not known, except that it was also observed during bypass by pol III holoenzyme alone (Tomer et al., 1998 and 1999) and by pol V (Example 2, Reuven et al., 1999). It is possible that these polymerases can sense the downstream lesion as they are approaching it, leading to synthesis pauses.

In order to examine the requirement for each of the components, the lesion bypass experiments were performed under conditions in which single components were omitted, one at a time. As can be seen in FIG. 25, elimination of each of the components led to the abolition of lesion bypass, indicating that each of the four proteins was absolutely required for lesion bypass. In fact, DNA synthesis up to the lesion was also greatly reduced when any of the proteins was omitted. Thus, the MucB DNA polymerase is highly activated by MucA', RecA and SSB, which potentiate it as an effective lesion bypass DNA polymerase. MucB was termed DNA polymerase RI by the present inventors because it is the first polymerase encoded by a native R plasmid.

MucA' is obtained from MucA (SEQ ID NO:29), encoded by the nucleotide sequence of SEQ ID NO:28, by post-translational processing promoted by RecA (Perry et al., 1985 and Hauser et al., 1992). Whether or not lesion bypass could be promoted with MucA instead of MucA' was examined. As can be seen in FIG. 26, translesion replication was strongly reduced under these conditions. The residual bypass activity maybe attributed to residual MucA' present in the MucA preparation due to autocleavage of MucA (Sarov-Blat et al., 1998 and Hauser et al., 1992), and to cleavage of MucA promoted by RecA under our assay conditions (Sarov-Blat et al., 1998).

DISCUSSION

Homologues of UmuC and UmuD' were found to be present on native conjugative plasmids, which have a broad host range specificity (Woodgate et al., 1992). The interest in these plasmids stems from the fact that they often carry multiple antibiotics resistance genes, and that they are frequently found among bacterial pathogens. The MucA, MucA' and MucB proteins have previously been overexpressed and purified and it was shown in the laboratory of the present inventors that MucA' forms a homodimer, and that MucB interacts with SSB-coated ssDNA, and alters its conformation without inducing gross dissociation of SSB from DNA (Sarov-Blat et al., 1998). Here, the translesion replication system described in Example 1 was used in order to examine whether MucB is a DNA polymerase. Based on the data presented, MucB is indeed a lesion bypass DNA polymerase. It is termed DNA polymerase RI by the present inventors, since it is the first DNA polymerase encoded by the native conjugative R plasmids. It is the second known prokaryotic lesion bypass DNA polymerase, however, it is likely that the other bacterial and plasmidic homologues of UmuC are also DNA polymerases.

MucB is a dormant DNA polymerase. Its activation requires MucA', RecA and SSB. However, once activated it shows a high propensity to replicate a synthetic abasic site, which is known to severely block DNA polymerase I (Kunket et al., 1981; Sagher et al., 1983 and Paz-Elizur et al., 1997), DNA polymerase II (Tomer et al., 1999 and Paz-Elizur et al., 1996) and DNA polymerase III (Tomer et al., 1999). In this sense, the MucA'B system is a functional homologue of the UmuD'C. system. The activity of MucA', RecA and SSB in lesion bypass by pol RI remains to be elucidated. However, it is well established that RecA forms a helical nucleoprotein filament along single-stranded DNA, and that the assembly of this filament is stimulated by SSB (reviewed in (Roca et al., 1990 and Kowalczykowski et al., 1994)). Therefore, it is possible that pol RI acts on RecA-coated DNA. MucA' is known to interact with pol RI (Sarov-Blat et al., 1998) and with RecA (Frank et al., 1994). Therefore, its role may be to mediate the interaction between pol RI and the RecA nucleoprotein filament. These, rather complex, requirements for lesion bypass by pol RI (and by pol V) may be required to achieve tight control over the activity of these polymerases.

The functional similarity of pol RI and pol V is manifested by the fact that the mucA'B operon complement a ΔumuDC mutant (Perry et al., 1982). In fact, mucA'B was reported to be more effective in promoting UV mutagenesis, as compared to umuD'C. (Blanco et al., 1986). This higher efficiency to promote mutagenesis was utilized in the Ames test for mutagens, where the tester strains carry plasmid pKM101, a natural variant of plasmid R46, which harbors mucAB (McCann et al., 1975). The reason for the higher effectiveness of MucB to promote mutagenesis is not clear yet, but it was attributed to a faster processing of MucA to MucA', as compared to UmuD processing to UmuD' (Hauser et al., 1992). Comparative bypass efficiencies by MucA'B and UmuD'C. was observed. However, it is difficult to draw conclusions from this comparison, since UmuC was purified in soluble form as a fusion to maltose binding protein in Example 1, whereas MucB was used without a tag, but was obtained by refolding of the denatured protein (Sarov-Blat et al., 1998). The greater effect of MucA'B may be attributed also to their higher level of expression in SOS-induced cells (Venderbure et al., 1999).

Based on the results presented above, pol RI is a functional homologue of pol V, and like pol V, it requires the host SSB and RecA proteins. Goodman and coworkers have reported that lesion bypass by a UmuD'C. complex required in addition to SSB and RecA, 6 additional proteins, which are subunits of DNA polymerase III holoenzyme: The β subunit processivity clamp, and the 5-subunit γ complex clamp loader (Tang et al., 1999). The present inventors have clearly obtained lesion bypass in the absence of these proteins, both with pol V (Reuven et al., 1999) and pol RI. Recently, Goodman and coworkers have reported that they could obtain bypass with pol V in the absence of β subunit and the γ complex, when they used ATPγS instead of ATP (Tang et al., 2000). ATPγS is known to stabilize RecA-ssDNA interactions (Roca et al., 1990). This suggests that the requirement for the β subunit and the γ complex was due to the inability to form a stable and functional RecA-ssDNA complex on the particular DNA substrate used in Goodman's studies. In that substrate, the lesion is located only 50 nucleotides from the 5' end of the DNA (Tang et al., 1998 and 1999). Since RecA assembly occurs in the 5'→3' direction (Roca et al., 1990), it may not fully cover the DNA 5' to the lesion, and this causes a difficulty for the stable assembly of RecA near the lesion. In the substrate used in our studies, there is no problem of loading of RecA since the DNA is circular, and the ssDNA region extends over 300 nucleotides 5' to the lesion. Taken together, it is clear that the basic lesion bypass reaction requires in vitro UmuD'C. or MucA'B, as well as SSB and RecA, and no other proteins. However, it is possible that the processivity proteins increase the efficiency of the lesion bypass reaction, e.g., by increasing the efficiency of initiation of at the primer terminus. Alternatively, the processivity proteins may be required under special conditions, or in a different Umu-promoted reaction, e.g., a DNA damage checkpoint activity (Opperman et al., 1999 and Sutton et al. 1999).

The presence of a lesion bypass polymerase on a native conjugative plasmid is intriguing. Having a limited size, such plasmids are expected to carry only genes with an unusual importance for the propagation of the plasmids in host cells. Why would lesion bypass proteins be selected to reside on plasmids? At least two answers come to mind: (1) Lesion bypass may represent a generic and simple, even 'primitive' mode of 'DNA repair'. It enables the preservation of the continuity of the plasmid, even when it is damaged, by using replication readthrough, without actually removing the lesion. (2) Lesion bypass is usually associated with mutagenesis. The mutagenesis function may be beneficial for a plasmid which is transmitted among a broad range of bacterial hosts, by allowing faster adaptation to foreign intracellular environments. A similar inducible mutator function for cellular adaptation was suggested for pol V (Radman et al., 1975; Witkin et al., 1979 and Echols, 1981). Since these plasmids often carry multiple antibiotics resistance genes, the mucAB genes and their homologues, may play an role in the spreading of antibiotics resistance among bacterial pathogens, a phenomenon which is becoming a growing threat to human health (Davies, 1994; Dennesen et al., 1998; Swatz et al., 1994 and O'Brien, 1997).

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Barak et al., "Deamination of cytosine-containing pyrimidine photodimers in UV-irradiated DNA. Significance for UV light mutagenesis" *J Biol Chem.*, 270:24174–24179 (1995)

Barzilai, "SV40 DNA: quantitative conversion of closed circular to open circular form by an ethidium bromide-restricted endonucleases" *J Mol Biol.*, 74:739–742 (1973)

Blanco et al., "Different efficiency of UmuDC and MucAB proteins in UV light induced mutagenesis in *Escherichia coli*", *Mol. Gen. Genet.*, 205:234–239 (1986)

Boudsocq et al., "Quantitation of the Inhibition of Hfr x F-Recombination by the Mutagenesis Complex UmuD'C." *J. Mol. Biol.*, 270:201–211 (1997)

Bridges et al., "Mutagenic DNA Repair in *Escherichia coli*. XVII. Involvement of DNA Polymerase III α-subunit (DnaE Protein) in Mutagenesis after Exposure to UV Light" *Mutagenesis*, 5:35–38 (1990)

Bridges, "DNA Polymerase and Mutation" *Nature*, 275:591–592 (1978)

Bridges et al., "Mutagenic DNA Repair in *E. coli*. III. Requirement for a Function of DNA Polymerase III in Ultraviolet Light Mutagenesis" *Mol. Gen. Genet.*, 144:53–58 (1976)

Brotcome-Lannoye et al., "Role of RecA Protein in Untargeted UV Mutagenesis of Bacteriophage λ: Evidence for The Requirement of The dinB Gene" *Proc. Natl. Acad. Sci. USA*, 83:3904–3908 (1986)

Brotcome-Lannoye et al., "Involvement of DNA polymerase III in UV-Induced Mutagenesis of Bacteriophage λ." *Mol. Gen. Genet.*, 199:64–69 (1985)

Bruck et al., "Purification of a Soluble UmuD'C. complex from *Escherichia coli*. Cooperative Binding of UmuD'C. to Single-Stranded DNA" *J. Biol. Chem.*, 271:10767–10774 (1996)

Burckhardt et al., "UmuD Mutagenesis Protein of *Escherichia coli*: Overproduction, Purification, and Cleavage by RecA" *Proc. Natl. Acad. Sci. USA*, 85:1811–1815 (1988)

Caillet-Fauquet et al., "SOS mutator effect in *E. coli* mutants deficient in mismatch correction" *EMBO J.*, 3:707–712 (1984)

Caillet-Fauquet et al., "Nature of the SOS mutator activity: genetic characterization of untargeted mutagenesis in *Escherichia coli*" *Mol. Gen. Genet.*, 213:491–498 (1988)

Ciesla, "Plasmid pKM101-mediated mutagenesis in *Escherichia coli* is inducible" *Mol Gen Genet.*, 186(2):298–300 (1982)

Cohen-Fix et al., "Biochemical Analysis of UV Mutagenesis in *Escherichia coli* by Using A Cell-Free Reaction Coupled to a Bioassay: Identification of A DNA repair-Dependent, Replication-Independent Pathway" *Proc. Natl. Acad. Sci. USA* 89:3300–3304 (1992)

Cohen-Fix et al., "In vitro UV mutagenesis associated with nucleotide excision-repair gaps in *Escherichia coli J Biol Chem.*, 269:4953–4958 (1994)

Cox et al., "A Simple and Rapid Procedure for the Large Scale Purification of the recA Protein of *Escherichia coli*" *J. Biol. Chem.*, 256:4676–4678 (1981)

Cull et al., "Purification of *Escherichia coli* DNA Polymerase III Holoenzyme" *Methods Enzymol.*, 262:22–35 (1995)

Davies, "Inactivation of antibiotics and the dissemination of resistance genes", *Science*, 264:375–382 (1994)

Dennesen et al., "Multiresistant bacteria as a hospital epidemic problem", *Ann. Med.*, 30:176–185 (1998)

Dutreix et al., "New recA Mutations that Dissociate the Various RecA Protein Activities in *Escherichia coli* Provide Evidence for an Additional Role for RecA Protein in UV Mutagenesis" *J. Bacteriol.*, 171:2415–2423 (1989)

Echols, "SOS Functions, cancer, and Inducible Evolution" *Cell*, 25:1–2 (1981)

Echols et al., "Fidelity mechanisms in DNA replication", *Annu. Rev. Biochem.*, 60:477–511 (1991)

Efrati et al., "Abasic translesion Synthesis by DNA Polymerase β Violates the "A-Rule." *J. Biol. Chem*, 272:2559–2569 (1997)

Eggleston et al., "Exchanging Partners: Recombination in *E. coli*" *Trends Genet.*, 12:20–26 (1996)

El-Deiry et al., "Molecular mechanisms of manganese mutagenesis" *Proc. Natl. Acad. Sci. USA*, 81:7378–7382 (1987)

Fijalkowska et al., "Genetic Requirements and Mutational Specificity of the *Escherichia coli* Mutator Activity" *J. Bacteriol.*, 179:7435–7445 (1997)

Frank et al., "Targeting of the UmuD, UmuD', and MucA' mutagenesis proteins to DNA by RecA protein", *Proc. Natl. Acad. Sci. USA*, 90:8169–8173 (1993)

Friedberg et al., "DNA Repair and Mutagenesis" Washinqton, D.C.: *ASM Press* (1995)

Fujii et al., "DNA replication errors produced by the replicative apparatus of *Escherichia coli*" *J Mol Biol.*, 289:835–850 (1999)

Gibbs et al., "The function of the human homolog of *Saccharomyces cerevisiae* REV1 is required for mutagenesis induced by UV light", *Proc. Natl. Acad. Sci. USA*, 97:4186–4191 (2000)

Gibbs, et al., "A Human Homolog of the *Saccharomyces cerevisiae* REV 3 Gene, which Encodes the Catalytic Subunit of DNA Polymerase ζ" *Proc. Natl. Acad. Sci. USA*, 95:6876–6880 (1998)

Hanks et al., "Protein Kinase Catalytic Domain Sequence Database: Identification of Conserved Features of Primary Structure And Classification of Family Members" *Methods Enzymol.*, 200:38–62 (1991)

Hauser et al., "The enhanced mutagenic potential of the MucAB proteins correlates with the highly efficient processing of the MucA protein", *J. Bacteriol.*, 174:6844–6851 (1992)

Hevroni et al., "Bypass and Termination at Apurinic Site During Replication of Single-Stranded DNA In vitro: A Model for Apurinic Site Mutagenesis" *Proc. Natl. Acad. Sci. USA*, 85:5046–5050 (1988)

Johnson et al., "hRAD30 mutations in the variant form of xeroderma pigmentosum", *Science*, 285:263–265 (1999)

Johnson et al., "The human DINB1 gene encodes the DNA polymerase Poltheta", *Proc. Natl. Acad. Sci. USA*, 97:3838–3843 (2000)

Johnson et al., "Efficient Bypass of A Thymine-Thymine Dimer by Yeast DNA Polymerase η" *Science* 283:1001–1004 (1999a)

Johnson et al., "Requirement of DNA Polymerase Activity of Yeast Rad30 Protein for its Biological Function" *J. Biol. Chem.*, 274:15975–15977 (1999b)

Joyce et al., "DNA polymerase I: from crystal structure to function via genetics", *Trends Biochem. Sci.*, 12:288–292 (1987)

Kato et al., "Isolation and Characterization of Mutants of *Escherichia coli* Deficient in Inducing of Mutagenesis by Ultraviolet Light" *Mol. Gen. Genet.*, 156:121–131 (1977)

Kenyon et al., "DNA-Damaging Agents Stimulate Gene Expression at Specific Loci in *Escherichia coli*" *Proc. Natl. Acad. Sci. USA*, 77:2819–2823 (1980)

Kim et al., "Multiple Pathways for SOS-Induced Mutagenesis in *Escherichia coli*: An Overexpression of dinB/dinP Results in Strongly Enhancing Mutagenesis in the Absence of Any Exogenous Treatment to Damage DNA" *Proc. Natl. Acad. Sci. USA* 94:13792–3797 (1997)

Koch et al., "*Escherichia coli* umuDC Mutants: DNA Sequence Alterations and UmuD Cleavage" *Mol. Gen. Genet.*, 233:443–448 (1992)

Koo et al., "DNA bending at adenine thymine tracts" *Nature*, 320:501–506 (1986)

Kornberg et al., "DNA Replication" W. H. Freeman and Company, New York (1991)

Kowalczykowski et al., "Biochemistry of Homologous Recombination in *Escherichia coli*" *Microbiol. Rev.*, 58:401–465 (1994)

Kulaeva et al., "Identification of a DinB/UmuC Homolog in the Archean *Sulfolobus solfataricus*" *Mutation Res.* 357:245–253 (1996)

Kulaeva et al., "Characterization of the umu-complementing Operon from R391" *J. Bacteriol.*, 177:2737–2743 (1995)

Kunkel, "Mutational Specificity of depurination" *Proc. Natl. Acad. Sci. USA*, 81:1494–1498 (1984)

Kunkel, "Misalignment-Mediated DNA Synthesis Errors" *Biochemistry*, 29:8003–8011 (1990)

Kunkel et al., "Mutagenesis in vitro by depurination of phiX174 dna", Nature, 291:349–351 (1981)

Ichikawa-Ryo et al., "Indirect mutagenesis in phage lambda by ultraviolet preirradiation of host bacteria" *J Mol Biol.*, 97(1):77–92 (1975)

Larson et al., "Influence of template strandedness on in vitro replication of mutagen-damaged DNA", *Biochemistry*, 26:2471–9

Lawrence et al., "The RAD6 DNA Repair Pathway in *Saccharomyces cerevisiae*: What Does it Do And How Does it Do it?" *Bioessays*, 16:253–258 (1994)

Lawrence et al., "Mutation Frequency and Spectrum Resulting from a Single Abasic Site in a Single-Stranded Vector" *Nucleic Acids Res.*, 18:2153–2157 (1990)

Lin et al., "The human REV1 gene codes for a DNA template-dependent dCMP transferase", *Nucleic Acids Res.*, 27:4468–4475 (1999)

Lindahol, "Instability and decay of the primary structure of DNA" *Nature*, 362:709–715 (1993)

Livneh, "Mechanism of Replication of Ultraviolet-Irradiated Single-Stranded DNA by DNA polymerase III Holoenzyme of *Escherichia coli* Implications for SOS Mutagenesis" *J. Biol. Chem.*, 261:9526–9533 (1986)

Livneh et al., "Replication of Damaged DNA and the Molecular Mechanism of Ultraviolet Light Mutagenesis" *Crit Rev. Biochem. Mol. Biol.*, 28:465–513 (1993)

Lodwick et al., "DNA Sequence Analysis of The imp UV Protection And Mutation Operon of The Plasmid TP110: Identification of A Third Gene" *Nucleic Acids Res.*, 18:5045–5050 (1990)

Loeb et al., "Mutagenesis by Apurinic/Apyrimidinic Sites" *Annu. Rev. Genet.*, 20:201–230 (1986)

Loeb et al., "Fidelity of DNA synthesis", *Annu. Rev. Biochem.*, 51:429–457 (1982)

Lohman et al., *J. Biol. Chem.*, 260:3594–3603 (1985)

Maenhaut-Michel et al., "Effect of umuC mutations on targeted and untargeted ultraviolet mutagenesis in bacteriophage lambda" *J Mol Biol.*, 177:181–187 (1984)

Maher et al., "Frequency of Ultraviolet Light-Induced Mutations Is Higher in Xeroderma Pigmentosum Variant Cells than in Normal Human Cells" *Nature*, 261:593–595 (1976)

Maor-Shoshani et al., "Highly mutagenic replication of undamaged DNA by DNA polymerase V (UmuC) provides a mechanistic basis for SOS untargeted mutagenesis", *Proc. Natl. Acad. Sci. USA*, 97:565–570 (2000)

Marsh et al., "Cold Sensitivity Induced by Over-Production of UmuDC in *Escherichia coli*" *J. Bacteriol.*, 162:155–161 (1985)

Matsutani et al., "The XPV (Xeroderma Pigmentosum Variant) Gene Encodes Human DNA Polymerase eta," *Nature* 399:700–704 (1999).

McCann et al., "Detection of carcinogens as mutagens: bacterial tester strains with R factor plasmids", *Proc. Natl. Acad. Sci. USA*, 72:979–983 (1975)

McDonald et al., "The *Saccharomyces cerevisiae* RAD30 gene, A Homologue of *Escherichia coli* dinB and umuC, is DNA Damage Inducible And Functions in A Novel Error-Free Postreplication Repair Mechanism" *Genetics*, 147:1557–1568 (1997)

McDonald et al., "Novel human and mouse homologs of *Saccharomyces cerevisiae* DNA polymerase eta", *Genomics*, 60:20–30 (1999)

Michaels et al., "Evidence for in vitro translesion DNA synthesis past a site-specific aminofluorene adduct", *J. Biol. Chem.*, 262:14648–54, (1987)

Mo et al., "Fidelity and Error Specificity of the α catalytic Subunit of *Escherichia coli* DNA Polymerase III" *J. Biol. Chem.*, 271:18947–18953 (1996)

Napolitano et al., "SOS Factors Involved in Translesion Synthesis" *Proc. Natl. Acad. Sci. USA*, 94:5733–5738 (1997)

Nelson et al., "Deoxycytidyl transferase Activity of Yeast REV1 Protein" *Nature*, 382:729–731 (1996a)

Nelson et al., "Thymine-thymine Dimer Bypass by Yeast DNA Polymerase ζ" *Science*, 272:1646–1649 (1996b)

Nohmi et al., "*Salmonella typhimurium* has Two Homologous but Different umuDC Operons: Cloning of A New umuDC-Like Operon (samAB) Present in A 60-Megadalton Cryptic Plasmid of *S. Typhimurium*" *J. Bacteriol.* 173:1051–1063 (1991)

Nohmi et al., "RecA-Mediated Cleavage Activates UmuD for Mutagenesis: Mechanistic Relationship Between Transcriptional Derepression and Post-Translational Activation" *Proc. Natl. Acad. Sci. USA*, 85:1816–1820 (1988)

O'Brien et al., "The global epidemic nature of antimicrobial resistance and the need to monitor and manage it locally", *Clin. Infect. Dis.*, 24 Suppl 1, S2–8 (1997)

Ohashi et al., "Error-prone bypass of certain DNA lesions by the human DNA polymerase kappa *Genes Dev.*, 14:1589–1594 (2000)

Opperman et al., "A model for a umuDC-dependent prokaryotic DNA damage checkpoint", *Proc. Natl. Acad. Sci. USA*, 96:9218–9223 (1999)

Paz-Elizur et al., "Mechanism of Bypass Synthesis Through an Abasic Site Analog by DNA Polymerase I" *Biochemistry* 36:1766–1773 (1997a)

Paz-Elizur et al., "Anti-Mutagenic Activity of DNA-Damage Binding Proteins Mediated by Direct Inhibition of Translesion Replication" *J. Biol. Chem.*, 272:28906–28911 (1997b)

Paz-Elizur et al., "Mechanism of Translesion DNA Synthesis by DNA Polymerase II: Comparison to DNA Polymerase I and III" *J. Biol. Chem.* 271:24662–24669 (1996)

Pelletier et al., "Crystal structure of human DNA polymerase beta complexed with DNA. Implications for catalytic mechanism, processivity and fidelity", *Biochemistry*, 35:12742–12761 (1996)

Perry et al., "Identification of plasmid (pKM101)-coded proteins involved in mutagenesis and UV resistance", *Nature*, 300:278–281 (1982)

Perry et al., "UmuDC and mucAB Operons Whose Products are Required for UV Light- and Chemical-Induced Mutagenesis: UmuD, MucA, and LexA Proteins Share Homology" *Proc. Natl. Acad. Sci. USA* 82:4331–4335 (1985)

Petit et al., "Sequential Folding of UmuC by the Hsp70 and Hsp60 Chaperone Complexes of *Escherichia coli*" *J. Biol. Chem.*, 269:23824–23829 (1994)

Pham et al., "The base substitution and frameshift fidelity of *Escherichia coli* DNA polymerase III holoenzyme in vitro" *J Biol Chem.*, 273:23575–23584 (1998)

Radman, "SOS Repair Hypothesis: Phenomenology of an Inducible DNA Repair Which is Accompanied by Mutagenesis. In Molecular Mechanisms for Repair of DNA" New York: Academic Press, pp. 355–367 (1975)

Rajagopalan et al., "Activity of the Purified Mutagenesis Proteins UmuC, UmuD', and RecA in Replicative Bypass of an Abasic Site DNA Lesion by DNA Polymerase III" *Proc. Natl. Acad. Sci. USA*, 89:10777–10781 (1992)

Reuven et al., "The Mutagenesis Proteins UmuD' and UmuC Prevent Lethal Frameshifts While Increasing Base Substitution Mutations" *Mol. Cell*, 2:191–199 (1998)

Reuven et al., "The mutagenesis protein UmuC is a DNA polymerase activated by UmuD', RecA, and SSB and is specialized for translesion replication", *J. Biol. Chem.*, 274:31763–31766 (1999)

Roca et al., "The RecA Protein: Structure and Function" *Crit. Rev. Biochem. Mol. Biol.*, 25:415–456 (1990)

Roush et al., "Deletion of the *Saccharomyces cerevisiae* Gene RAD30 Encoding an *Escherichia coli* DinB Homolog Confers UV Radiation Sensitivity and Altered Mutability" *Mol. Gen. Genet.*, 257:686–692 (1998)

Ruiz et al., "Mutagenic DNA repair in *Escherichia coli*. XIV. Influence of two DNA polymerase III mutator alleles on spontaneous and UV mutagenesis" *Mol Gen Genet.*, 208:542–548 (1987)

Sagher et al., "Insertion of nucleotides opposite apurinic/apyrimidinic sites in deoxyribonucleic acid during in vitro synthesis: uniqueness of adenine nucleotides", *Biochemistry*, 22:4518–4526 (1983)

Sancar, "Mechanisms of DNA Repair" *Science*, 266:1954–1956 (1994)

Sarov-Blat et al., "The Mutagenesis Protein MucB interacts with Single Strand DNA Binding Protein and Induces a Major conformational Change in its Complex with Single-Stranded DNA" *J. Biol. Chem.*, 273:5520–5527 (1998)

Schaaper et al., "Spectra of spontaneous mutations in *Escherichia coli* strains defective in mismatch correction: the nature of in vivo DNA replication errors" *Proc Natl Acad Sci USA.*, 84:6220–6224 (1987)

Schaaper, "Base selection, proofreading, and mismatch repair during DNA replication in *Escherichia coli*" *J Biol Chem.*, 268:23762–23765 (1993)

Sedgwick et al., "Mutagenic DNA Repair in Enterobacteria" *J. Bacteriol.*, 173:5604–5611 (1991)

Shinagawa et al., "RecA Protein-Dependent Cleavage of UmuD Protein and SOS Mutagenesis" *Proc. Natl. Acad. Sci. USA*, 85:1806–1810 (1988)

Skaliter et al., "Spontaneous transposition in the bacteriophage lambda cro gene residing on a plasmid" *Mutat Res.*, 267:139–151 (1992)

Smith et al., "Sequence Analysis and Mapping of the *Salmonella typhimurium* LT2 umuDC Operon" *J. Bacteriol.* 172:4964–4978 (1990)

Sommer et al., "The Appearance of the UmuD'C. Protein Complex in *Escherichia coli* Switches Repair from Homologous Recombination to SOS Mutagenesis" *Mol. Microbiol.*, 10:963–971 (1993)

Strauss, "Translesion DNA synthesis: polymerase response to altered nucleotide", *Cancer Surv.*, 4:493–516 (1985)

Steinborn, "Uvm Mutants of *Escherichia coli* K12 Deficient in UV mutagenesis" *Mol. Gen. Genet.*, 165:87–93 (1978)

Streisinger et al., "Frameshift mutations and the genetic code" *Cold Sprina Harb Symp Quant Biol.*, 31:77–84 (1966)

Strike et al., "Nature of Transforming Deoxyribonucleic Acid in Calcium-treated *Escherichia coli*" *J. Bacteriol.*, 138–1033–1035 (1979)

Sutton et al., "The *Escherichia coli* SOS mutagenesis proteins UmuD and UmuD' interact physically with the replicative DNA polymerase", *Proc. Natl. Acad. Sci. USA*, 96:12373–12378 (1999)

Swartz et al., "Hospital-acquired infections: diseases with increasingly limited therapies", *Proc. Natl. Acad. Sci. USA*, 91:2420–2427 (1994)

Sweasy et al., "RecA Protein of *Escherichia coli* has a Third Essential Role in SOS Mutator Activity" *J. Bacteriol*, 172:3030–3036 (1990)

Takeshita et al., "Oligodeoxynucleotides Containing Synthetic Abasic Sites. Model Substrates for DNA Polymerases and Apurinic/Apyrimidinic Endonucleases" *J. Biol. Chem.*, 262:10171–10179 (1987)

Tang et al., "Biochemical Basis of SOS-Induced Mutagenesis in *Escherichia coli*: Reconstitution of In Vitro Lesion Bypass Dependent on The UmuD'$_2$C Mutagenic Complex And RecA Protein" *Proc. Natl. Acad. Sci. USA*, 95:9755–9760 (1998)

Thompson et al., "CLUSTAL W: Improving The Sensitivity of Progressive Multiple Sequence Alignment Through Sequence Weighting, Position-Specific Gap Penalties And Weight Matrix Choice" *Nucleic Acids Res.*, 22:4673–4680 (1994)

Tissier et al., "poliota, a remarkably error-prone human DNA polymerase", *Genes Dev.*, 14:1642–1650 (2000)

Tomer et al., "Reconstitution of repair-gap UV mutagenesis with purified proteins from *Escherichia coli*: a role for DNA polymerases III and II" *Proc Natl Acad Sci USA.*, 93:1376–1380

Tomer et al., "The Beta Subunit Sliding DNA Clamp Is Responsible for Unassisted Mutagenic Translesion Replication by DNA Polymerase III Holoenzyme", *Proc. Natl. Acad. Sci. USA* 95:14106–14111 (1998).

Tomer et al., "Analysis of Unassisted translesion Replication by the DNA Polymerase III Holoenzyme" *Biochemistry* 38:5948–5958 (1999)

Venderbure et al., "Inhibition of homologous recombination by the plasmid MucA'B complex", *J. Bacteriol.*, 181:1249–1255 (1999)

Wagner et al., "The dinB Gene Encodes A Novel *Escherichia coli* DNA Polymerase (DNA pol IV) Involved in Mutagenesis", *Mol. Cell*, 4:281–286 (1999)

Walker, "SOS-Regulated Proteins in Translesion DNA Synthesis and Mutagenesis" *Trends Biochem. Sci.*, 20:416–420 (1995)

Wang et al., "Evidence from Mutation Spectra that The UV Hypermutability of Xeroderma Pigmentosum Variant Cells Reflects Abnormal, Error-Prone Replication on A Template Containing Photoproducts" *Mol. Cell Biol.*, 13:4276–4283 (1993)

Watanabe-Akanuma et al., "Enhanced generation of A:T→T:A transversions in a recA730 lexA51(Def) mutant of *Escherichia coli*" *Mutat Res.*, 373:61–66 (1997)

Weismann-Shomer et al., "Sequence specificity of pausing by DNA polymerase" *Biochem Biophys Res Commun.*, 164:1149–1156 (1989)

Witkin et al., "Targeted and untargeted mutagenesis by various inducers of SOS functions in *Escherichia coli*" *Cold Spring Harb Symp Quant Biol.*, 43:881–886 (1979)

Witkin, "Ultraviolet Mutagenesis and Inducible DNA Repair in *Escherichia coli*" *Bacteriol. Rev.*, 40:869–907 (1976)

Witkin, "Thermal enhancement of ultraviolet mutability in a tif-1 uvrA derivative of *Escherichia coli* B-r: evidence that ultraviolet mutagenesis depends upon an inducible function" *Proc Natl Acad Sci USA*, 71(5):1930–1934 (1974)

Witkin, "RecA Protein in the SOS Response: Milestones and Mysteries" *Biochimie*, 73:133–141 (1991)

Woodgate et al., "Damage Inducible Mutagenesis: Recent Insights into the Activities of the Umu Family of Proteins" *Cancer Surv.*, 28:117–140 (1996)

Woodgate et al., "UmuC Mutagenesis Protein of *Escherichia coli*: Purification and Interaction with UmuD and UmuD'" *Proc. Ncad. Sci. USA*, 6:7301–7305 (1989)

Woodgate et al., "Mutagenesis induced by bacterial UmuDC proteins and their plasmid homologues", *Mol. Microbiol.*, 6:2213–2218 (1992)

Xiao et al., "Identification, Chromosomal Mapping and Tissue-Specific Expression of hREV3 Encoding a Putative Human DNA Polymerase ζ" *Carcinogenesis*, 19:945–949 (1998)

Yatagai et al., "Specificity of recA441-mediated (tif-1) mutational events" *Mol Gen Genet.* 230:75–80 (1991).

---

What is claimed is:

1. A method for replicating a DNA molecule having DNA lesion damage, comprising:
   providing a sample containing a DNA molecule with one or more sites of DNA lesion damage; and
   contacting the DNA molecule with a translesion replication DNA polymerase, capable of replicating through DNA lesions and selected from the group consisting of UmuC (DNA polymerase V), a fusion protein of UmuC, a fragment of UmuC, and a prokaryotic homologue of UmuC, a fragment of the prokaryotic UmuC homologue, and a fusion protein of the prokaryotic UmuC homologue, in the presence of a combination of UmuD', RecA and SSB proteins, or in the presence of a combination in which at least one of the UmuD', RecA and SSB proteins is replaced by a functional prokaryotic homologue thereof, nucleoside 5'-triphosphates, and a divalent metal ion to replicate the damaged DNA molecule by replicating through the one or more sites of DNA lesion damage.

2. The method according to claim 1, wherein the prokaryotic homologues of UmuC, UmuD', RecA and SSB are from the same prokaryotic species.

3. The method according to claim 2, wherein the prokaryotic species is *Escherichia coli*.

4. The method according to claim 2, wherein the prokaryotic species is *Salmonella typhimurium*.

5. The method according to claim 2, wherein the prokaryotic species is *Providencia rettgeri*.

6. The method according to claim 2, wherein the prokaryotic species is *Sulfolobus solfataricus*.

7. The method according to claim 1, wherein the translesion replication DNA polymerase is a prokaryotic homologue of UmuC or a fragment thereof.

8. The method according to claim 7, wherein the prokaryotic homologue of UmuC is MucB and the prokaryotic homologue of UmuD' is MucA'.

9. The method according to claim 7, wherein the prokaryotic homologue of UmuC is selected from the group consisting of dinB from *Escherichia coli*, UmuC from *Salmonella typhimurium*, impB from *Salmonella typhimurium*, dbh from *Sulfolobus solfataricus*, rumB from *Providencia rettgeri*, and samB from *Salmonella typhimurium*.

10. The method according to claim 1, wherein the translesion replication DNA polymerase is a fusion protein of UmuC.

11. The method according to claim 10, wherein the fusion protein of UmuC is a fusion protein of UmuC and maltose binding protein.

12. The method according to claim 11, wherein the fusion protein of UmuC and maltose binding protein comprises the amino acid sequence of SEQ ID NO:5.

13. The method according to claim 1, wherein the translesion replication DNA polymerase is UmuC or a fragment thereof.

14. The method according to claim 13, wherein UmuC or a fragment thereof is contacted with the DNA molecule in the presence of UmuD', RecA and SSB.

15. The method according to claim 1, wherein the divalent metal ion is selected from the group consisting of $Mg^{+2}$, $Mn^{+2}$, $Zn^{+2}$, $Co^{+2}$, $Ni^{+2}$ and $Fe^{+2}$.

16. The method according to claim 1, wherein the divalent metal ion is $Mg^{+2}$.

17. A hybrid protein comprising a fusion of maltose binding protein and UmuC protein.

18. The hybrid protein according to claim 17, which comprises the amino acid sequence of SEQ ID NO:5.

19. A recombinant DNA molecule comprising a nucleotide sequence encoding the hybrid protein of claim 17.

20. The recombinant DNA molecule according to claim 19, wherein said nucleotide sequence comprises SEQ ID NO:4.

21. The recombinant DNA molecule according to claim 19, further comprising a self-replicating vector sequence.

22. A host cell transformed with the recombinant DNA molecule of claim 21.

23. A method for mutagenesis of a DNA molecule, comprising replicating a DNA molecule with a DNA polymerase selected from the group consisting of UmuC, a fusion protein of UmuC, a fragment of UmuC, a prokaryotic homologue of UmuC, a fragment of the prokaryotic UmuC homologue, and a fusion protein of the prokaryotic UmuC homologue, in the presence of a combination of UmuC', RecA and SSB proteins, or in the presence of a combination in which at least one of the UmuD', RecA and SSB proteins is replaced by a functional prokaryotic homologue thereof, nucleoside 5'-triphosphates, and a divalent metal ion to mutagenize the DNA molecule.

24. The method according to claim 23, wherein the prokaryotic homologues of UmuC, UmuD', RecA and SSB are from the same prokaryotic species.

25. The method according to claim 24, wherein the prokaryotic species is *Escherichia coli*.

26. The method according to claim 24, wherein the prokaryotic species is *Salmonella typhimurium*.

27. The method according to claim 24, wherein the prokaryotic species is *Providencia rettgeri*.

28. The method according to claim 24, wherein the prokaryotic species is *Sulfolobus solfataricus*.

29. The method according to claim 23, wherein the DNA polymerase is a prokaryotic homologue of UmuC or a fragment thereof.

30. The method according to claim 29, wherein the prokaryotic homologue of UmuC is MucB and the prokaryotic homologue of UmuD' is MucA'.

31. The method according to claim 29, wherein the prokaryotic homologue of UmuC is selected from the group consisting of dinB from *Escherichia coli*, UmuC from *Salmonella typhimurium*, impB from *Salmonella typhimurium*, dbh from *Sulfolobus solfataricus*, rumB from *Providencia rettgeri*, and samB from *Salmonella typhimurium*.

32. The method according to claim 23, wherein the DNA polymerase is a fusion protein of UmuC.

33. The method according to claim 32, wherein the fusion protein of UmuC is a fusion protein of UmuC and maltose binding protein.

34. The method according to claim 33, wherein the fusion protein of UmuC and maltose binding protein comprises the amino acid sequence of SEQ ID NO:5.

35. The method according to claim 23, wherein the DNA polymerase is UmuC or a fragment thereof.

36. The method according to claim 35, wherein UmuC or a fragment thereof is contacted with the DNA molecule in the presence of UmuD', RecA and SSB.

37. The method according to claim 23, wherein the divalent metal ion is selected from the group consisting of $Mg^{+2}$, $Mn^{+2}$, $Zn^{+2}$, $Co^{+2}$, $Ni^{+2}$ and $Fe^{+2}$.

38. The method according to claim 23, wherein the divalent metal ion is $Mg^{+2}$.

* * * * *

SEQUENCE LISTING

```
<160> NUMBER OF SEQ ID NOS:  31

<210> SEQ ID NO 1
<211> LENGTH: 50
<212> TYPE: DNA
<213> ORGANISM: Artificial Sequence
<220> FEATURE:
<223> OTHER INFORMATION: Description of Artificial Sequence: partial
      sequence of gapped lesion
<221> NAME/KEY: misc_feature
<222> LOCATION: (21)..(22)
<223> OTHER INFORMATION: N at position 21 is a synthetic abasic site

<400> SEQUENCE: 1
agtgattccc gtcgtgactg ngaaaaccct gggctacttg aaccagaccg               50

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence:  partial
      sequence of gapped lesion

<400> SEQUENCE: 2
cggtctggtt caagtagcc                                                 19

<210> SEQ ID NO 3
<211> LENGTH: 422
<212> TYPE: PRT
<213> ORGANISM: Escherichia coli

<400> SEQUENCE: 3

Met Phe Ala Leu Cys Asp Val Asn Ala Phe Tyr Ala Ser Cys Glu Thr
  1               5                  10                  15

Val Phe Arg Pro Asp Leu Trp Gly Lys Pro Val Val Val Leu Ser Asn
                 20                  25                  30

Asn Asp Gly Cys Val Ile Ala Arg Asn Ala Glu Ala Lys Ala Leu Gly
             35                  40                  45

Val Lys Met Gly Asp Pro Trp Phe Lys Gln Lys Asp Leu Phe Arg Arg
     50                  55                  60

Cys Gly Val Val Cys Phe Ser Ser Asn Tyr Glu Leu Tyr Ala Asp Met
 65                  70                  75                  80

Ser Asn Arg Val Met Ser Thr Leu Glu Glu Leu Ser Pro Arg Val Glu
                 85                  90                  95

Ile Tyr Ser Ile Asp Glu Ala Phe Cys Asp Leu Thr Gly Val Arg Asn
                100                 105                 110

Cys Arg Asp Leu Thr Asp Phe Gly Arg Glu Ile Arg Ala Thr Val Leu
            115                 120                 125

Gln Arg Thr His Leu Thr Val Gly Val Gly Ile Ala Gln Thr Lys Thr
        130                 135                 140

Leu Ala Lys Leu Ala Asn His Ala Ala Lys Lys Trp Gln Arg Gln Thr
145                 150                 155                 160
```

-continued

```
Gly Gly Val Val Asp Leu Ser Asn Leu Glu Arg Gln Arg Lys Leu Met
                165                 170                 175
Ser Ala Leu Pro Val Asp Asp Val Trp Gly Ile Gly Arg Arg Ile Ser
                180                 185                 190
Lys Lys Leu Asp Ala Met Gly Ile Lys Thr Val Leu Asp Leu Ala Asp
                195                 200                 205
Thr Asp Ile Arg Phe Ile Arg Lys His Phe Asn Val Val Leu Glu Arg
            210                 215                 220
Thr Val Arg Glu Leu Arg Gly Glu Pro Cys Leu Gln Leu Glu Phe
225                 230                 235                 240
Ala Pro Thr Lys Gln Glu Ile Ile Cys Ser Arg Ser Phe Gly Glu Arg
                245                 250                 255
Ile Thr Asp Tyr Pro Ser Met Arg Gln Ala Ile Cys Ser Tyr Ala Ala
                260                 265                 270
Arg Ala Ala Glu Lys Leu Arg Ser Glu His Gln Tyr Cys Arg Phe Ile
                275                 280                 285
Ser Thr Phe Ile Lys Thr Ser Pro Phe Ala Leu Asn Glu Pro Tyr Tyr
            290                 295                 300
Gly Asn Ser Ala Ser Val Lys Leu Leu Thr Pro Thr Gln Asp Ser Arg
305                 310                 315                 320
Asp Ile Ile Asn Ala Ala Thr Arg Ser Leu Asp Ala Ile Trp Gln Ala
                325                 330                 335
Gly His Arg Tyr Gln Lys Ala Gly Val Met Leu Gly Asp Phe Phe Ser
                340                 345                 350
Gln Gly Val Ala Gln Leu Asn Leu Phe Asp Asp Asn Ala Pro Arg Pro
                355                 360                 365
Gly Ser Glu Gln Leu Met Thr Val Met Asp Thr Leu Asn Ala Lys Glu
            370                 375                 380
Gly Arg Gly Thr Leu Tyr Phe Ala Gly Gln Gly Ile Gln Gln Gln Trp
385                 390                 395                 400
Gln Met Lys Arg Ala Met Leu Ser Pro Arg Tyr Thr Thr Arg Ser Ser
                405                 410                 415
Asp Leu Leu Arg Val Lys
                420

<210> SEQ ID NO 4
<211> LENGTH: 2427
<212> TYPE: DNA
<213> ORGANISM: Artificial Sequence
<220> FEATURE:
<221> NAME/KEY: CDS
<222> LOCATION: (1)..(2427)
<223> OTHER INFORMATION: Description of Artificial Sequence:  nucleotide
      seq. encoding maltose binding protein/UMUC fusion
      protein

<400> SEQUENCE: 4 atg aaa atc gaa gaa ggt aaa ctg gta atc tgg att aac ggc gat aaa        48
Met Lys Ile Glu Glu Gly Lys Leu Val Ile Trp Ile Asn Gly Asp Lys
  1               5                  10                  15 ggc tat aac ggt ctc gct gaa gtc ggt aag aaa ttc gag aaa gat acc        96
Gly Tyr Asn Gly Leu Ala Glu Val Gly Lys Lys Phe Glu Lys Asp Thr
             20                  25                  30 gga att aaa gtc acc gtt gag cat ccg gat aaa ctg gaa gag aaa ttc       144
Gly Ile Lys Val Thr Val Glu His Pro Asp Lys Leu Glu Glu Lys Phe
         35                  40                  45 cca cag gtt gcg gca act ggc gat ggc cct gac att atc ttc tgg gca       192
Pro Gln Val Ala Ala Thr Gly Asp Gly Pro Asp Ile Ile Phe Trp Ala
```

-continued

|  |  |  |  |  |  |  |  |  |  |  |  |  |  |  |  |  |
|---|---|---|---|---|---|---|---|---|---|---|---|---|---|---|---|---|
|  |  | 50 |  |  |  | 55 |  |  |  | 60 |  |  |  |  |  |  |

```
cac gac cgc ttt ggt ggc tac gct caa tct ggc ctg ttg gct gaa atc         240
His Asp Arg Phe Gly Gly Tyr Ala Gln Ser Gly Leu Leu Ala Glu Ile
 65                  70                  75                  80 acc ccg gac aaa gcg ttc cag gac aag ctg tat ccg ttt acc tgg gat         288
Thr Pro Asp Lys Ala Phe Gln Asp Lys Leu Tyr Pro Phe Thr Trp Asp
                 85                  90                  95 gcc gta cgt tac aac ggc aag ctg att gct tac ccg atc gct gtt gaa         336
Ala Val Arg Tyr Asn Gly Lys Leu Ile Ala Tyr Pro Ile Ala Val Glu
                100                 105                 110 gcg tta tcg ctg att tat aac aaa gat ctg ctg ccg aac ccg cca aaa         384
Ala Leu Ser Leu Ile Tyr Asn Lys Asp Leu Leu Pro Asn Pro Pro Lys
            115                 120                 125 acc tgg gaa gag atc ccg gcg ctg gat aaa gaa ctg aaa gcg aaa ggt         432
Thr Trp Glu Glu Ile Pro Ala Leu Asp Lys Glu Leu Lys Ala Lys Gly
    130                 135                 140 aag agc gcg ctg atg ttc aac ctg caa gaa ccg tac ttc acc tgg ccg         480
Lys Ser Ala Leu Met Phe Asn Leu Gln Glu Pro Tyr Phe Thr Trp Pro
145                 150                 155                 160 ctg att gct gct gac ggg ggt tat gcg ttc aag tat gaa aac ggc aag         528
Leu Ile Ala Ala Asp Gly Gly Tyr Ala Phe Lys Tyr Glu Asn Gly Lys
                165                 170                 175 tac gac att aaa gac gtg ggc gtg gat aac gct ggc gcg aaa gcg ggt         576
Tyr Asp Ile Lys Asp Val Gly Val Asp Asn Ala Gly Ala Lys Ala Gly
            180                 185                 190 ctg acc ttc ctg gtt gac ctg att aaa aac aaa cac atg aat gca gac         624
Leu Thr Phe Leu Val Asp Leu Ile Lys Asn Lys His Met Asn Ala Asp
    195                 200                 205 acc gat tac tcc atc gca gaa gct gcc ttt aat aaa ggc gaa aca gcg         672
Thr Asp Tyr Ser Ile Ala Glu Ala Ala Phe Asn Lys Gly Glu Thr Ala
210                 215                 220 atg acc atc aac ggc ccg tgg gca tgg tcc aac atc gac acc agc aaa         720
Met Thr Ile Asn Gly Pro Trp Ala Trp Ser Asn Ile Asp Thr Ser Lys
225                 230                 235                 240 gtg aat tat ggt gta acg gta ctg ccg acc ttc aag ggt caa cca tcc         768
Val Asn Tyr Gly Val Thr Val Leu Pro Thr Phe Lys Gly Gln Pro Ser
                245                 250                 255 aaa ccg ttc gtt ggc gtg ctg agc gca ggt att aac gcc gcc agt ccg         816
Lys Pro Phe Val Gly Val Leu Ser Ala Gly Ile Asn Ala Ala Ser Pro
            260                 265                 270 aac aaa gag ctg gca aaa gag ttc ctc gaa aac tat ctg ctg act gat         864
Asn Lys Glu Leu Ala Lys Glu Phe Leu Glu Asn Tyr Leu Leu Thr Asp
    275                 280                 285 gaa ggt ctg gaa gcg gtt aat aaa gac aaa ccg ctg ggt gcc gta gcg         912
Glu Gly Leu Glu Ala Val Asn Lys Asp Lys Pro Leu Gly Ala Val Ala
290                 295                 300 ctg aag tct tac gag gaa gag ttg gcg aaa gat cca cgt att gcc gcc         960
Leu Lys Ser Tyr Glu Glu Glu Leu Ala Lys Asp Pro Arg Ile Ala Ala
305                 310                 315                 320 acc atg gaa aac gcc cag aaa ggt gaa atc atg ccg aac atc ccg cag        1008
Thr Met Glu Asn Ala Gln Lys Gly Glu Ile Met Pro Asn Ile Pro Gln
                325                 330                 335 atg tcc gct ttc tgg tat gcc gtg cgt act gcg gtg atc aac gcc gcc        1056
Met Ser Ala Phe Trp Tyr Ala Val Arg Thr Ala Val Ile Asn Ala Ala
            340                 345                 350 agc ggt cgt cag act gtc gat gaa gcc ctg aaa gac gcg cag act aat        1104
Ser Gly Arg Gln Thr Val Asp Glu Ala Leu Lys Asp Ala Gln Thr Asn
    355                 360                 365 tcg agc tcg aac aac aac aac aat aac aat aac aac aac ctc ggg atc        1152
```

```
Ser Ser Ser Asn Asn Asn Asn Asn Asn Asn Asn Asn Leu Gly Ile
        370                 375                 380 gag gga agg atg ttt gcc ctc tgt gat gta aac gcg ttt tat gcc agc     1200
Glu Gly Arg Met Phe Ala Leu Cys Asp Val Asn Ala Phe Tyr Ala Ser
385                 390                 395                 400 tgt gag acg gtg ttt cgc cct gat tta tgg ggt aaa ccg gtg gtt gtg     1248
Cys Glu Thr Val Phe Arg Pro Asp Leu Trp Gly Lys Pro Val Val Val
                405                 410                 415 cta tcg aat aat gac ggt tgc gtt atc gcc cga aac gct gag gca aag     1296
Leu Ser Asn Asn Asp Gly Cys Val Ile Ala Arg Asn Ala Glu Ala Lys
            420                 425                 430 gcg ctt ggc gtt aaa atg ggc gat ccc tgg ttc aaa caa aaa gat ctg     1344
Ala Leu Gly Val Lys Met Gly Asp Pro Trp Phe Lys Gln Lys Asp Leu
        435                 440                 445 ttt cgt cgc tgt ggc gtg gtt tgc ttt agc agc aat tat gag ctt tac     1392
Phe Arg Arg Cys Gly Val Val Cys Phe Ser Ser Asn Tyr Glu Leu Tyr
450                 455                 460 gca gac atg agc aat cgg gtg atg tcg acg ctg gaa gag cta tcg ccc     1440
Ala Asp Met Ser Asn Arg Val Met Ser Thr Leu Glu Glu Leu Ser Pro
465                 470                 475                 480 cgc gtc gag att tac agt att gat gag gca ttc tgc gat ctg aca ggt     1488
Arg Val Glu Ile Tyr Ser Ile Asp Glu Ala Phe Cys Asp Leu Thr Gly
                485                 490                 495 gtg cgt aat tgt cgc gat ctg act gat ttt ggc aga gaa att cgc gca     1536
Val Arg Asn Cys Arg Asp Leu Thr Asp Phe Gly Arg Glu Ile Arg Ala
            500                 505                 510 acg gtg cta caa cgt acc cat ctt act gtt ggt gtg ggg atc gcc cag     1584
Thr Val Leu Gln Arg Thr His Leu Thr Val Gly Val Gly Ile Ala Gln
        515                 520                 525 acc aaa acg ctg gct aag ctt gcc aat cat gcg gca aaa aaa tgg cag     1632
Thr Lys Thr Leu Ala Lys Leu Ala Asn His Ala Ala Lys Lys Trp Gln
530                 535                 540 cgg cag acg ggt ggg gtg gtg gat tta tca aat ctg gaa cgc cag cgt     1680
Arg Gln Thr Gly Gly Val Val Asp Leu Ser Asn Leu Glu Arg Gln Arg
545                 550                 555                 560 aaa tta atg tct gct ctc ccc gtg gat gac gtc tgg ggg att gga cgg     1728
Lys Leu Met Ser Ala Leu Pro Val Asp Asp Val Trp Gly Ile Gly Arg
                565                 570                 575 cgg atc agc aaa aaa ctg gac gcg atg ggg atc aaa acc gtt ctc gat     1776
Arg Ile Ser Lys Lys Leu Asp Ala Met Gly Ile Lys Thr Val Leu Asp
            580                 585                 590 ttg gcg gat aca gat atc cgg ttt atc cgt aaa cat ttt aat gtc gtg     1824
Leu Ala Asp Thr Asp Ile Arg Phe Ile Arg Lys His Phe Asn Val Val
        595                 600                 605 ctc gaa aga acg gtg cgt gaa ctg cgc ggc gaa ccc tgt ttg caa ctg     1872
Leu Glu Arg Thr Val Arg Glu Leu Arg Gly Glu Pro Cys Leu Gln Leu
610                 615                 620 gaa gag ttt gca ccg acg aag cag gaa att atc tgt tcc cgc tcg ttt     1920
Glu Glu Phe Ala Pro Thr Lys Gln Glu Ile Ile Cys Ser Arg Ser Phe
625                 630                 635                 640 ggt gaa cgc atc acg gat tat ccg tcg atg cgg cag gcc att tgt agt     1968
Gly Glu Arg Ile Thr Asp Tyr Pro Ser Met Arg Gln Ala Ile Cys Ser
                645                 650                 655 tac gct gcc cgg gcg gcg gaa aaa ctt cgc agc gag cat caa tat tgt     2016
Tyr Ala Ala Arg Ala Ala Glu Lys Leu Arg Ser Glu His Gln Tyr Cys
            660                 665                 670 cgg ttt atc tcc acg ttt att aag acg tca cca ttt gcg ctc aat gaa     2064
Arg Phe Ile Ser Thr Phe Ile Lys Thr Ser Pro Phe Ala Leu Asn Glu
        675                 680                 685
```

```
cct tat tac ggc aat agc gcg tcg gta aaa ctg ctg acg ccc act cag    2112
Pro Tyr Tyr Gly Asn Ser Ala Ser Val Lys Leu Leu Thr Pro Thr Gln
    690                 695                 700 gac agc agg gat atc att aac gct gct acg cga tct ctg gat gcc atc    2160
Asp Ser Arg Asp Ile Ile Asn Ala Ala Thr Arg Ser Leu Asp Ala Ile
705                 710                 715                 720 tgg caa gcg ggc cat cgt tac caa aaa gcg ggc gtg atg ctg ggg gat    2208
Trp Gln Ala Gly His Arg Tyr Gln Lys Ala Gly Val Met Leu Gly Asp
                725                 730                 735 ttc ttc agt cag gga gtc gcg cag ctc aat tta ttc gat gac aac gca    2256
Phe Phe Ser Gln Gly Val Ala Gln Leu Asn Leu Phe Asp Asp Asn Ala
            740                 745                 750 ccg cgc ccc ggg agt gag caa ttg atg acg gta atg gat aca ctg aat    2304
Pro Arg Pro Gly Ser Glu Gln Leu Met Thr Val Met Asp Thr Leu Asn
        755                 760                 765 gct aaa gag ggc aga gga aca ctc tat ttt gcc ggg cag ggg atc cag    2352
Ala Lys Glu Gly Arg Gly Thr Leu Tyr Phe Ala Gly Gln Gly Ile Gln
    770                 775                 780 caa caa tgg cag atg aag cga gcc atg ctt tca cca cgt tat aca acg    2400
Gln Gln Trp Gln Met Lys Arg Ala Met Leu Ser Pro Arg Tyr Thr Thr
785                 790                 795                 800 cga agt tct gat tta ctg agg gtc aaa                                2427
Arg Ser Ser Asp Leu Leu Arg Val Lys
                805

<210> SEQ ID NO 5
<211> LENGTH: 809
<212> TYPE: PRT
<213> ORGANISM: Artificial Sequence
<220> FEATURE:
<223> OTHER INFORMATION: :

<400> SEQUENCE: 5

Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
        50                  55                  60

His Asp Arg Phe Gly Gly Tyr Ala Gln Ser Gly Leu Leu Ala Glu Ile
 65                 70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
```

-continued

```
              195                 200                 205
Thr Asp Tyr Ser Ile Ala Glu Ala Ala Phe Asn Lys Gly Glu Thr Ala
        210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
        290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
370                 375                 380

Glu Gly Arg Met Phe Ala Leu Cys Asp Val Asn Ala Phe Tyr Ala Ser
385                 390                 395                 400

Cys Glu Thr Val Phe Arg Pro Asp Leu Trp Gly Lys Pro Val Val Val
                405                 410                 415

Leu Ser Asn Asn Asp Gly Cys Val Ile Ala Arg Asn Ala Glu Ala Lys
                420                 425                 430

Ala Leu Gly Val Lys Met Gly Asp Pro Trp Phe Lys Gln Lys Asp Leu
            435                 440                 445

Phe Arg Arg Cys Gly Val Val Cys Phe Ser Ser Asn Tyr Glu Leu Tyr
    450                 455                 460

Ala Asp Met Ser Asn Arg Val Met Ser Thr Leu Glu Glu Leu Ser Pro
465                 470                 475                 480

Arg Val Glu Ile Tyr Ser Ile Asp Glu Ala Phe Cys Asp Leu Thr Gly
                485                 490                 495

Val Arg Asn Cys Arg Asp Leu Thr Asp Phe Gly Arg Glu Ile Arg Ala
                500                 505                 510

Thr Val Leu Gln Arg Thr His Leu Thr Val Gly Val Gly Ile Ala Gln
            515                 520                 525

Thr Lys Thr Leu Ala Lys Leu Ala Asn His Ala Ala Lys Lys Trp Gln
530                 535                 540

Arg Gln Thr Gly Gly Val Val Asp Leu Ser Asn Leu Glu Arg Gln Arg
545                 550                 555                 560

Lys Leu Met Ser Ala Leu Pro Val Asp Asp Val Trp Gly Ile Gly Arg
                565                 570                 575

Arg Ile Ser Lys Lys Leu Asp Ala Met Gly Ile Lys Thr Val Leu Asp
                580                 585                 590

Leu Ala Asp Thr Asp Ile Arg Phe Ile Arg Lys His Phe Asn Val Val
            595                 600                 605

Leu Glu Arg Thr Val Arg Glu Leu Arg Gly Glu Pro Cys Leu Gln Leu
610                 615                 620
```

```
Glu Glu Phe Ala Pro Thr Lys Gln Glu Ile Ile Cys Ser Arg Ser Phe
625                 630                 635                 640

Gly Glu Arg Ile Thr Asp Tyr Pro Ser Met Arg Gln Ala Ile Cys Ser
            645                 650                 655

Tyr Ala Ala Arg Ala Ala Glu Lys Leu Arg Ser Glu His Gln Tyr Cys
        660                 665                 670

Arg Phe Ile Ser Thr Phe Ile Lys Thr Ser Pro Phe Ala Leu Asn Glu
    675                 680                 685

Pro Tyr Tyr Gly Asn Ser Ala Ser Val Lys Leu Leu Thr Pro Thr Gln
690                 695                 700

Asp Ser Arg Asp Ile Ile Asn Ala Ala Thr Arg Ser Leu Asp Ala Ile
705                 710                 715                 720

Trp Gln Ala Gly His Arg Tyr Gln Lys Ala Gly Val Met Leu Gly Asp
                725                 730                 735

Phe Phe Ser Gln Gly Val Ala Gln Leu Asn Leu Phe Asp Asp Asn Ala
            740                 745                 750

Pro Arg Pro Gly Ser Glu Gln Leu Met Thr Val Met Asp Thr Leu Asn
        755                 760                 765

Ala Lys Glu Gly Arg Gly Thr Leu Tyr Phe Ala Gly Gln Gly Ile Gln
770                 775                 780

Gln Gln Trp Gln Met Lys Arg Ala Met Leu Ser Pro Arg Tyr Thr Thr
785                 790                 795                 800

Arg Ser Ser Asp Leu Leu Arg Val Lys
                805

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
atgtttgccc tctgtgatgt aaacgcg                                         27

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
atgttgttta tcaagcctgc ggatc                                           25

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
ggctttcctt caccggcagc ag                                              22

<210> SEQ ID NO 9
<211> LENGTH: 31
```

```
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
ccggaattct ttatttgacc ctcagtaaat c                              31

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
cggaattcat cagcgcatcg ccttaacg                                  28

<210> SEQ ID NO 11
<211> LENGTH: 60
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (31)..(32)
<223> OTHER INFORMATION: N at position 31 is a synthetic abasic site

<400> SEQUENCE: 11
accgcaacga agtgattccc gtcgtgactg ngaaaaccct gggctacttg aaccagaccg   60

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
ggaatcactt cgttg                                                15

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 13
ctggttcaag tagcc                                                15

<210> SEQ ID NO 14
<211> LENGTH: 60
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (31)..(32)
<223> OTHER INFORMATION: N at position 31 is a synthetic abasic site

<400> SEQUENCE: 14
```
accgcaacga agtgattcct ggcgttaccc nacttaatcg cggctacttg aaccagaccg    60

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 15
ggaatcactt cgttg                                                     15

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16
ctggttcaag tagcc                                                     15

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17
gagaattcgc aatgataccg ccgcaacgaa gtg                                 33

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
cgggatccga aggtggagga aggtg                                          25

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 19
atggggtaaa ccggtggttg t                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 20
ctcattaata ctgtaaatct c                                              21

```
<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 21
gtattaatga ggcattctgc g                                              21

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 22
tgctgcaagg cgattaagt                                                 19

<210> SEQ ID NO 23
<211> LENGTH: 40
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 23
ggaaaaccct ggcgttagcc gacttaatcg ccttgcagca                          40

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 24
aacgccaggg ttttcc                                                    16

<210> SEQ ID NO 25
<211> LENGTH: 201
<212> TYPE: DNA
<213> ORGANISM: lambda phage

<400> SEQUENCE: 25
atggaacaac gcataaccct gaaagattat gcaatgcgct ttgggcaaac caagacagct    60
aaagatctcg gcgtatatca aagcgcgatc aacaaggcca ttcatgcagg ccgaaagatt   120
tttttaacta taaacgctga tggaagcgtt tatgcggaag aggtaaagcc cttcccgagt   180
aacaaaaaaa caacagcata a                                             201

<210> SEQ ID NO 26
<211> LENGTH: 1263
<212> TYPE: DNA
<213> ORGANISM: Conjugative plasmid

<400> SEQUENCE: 26
atgtttgcgc tgattgatgt caatggcatg tacgccagct gtgagcaggc atttaggcca    60
```

-continued

```
gatctggcaa accgagcagt ggccgtttta tccaacaatg acggcaacat tgtggcccgt      120
aattacctgg cgaagaaagc gggcctgaaa atgggcgatc cgtacttcaa agtcagaccc      180
ataatcgagc gtcataacat cgctattttt agctctaatt acactcttta tgcctccatg      240
tcggcccggt tcgcggccgt agttgagtcc cttgcaagcc acgtcgaaca gtattcaatc      300
gacgagcttt tgttgactg caaagggata acggccgcca tgagccttga cgctttcggg       360
cgccaactgc gcgaggaagt caggcgacac acaacgctgg tatgcggggt cggtattgcc      420
cgtactaaga cgctggcgaa gctgtgtaac cacgctgcaa aaacatggcc cgctactggc      480
ggggtggttg ctctggacga tggcgccaga ctgaagaaat taatgagcat cctgccggtt      540
gcggaagtct ggggcgtcgg ccatcgtaca gagaaagcac tcgccacaat ggggatcaaa      600
acggtgctgg atttagccag ggcagatacg cgcctaatcc gtaaaacatt cggcgttgtg      660
cttgaaagaa cggtacggga gttgcgcggc gaggcttgct tcagcctgga agaaaaccct      720
cctgcgaagc agcagattgt tgtgtcgcgc tcattcggcc aacgcgtaga aaccctgacg      780
gacatgcagc aggctgtcac cggatttgca gcgcgcgcag ctgaaaaact gcgtaatgag      840
aggcaatact gccgcgtcat aagcgtctt atccgtacca gtccttattc agtgcgtgat      900
acacagtatg ccaatcaggc aaccgaaaaa ctgacggtgg caacccagga cagccgcacg      960
ataattcagg cagcacaagc gctggcgcgg atctggcggg aagatattgc gtatgcaaaa     1020 gcagggtca tgctggcaga ttttagcggg aaggaggccc agcttgattt attcgactct      1080
gctacgcctt cagctggcag cgaggcttta atggctgttc ttgatggtat aaaccggcgt     1140
ggaaagaacc agcttttttt tgcaggccag ggcatcgata actcctttgc catgcgtcgt     1200
cagatgttgt cacctgatta cacgacagac tggcgctcaa taccaatagc caccatcaaa     1260
taa                                                                   1263
```

<210> SEQ ID NO 27
<211> LENGTH: 420
<212> TYPE: PRT
<213> ORGANISM: Conjugative plasmid

<400> SEQUENCE: 27

```
Met Phe Ala Leu Ile Asp Val Asn Gly Met Tyr Ala Ser Cys Glu Gln
  1               5                  10                  15

Ala Phe Arg Pro Asp Leu Ala Asn Arg Ala Val Ala Val Leu Ser Asn
                 20                  25                  30

Asn Asp Gly Asn Ile Val Ala Arg Asn Tyr Leu Ala Lys Lys Ala Gly
             35                  40                  45

Leu Lys Met Gly Asp Pro Tyr Phe Lys Val Arg Pro Ile Ile Glu Arg
         50                  55                  60

His Asn Ile Ala Ile Phe Ser Ser Asn Tyr Thr Leu Tyr Ala Ser Met
 65                  70                  75                  80

Ser Ala Arg Phe Ala Ala Val Val Glu Ser Leu Ala Ser His Val Glu
                 85                  90                  95

Gln Tyr Ser Ile Asp Glu Leu Phe Val Asp Cys Lys Gly Ile Thr Ala
            100                 105                 110

Ala Met Ser Leu Asp Ala Phe Gly Arg Gln Leu Arg Glu Glu Val Arg
        115                 120                 125

Arg His Thr Thr Leu Val Cys Gly Val Gly Ile Ala Arg Thr Lys Thr
    130                 135                 140

Leu Ala Lys Leu Cys Asn His Ala Ala Lys Thr Trp Pro Ala Thr Gly
145                 150                 155                 160
```

```
Gly Val Val Ala Leu Asp Asp Gly Ala Arg Leu Lys Lys Leu Met Ser
                165                 170                 175
Ile Leu Pro Val Ala Glu Val Trp Gly Val Gly His Arg Thr Glu Lys
            180                 185                 190
Ala Leu Ala Thr Met Gly Ile Lys Thr Val Leu Asp Leu Ala Arg Ala
        195                 200                 205
Asp Thr Arg Leu Ile Arg Lys Thr Phe Gly Val Val Leu Glu Arg Thr
    210                 215                 220
Val Arg Glu Leu Arg Gly Glu Ala Cys Phe Ser Leu Glu Glu Asn Pro
225                 230                 235                 240
Pro Ala Lys Gln Gln Ile Val Val Ser Arg Ser Phe Gly Gln Arg Val
                245                 250                 255
Glu Thr Leu Thr Asp Met Gln Gln Ala Val Thr Gly Phe Ala Ala Arg
            260                 265                 270
Ala Ala Glu Lys Leu Arg Asn Glu Arg Gln Tyr Cys Arg Val Ile Ser
        275                 280                 285
Val Phe Ile Arg Thr Ser Pro Tyr Ser Val Arg Asp Thr Gln Tyr Ala
    290                 295                 300
Asn Gln Ala Thr Glu Lys Leu Thr Val Ala Thr Gln Asp Ser Arg Thr
305                 310                 315                 320
Ile Ile Gln Ala Ala Gln Ala Leu Ala Arg Ile Trp Arg Glu Asp Ile
                325                 330                 335
Ala Tyr Ala Lys Ala Gly Val Met Leu Ala Asp Phe Ser Gly Lys Glu
            340                 345                 350
Ala Gln Leu Asp Leu Phe Asp Ser Ala Thr Pro Ser Ala Gly Ser Glu
        355                 360                 365
Ala Leu Met Ala Val Leu Asp Gly Ile Asn Arg Arg Gly Lys Asn Gln
    370                 375                 380
Leu Phe Phe Ala Gly Gln Gly Ile Asp Asn Ser Phe Ala Met Arg Arg
385                 390                 395                 400
Gln Met Leu Ser Pro Asp Tyr Thr Thr Asp Trp Arg Ser Ile Pro Ile
                405                 410                 415
Ala Thr Ile Lys
        420

<210> SEQ ID NO 28
<211> LENGTH: 441
<212> TYPE: DNA
<213> ORGANISM: Conjugative plasmid

<400> SEQUENCE: 28
atgaaggtcg atattttga aagctccggc gccagccggg tacacagcat ccctttttat    60
ctgcaaagaa tttctgcggg gttccccagc ccggcccagg gctatgaaaa gcaggagtta   120
aacctgcatg agtattgtgt tcgtcaccct tcagcaactt acttcctgcg ggtttctggc   180
tcgtcaatgg aagatggccg catccatgat ggtgacgtac tggttgtgga tcgctcgctg   240
acggccagcc acggctcaat cgtagtcgcc tgcatccata tgaatttac cgtgaagcga   300
ctactgctga ggcccagacc ctgcctgatg ccgatgaaca aagatttcc tgtgtactac   360
attgacccgg ataatgagag cgttgaaatc tggggagtgg ttacgcattc ccttatcgag   420
catccggtat gtttgcgctg a                                              441

<210> SEQ ID NO 29
<211> LENGTH: 146
```

```
<212> TYPE: PRT
<213> ORGANISM: Conjugative plasmid

<400> SEQUENCE: 29

Met Lys Val Asp Ile Phe Glu Ser Ser Gly Ala Ser Arg Val His Ser
 1               5                  10                  15

Ile Pro Phe Tyr Leu Gln Arg Ile Ser Ala Gly Phe Pro Ser Pro Ala
             20                  25                  30

Gln Gly Tyr Glu Lys Gln Glu Leu Asn Leu His Glu Tyr Cys Val Arg
         35                  40                  45

His Pro Ser Ala Thr Tyr Phe Leu Arg Val Ser Gly Ser Ser Met Glu
     50                  55                  60

Asp Gly Arg Ile His Asp Gly Asp Val Leu Val Val Asp Arg Ser Leu
 65                  70                  75                  80

Thr Ala Ser His Gly Ser Ile Val Val Ala Cys Ile His Asn Glu Phe
                 85                  90                  95

Thr Val Lys Arg Leu Leu Leu Arg Pro Arg Pro Cys Leu Met Pro Met
            100                 105                 110

Asn Lys Asp Phe Pro Val Tyr Tyr Ile Asp Pro Asp Asn Glu Ser Val
        115                 120                 125

Glu Ile Trp Gly Val Val Thr His Ser Leu Ile Glu His Pro Val Cys
    130                 135                 140

Leu Arg
145

<210> SEQ ID NO 30
<211> LENGTH: 366
<212> TYPE: DNA
<213> ORGANISM: Artificial Sequence
<220> FEATURE:
<223> OTHER INFORMATION: Description of Artificial Sequence:
      Recombinant mucA' gene

<400> SEQUENCE: 30
atggggttcc ccagcccggc ccagggctat gaaaagcagg agttaaacct gcatgagtat       60
tgtgttcgtc acccttcagc aacttacttc ctgcgggttt ctggctcgtc aatggaagat      120
ggccgcatcc atgatggtga cgtactggtt gtggatcgct cgctgacggc cagccacggc      180
tcaatcgtag tcgcctgcat ccataatgaa tttaccgtga agcgactact gctgaggccc      240
agaccctgcc tgatgccgat gaacaaagat tttcctgtgt actacattga cccggataat      300
gagagcgttg aaatctgggg agtggttacg cattccctta tcgagcatcc ggtatgtttg      360
cgctga                                                                 366

<210> SEQ ID NO 31
<211> LENGTH: 120
<212> TYPE: PRT
<213> ORGANISM: Artificial Sequence
<220> FEATURE:
<223> OTHER INFORMATION: Description of Artificial Sequence:
      Recombinant MucA'

<400> SEQUENCE: 31

Gly Phe Pro Ser Pro Ala Gln Gly Tyr Glu Lys Gln Glu Leu Asn Leu
 1               5                  10                  15

His Glu Tyr Cys Val Arg His Pro Ser Ala Thr Tyr Phe Leu Arg Val
             20                  25                  30

Ser Gly Ser Ser Met Glu Asp Gly Arg Ile His Asp Gly Asp Val Leu
         35                  40                  45
```

-continued

```
Val Val Asp Arg Ser Leu Thr Ala Ser His Gly Ser Ile Val Val Ala
     50                  55                  60

Cys Ile His Asn Glu Phe Thr Val Lys Arg Leu Leu Leu Arg Pro Arg
 65                  70                  75                  80

Pro Cys Leu Met Pro Met Asn Lys Asp Phe Pro Val Tyr Tyr Ile Asp
                 85                  90                  95

Pro Asp Asn Glu Ser Val Glu Ile Trp Gly Val Val Thr His Ser Leu
                100                 105                 110

Ile Glu His Pro Val Cys Leu Arg
        115                 120
```